(12) United States Patent
Clube

(10) Patent No.: US 11,931,426 B2
(45) Date of Patent: Mar. 19, 2024

(54) RECOMBINOGENIC NUCLEIC ACID STRANDS IN SITU

(71) Applicant: SNIPR Technologies Limited, Peterborough (GB)

(72) Inventor: Jasper Clube, London (GB)

(73) Assignee: SNIPR TECHNOLOGIES LIMITED, Peterborough (GB)

( * ) Notice: Subject to any disclaimer, the term of this patent is extended or adjusted under 35 U.S.C. 154(b) by 0 days.

(21) Appl. No.: 18/356,029

(22) Filed: Jul. 20, 2023

(65) Prior Publication Data
US 2023/0364268 A1    Nov. 16, 2023

Related U.S. Application Data

(60) Continuation of application No. 16/993,009, filed on Aug. 13, 2020, which is a division of application No. 16/020,846, filed on Jun. 27, 2018, now Pat. No. 10,751,427, which is a continuation of application No. PCT/EP2016/082942, filed on Dec. 30, 2016.

(30) Foreign Application Priority Data

Jan. 10, 2016 (GB) .................................... 1600417

(51) Int. Cl.
| | |
|---|---|
| C12N 15/63 | (2006.01) |
| A61K 35/74 | (2015.01) |
| A61K 48/00 | (2006.01) |
| A61P 31/04 | (2006.01) |
| C12N 9/22 | (2006.01) |
| C12N 15/90 | (2006.01) |
| C12P 19/34 | (2006.01) |
| C12N 15/70 | (2006.01) |
| C12N 15/74 | (2006.01) |

(52) U.S. Cl.
CPC .......... *A61K 48/0066* (2013.01); *A61K 35/74* (2013.01); *A61P 31/04* (2018.01); *C12N 9/22* (2013.01); *C12N 15/63* (2013.01); *C12N 15/905* (2013.01); *C12N 15/907* (2013.01); *C12P 19/34* (2013.01); *C12N 15/70* (2013.01); *C12N 15/74* (2013.01); *C12N 15/902* (2013.01); *C12N 2310/20* (2017.05); *C12N 2800/80* (2013.01)

(58) Field of Classification Search
CPC .......... C12N 9/22; C12N 15/63; C12N 15/70; C12N 15/75; C12N 15/79; C12N 15/85; C12N 15/86; C12N 2310/20; C07H 21/02; C07H 21/04
See application file for complete search history.

(56) References Cited

U.S. PATENT DOCUMENTS

| | | |
|---|---|---|
| 10,751,427 B2 | 8/2020 | Clube |
| 2018/0326093 A1 | 11/2018 | Clube |
| 2021/0060180 A1 | 3/2021 | Clube |

FOREIGN PATENT DOCUMENTS

WO    2015095804 A1    6/2015

OTHER PUBLICATIONS

Jinek et al., 2012 (Science, vol. 337 (6096), p. 816-821).*
Zetsche et al., 2015 (Cell, vol. 163, p. 759-771).*
Sinkunas et al., 2011 (The EMBO Journal, vol. 30, p. 1335-1342).*
Carrington et al., 2015 (Nucleic Acids Research, vol. 43, No. 22, e157, p. 1-8).*
Bugrysheva, J.V. et al. (Jul. 2011). "The Histone-Like Protein Hip Is Essential for Growth of 20 *Streptococcus pyogenes*: Comparison of Genetic Approaches to Study Essential Genes," Appl Environ Microbiol. 77(13):4422-4428.
Cristea, S. et al. (2013, e-pub. Oct. 5, 2012). "In vivo Cleavage of Transgene Donors Promotes Nuclease-Mediated Targeted Integration," Biotechnol. & Bioeng. 110(3):871-880.
De Piˆdoue, G. et al. (May 2005). "Improving Gene Replacement by Intracellular Formation of Linear Homologous DNA," Journal of Gene Medicine 7(5):649-656.
Dunbar, C.E. et al. (Jan. 12, 2018). "Gene Therapy Comes of Age," Science 359(175):1-10.
Final Office Action, dated Jun. 5, 2020, for U.S. Appl. No. 16/020,846, filed Jun. 27, 2018, 7 pages.
Flynn, R. et al. (Mar. 5, 2015). "CRISPR-Mediated Genotypic and Phenotypic Correction of a Chronic Granulomatous Disease Mutation in Human iPS Cells," Experimental Hematology 43(10):838-848.
Hisano, Y. et al. (Mar. 5, 2015). "Precise In-Frame Integration of Exogenous DNA Mediated by CRISPR/Cas9 System in Zebrafish," Scientific Reports 5:8841, 7 pages.
Hoshijima, K. et al. (Mar. 21, 2016). "Precise Editing of the Zebrafish Genome Made Simple and Efficient," Development Cell 36(6):654-667.
International Search Report, dated Jun. 1, 2017, for PCT Application No. PCT/EP2016/082942, filed Dec. 30, 2016, 7 pages.
Jiang, W. et al. (Mar. 2013, e-pub. Sep. 1, 2013). "CRISPR-Assisted Editing of Bacterial Genomes," Nat. Biotechnol. 31(3):233-239.
Jiang, W. et al. (Sep. 1, 2015). "Cas9-Assisted Targeting of Chromosome Segments CATCH Enables One-Step Targeted Cloning of large Gene Clusters," Nature Communications 6(1):8101, 8 pages.
Kaur, T. et al. (2009). "Addressing the Challenge: Current and Future Directions in Ovarian Cancer Therapy," Current Gene Therapy 9:434-458.

(Continued)

*Primary Examiner* — Shin Lin Chen
(74) *Attorney, Agent, or Firm* — MORRISON & FOERSTER LLP

(57) ABSTRACT

The invention relates to retrieving or modifying target nucleic acids, such as host cell chromosomal DNA, by homologous recombination with vectors that have been cut to provide recombinogenic nucleic acid strands in situ. In some aspects, a marker sequence is created by the method of the invention, wherein the marker sequence is in the product of the method but not present in the starting nucleic acid strands of the method.

12 Claims, 23 Drawing Sheets

(56) References Cited

OTHER PUBLICATIONS

Lee, N.C.O. et al. (2015, e-pub. Feb. 17, 2015). "Highly Efficient CRISPR/CAS9-Mediated TAR Cloning of Genes and Chromosomal Loci From Complex Genomes in Yeast," Nucleic Acids Research 43(8):e55, 9 pages.
Lenzi, R.N. et al. (2014). "2-Gene Transfer Research: The Evolution of the Clinical Science," NCBI Bookshelf, A Service of the National Library of Medicine, National Institute of Health, pp. 1-16.
Moore, R. et al. (Jan. 30, 2015). "CRISPR-Based Self-Cleaving Mechanism for Controllable Gene Delivery in Human Cells," Nucleic Acids Research 43(2):1297-1303.
Non-Final Office Action, dated Apr. 10, 2023, for U.S. Appl. No. 16/993,009, filed Aug. 18, 2020, 18 pages.
Non-Final Office Action, dated Dec. 26, 2019, for U.S. Appl. No. 16/020,846, filed Jun. 27, 2018, 22 pages.
Shim, G. et al. (2017). "Nonviral Delivery Systems for Cancer Gene Therapy: Strategies and Challenges," Current Gene Therapy 17(5):1-18.
Written Opinion of the International Search Authority, dated Jun. 1, 2017, for PCT Application No. PCT/EP2016/082942, filed Dec. 30, 2016, 11 pages.
Zhang, W. et al. (Jan. 16, 2014). "Multiple Copies of a Linear Donor Fragment Released In Situ From a Vector Improved the efficiency of Zinc-Finger Nuclease-Mediated Genome Editing," Gene Therapy 21(3):282-288.

\* cited by examiner

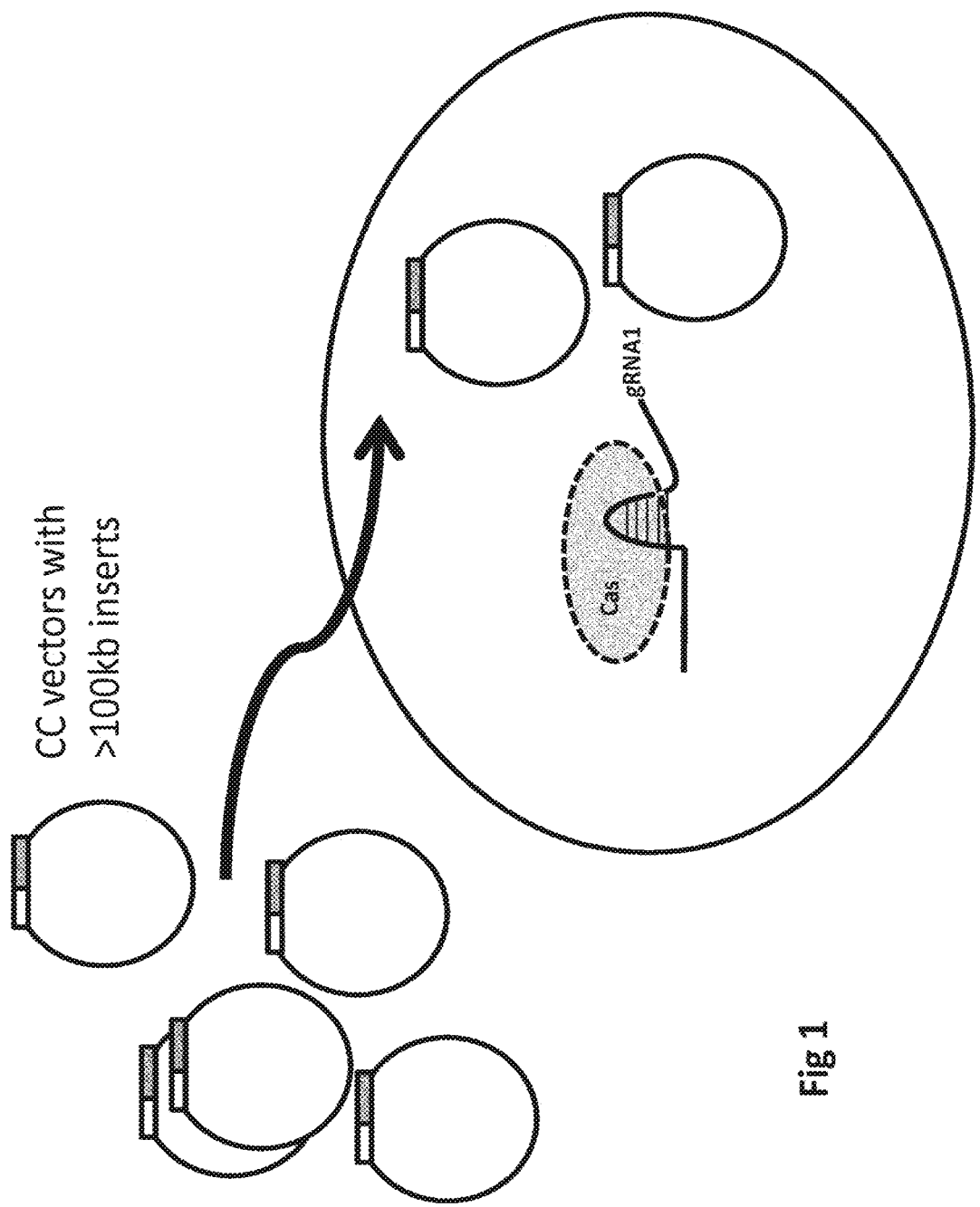

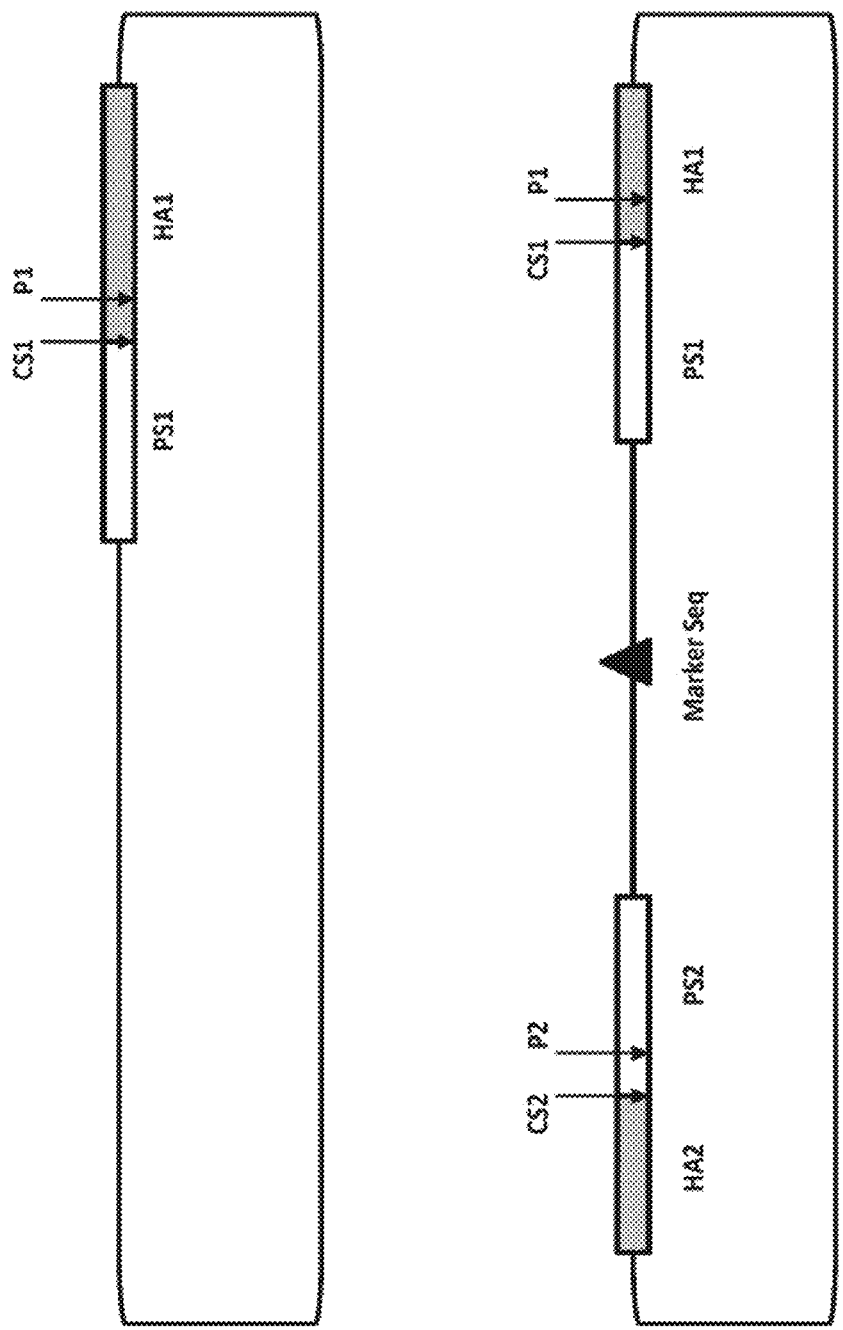

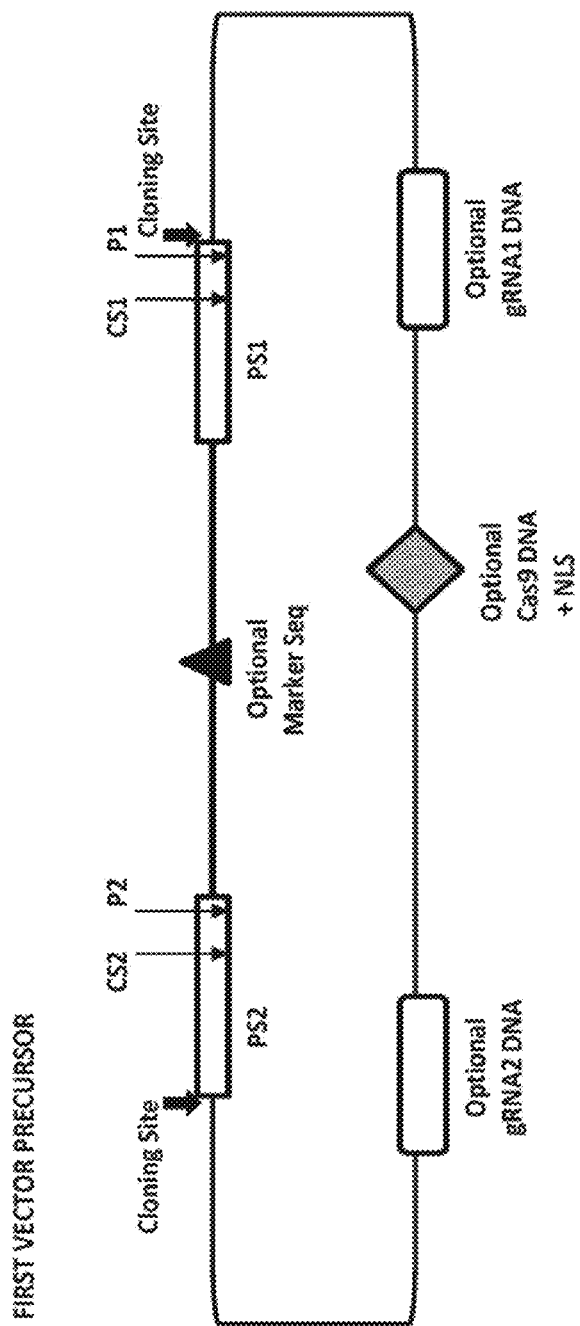

RECOMBINOGENIC NUCLEIC ACID STRANDS IN SITU

CROSS-REFERENCE TO RELATED APPLICATIONS

This application is a continuation application of U.S. patent application Ser. No. 16/993,009, filed on Aug. 13, 2020, which is a divisional application of U.S. patent application Ser. No. 16/020,846, filed Jun. 27, 2018, now U.S. Pat. No. 10,751,427, which issued on Aug. 25, 2020, which is a continuation application of International Application No. PCT/EP2016/082942, filed on Dec. 30, 2016, which claims priority to GB Application No. 1600417.8, filed on Jan. 10, 2016, the contents of which are incorporated herein by reference in their entireties.

FIELD OF THE INVENTION

The invention relates to retrieving or modifying target nucleic acids, such as host cell chromosomal DNA, by homologous recombination with vectors that have been cut in a cell (eg, precisely cut using Cas nuclease) to provide recombinogenic nucleic acid strands in situ.

BACKGROUND OF THE INVENTION

Transformation-associated recombination (TAR) cloning is a method for isolating a large chromosomal region from a mammalian genome which relies on yeast *Saccharomyces cerevisiae*. In TAR cloning, total genomic DNA is extracted from a cell and co-transformed into yeast cells along with a vector carrying targeting sequences specific to a gene of interest. Upon co-transformation into yeast, homologous recombination occurs between the vector' hooks and targeted genomic sequences flanking the gene of interest to form a circular YAC (Yeast Artificial Chromosome). Chromosomal regions with sizes ranging to 250 kb have been isolated by TAR. Subsequent manipulation is required if sequences are required in a non-YAC vector, such as movement of sequence from a YAC to a BAC for downstream use.

Reference is made to Nat Commun. 2015 Sep. 1; 6:8101. doi: 10.1038/ncomms9101; "Cas9-Assisted Targeting of CHromosome segments CATCH enables one-step targeted cloning of large gene clusters", Jiang W et al. The authors described a cloning method in which a target genome segment is excised from bacterial chromosomes in vitro by the RNA-guided Cas9 nuclease at two designated loci, and ligated to a cloning vector by Gibson assembly.

Engineered CRISPR/Cas systems have been used for precise modification of nucleic acid in various types of prokaryotic and eukaryotic cells, ranging from bacterial to animal and plant cells (eg, see Jiang W et al (2013)). Cutting of target nucleic acid has been proposed to generate recombinogenic, free ends in target nucleic acid. These ends promote homologous recombination with partner nucleic acid by homology-directed repair (HDR) mechanisms, eg, for insertion of partner sequence into the target. Current Cas-based techniques are, however, limited by the need to scour host cell genomes (or other target nucleic acids) to find PAM sites to match the desired Cas and then to select only those that are adjacent sufficiently unique protospacer sequences in the genome. Ideally, the protospacer/PAM combination should be unique to minimise the chances of off-target cutting, but this can be difficult to achieve in practice. This limits utility for gene therapy in human and other settings where accuracy is paramount. Furthermore, the need to use sites already in the genome reduces flexibility to freely target desired areas of the genome for homologous recombination.

STATEMENTS OF INVENTION

In a first configuration, the invention provides:—
A method of retrieving a nucleic acid sequence from a donor nucleic acid strand, the method comprising
(a) providing a nucleic acid vector comprising a first nucleic acid strand, wherein the first strand comprises:—
   i. a first homology arm (HA1) that is homologous to a first nucleotide sequence (NS1) of the donor strand for homologous recombination between the strands;
   ii. a second homology arm (HA2) that is homologous to a second nucleotide sequence (NS2) of the donor strand for homologous recombination between the strands; and
   iii. an intervening nucleotide sequence joining the 3' end of HA1 to the 5' end of HA2;
   wherein HA1 is 5' to HA2 in the first strand; and NS1 is 3' of NS2 in the donor strand,
   wherein the donor strand comprises a retrieval sequence (RS) between NS1 and NS2;
(b) combining the first strand with the donor strand;
(c) nuclease cutting of a first cut site (CS1) of the first strand at the 5' end of HA1, or flanking 5' of said end; and/or nuclease cutting of a second cut site (CS2) of the first strand at the 3' end of HA2, or flanking 3' of said end;
wherein steps (b) and (c) are carried out in any order or simultaneously;
(d) carrying out homologous recombination of the cut first strand with the donor strand, whereby gap repair of the first strand produces a vector in which RS is retrieved between HA1 and HA2; and
(e) optionally isolating or sequencing the vector or the RS sequence thereof.

In an example, steps (b) to (d) are performed in a host cell; and/or the product of step (d) is a circular vector.

In an alternative, HA1 is 5' to HA2 in the first strand; and NS1 is 5' of NS2 in the donor strand, wherein the donor strand comprises a retrieval sequence (RS) between NS1 and NS2; wherein step (c) Instead comprises nuclease cutting of a first cut site (CS1) of the first strand at the 5' end of HA1, or flanking 5' of said end; and/or nuclease cutting of a second cut site (CS2) of the first strand at the 3' end of HA2, or flanking 3' of said end. Advantageously the vector is a linear immediately before step (c).

In a second configuration, the invention provides:—
A method of modifying a nucleic acid sequence, the method comprising
(a) providing a nucleic acid vector comprising a first nucleic acid strand, wherein the first strand comprises:—
   i. a first homology arm (HA1) that is homologous to a first nucleotide sequence (NS1) of a further nucleic acid strand for homologous recombination between the strands;
   ii, a second homology arm (HA2) that is homologous to a second nucleotide sequence (NS2) of the donor strand for homologous recombination between the strands; and
   iii, an intervening sequence (IS) joining the 3' end of HA1 to the 5' end of HA2;

wherein HA2 is 5' to HA1 in the first strand; and NS2 is 5' of NS1 in the further strand,
wherein the further strand optionally comprises a sequence (DS) between NS1 and NS2;
(b) combining the first strand with the further strand;
(c) using nuclease (eg, Cas nuclease) cutting of a cut site (CS3) of the first strand at the 3' end of HA1, or flanking 3' of said end; and/or Cas nuclease cutting of a cut site (CS4) of the first strand at the 5' end of HA2, or flanking 5' of said end;
wherein steps (b) and (c) are carried out in any order or simultaneously;
(d) carrying out homologous recombination or site-specific recombination of the first strand with the further strand, whereby a product further strand is produced in which IS is inserted between NS1 and NS2 and optionally DS is deleted from the further strand; and
(e) optionally isolating or sequencing after (d) the vector, the product further strand or IS thereof.

In a third configuration, the invention provides:—
A method of making a first nucleic acid strand suitable for homologous recombination with a second nucleic acid strand, eg, in a method according to any preceding configuration, the method of making comprising:—
(a) identifying first and second nucleotides sequences (NS1 and NS2) of the second strand, optionally wherein NS1 is selected so that it is 3' of NS2 in the second strand;
(b) combining in another nucleic acid strand
  i. a first homology arm (HA1) complementary to first predetermined target nucleotide sequence NS1 of the second strand for homologous recombination between HA1 and NS1;
  ii. a second homology arm (HA2) complementary to second predetermined target nucleotide sequence NS2 of the second strand for homologous recombination between HA2 and NS2; and
  iii. a first protospacer sequence (PS1) adjacent a PAM (P1), wherein P1 is cognate to a first Cas nuclease for cutting PS1 at a first cut site (CS1), wherein CS1 is at the 5' end of HA1 or flanking 5' of said end; and/or a second protospacer sequence (PS2) adjacent a PAM (P2), wherein P2 is cognate to said first or a different Cas nuclease for cutting PS2 at a second cut site (CS2), wherein CS2 is at the 3' end of HA2 or flanking 3' of said end;
  whereby the first strand is produced.

In a fourth configuration, the invention provides:—
A method of inhibiting viability, growth or proliferation of a prokaryotic host cell, the method comprising
(a) providing a first vector comprising a protospacer sequence (PS1) adjacent a PAM (P1) that is cognate to a first Cas nuclease;
(b) providing a toxin or toxin precursor; or a vector comprising a sequence encoding a toxin or toxin precursor, wherein the toxin is toxic to the prokaryotic cell;
(c) combining the cell with the vector(s) wherein the vector(s) are introduced into the cell, and providing the toxin in the cell; and
(d) using Cas nuclease cutting of PS1 of the first vector using the first Cas nuclease, wherein the cutting promotes toxin activity in the cell, whereby the cell is killed or cell growth or proliferation reduced.

In a fifth configuration, the invention provides:—
A method of transforming a host cell, the method comprising
(a) providing a first nucleic acid vector, the vector being in a first state comprising
  i. a protospacer sequence (PS1) adjacent a PAM (P1) that is cognate to a first Cas nuclease; and
  ii. a first nucleotide sequence comprising a first marker sequence for marking the first state of the vector;
(b) combining the cell with the vector wherein the vector is introduced into the cell; and
(c) using Cas nuclease cutting of PS1 of the first vector using the first Cas nuclease, wherein the cutting converts the vector to a second state in which the marker sequence is rendered non-functional; and
(d) optionally detecting the second state by detecting that the marker is non-functional in the cell.

In a sixth configuration, the invention provides:—
A vector for transformation of a eukaryotic cell, wherein the vector comprises a first nucleic acid strand and the cell comprises a second nucleic acid strand, the first strand comprising
(a) an insert sequence (IS) flanked by a first homology arm (HA1), wherein HA1 is complementary to a predetermined nucleotide sequence (NS1) of the second strand, wherein HA1 is capable of homologous recombination with NS1 in the eukaryotic cell to modify one or both strands;
(b) a first protospacer sequence (PS1) adjacent a PAM (P1), wherein P1 is cognate to a first Cas nuclease for cutting PS1 at a first cut site (CS1);
(c) wherein CS1 is at an end of, or flanking, HA1, wherein CS1 is capable of being cut by the first Cas to produce a cut first strand wherein HA1 is capable of homologous recombination with NS1.

In a seventh configuration, the invention provides:—
A method of producing a precursor vector, wherein the vector is a precursor of the vector recited in the third configuration, the precursor vector comprising
(a) in 5' to 3' order, a first protospacer sequence (PS1) adjacent a PAM (P1), wherein P1 is cognate to a first Cas nuclease for cutting PS1 at a first cut site (CS1); and
(b) a first nucleotide sequence immediately 3' of P1, wherein the first sequence comprises a first cloning site adjacent the 3' end of P1, or flanking 3' of said end, for cloning a second nucleic acid sequence into the precursor vector, wherein the second sequence comprises one or both of HA1 and HA2;
the method comprising
(c) obtaining a precursor nucleic acid;
(d) identifying the cloning site in the nucleic acid or creating the cloning site in the nucleic acid; and
(e) Identifying the PS1/P1 combination in the nucleic acid or creating the combination in the nucleic acid;
(f) wherein (d) and (e) are carried out in any order or simultaneously, and wherein at least one of (d) and (e) comprises a said creating step, whereby said precursor vector is produced and optionally isolated.

In a eighth configuration, the invention provides:—
A method of modifying a nucleic acid in a eukaryotic cell, the method comprising
(a) Providing a eukaryotic cell containing
  i. a closed circular nucleic acid vector, wherein the vector comprises a first nucleic acid strand;
  ii. a second nucleic acid strand, wherein the second strand is comprised by a chromosome of the cell; and
  iii. a nucleotide sequence encoding a Cas nuclease and a nucleotide sequence encoding a nuclear localisation signal (NLS);

(b) Using Cas nuclease cutting to cut the first strand of the vector inside the cell to produce recombinogenic vector nucleic acid; and (c) Using homologous recombination inside the cell between the cut first strand and the second strand and exchanging a sequence of at least 10 kb of contiguous nucleotides between the first and second strands, thereby forming at least one modified strand; and (d) Optionally isolating or sequencing a modified strand or the cell.

The invention also provides vectors, phage, cells, compositions, collections, populations, medicaments, antibiotics, uses and methods according to any configuration. The invention provides a modified strand, first strand, donor strand, further strand, vector, composition, medicament or kit obtainable by the method of the invention.

Any features on one configuration herein are, in an example, combined with a different configuration of the invention for possible inclusion of such combination in one or more claims herein.

BRIEF DESCRIPTION OF DRAWINGS

FIG. 1 is a schematic showing combining of closed circular vectors with in situ Cas cutting in Eukaryotic cells for exchange of large nucleotide sequences.

FIG. 3B shows a variation where PAM sites have been identified in the homology arm(s), engineered into the arm(s) or the arm(s) have been selected from sequence of the target nucleic acid or cell to contain appropriately placed PAM.

As seen in FIG. 48, HR with a donor strand retrieves a donor fragment containing a desired RS. The closed circular vector, as is illustrated in FIG. 4C, can be used in gene therapy or to modify a target nucleic acid in vitro or in any prokaryotic or eukaryotic cell using HR, with large or very large sequences containing RS being manageable by virtue of being harboured by a closed circular vector. As shown in FIG. 40, this allows for RMCE insertion of RS and also for specifically introducing changes into the target.

FIGS. 6A and 68 show an application of an insert vector where Cas cutting is at one site close to a first homology arm. In this example, replacement of a target sequence takes place (FIG. 8B).

DETAILED DESCRIPTION

Figure 2A:
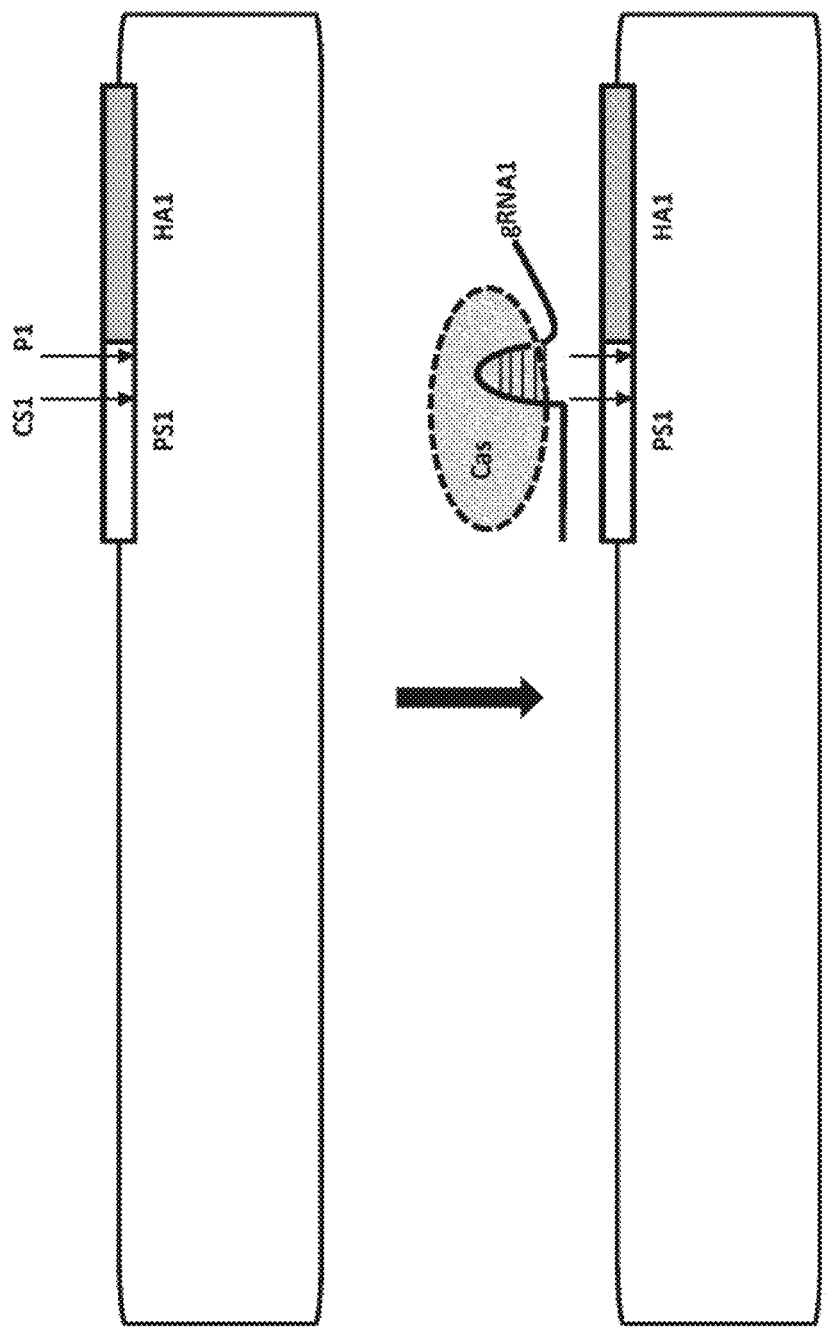
FIGS. 2A & B show a single-arm vector for use in the present invention.
Figure 2B:
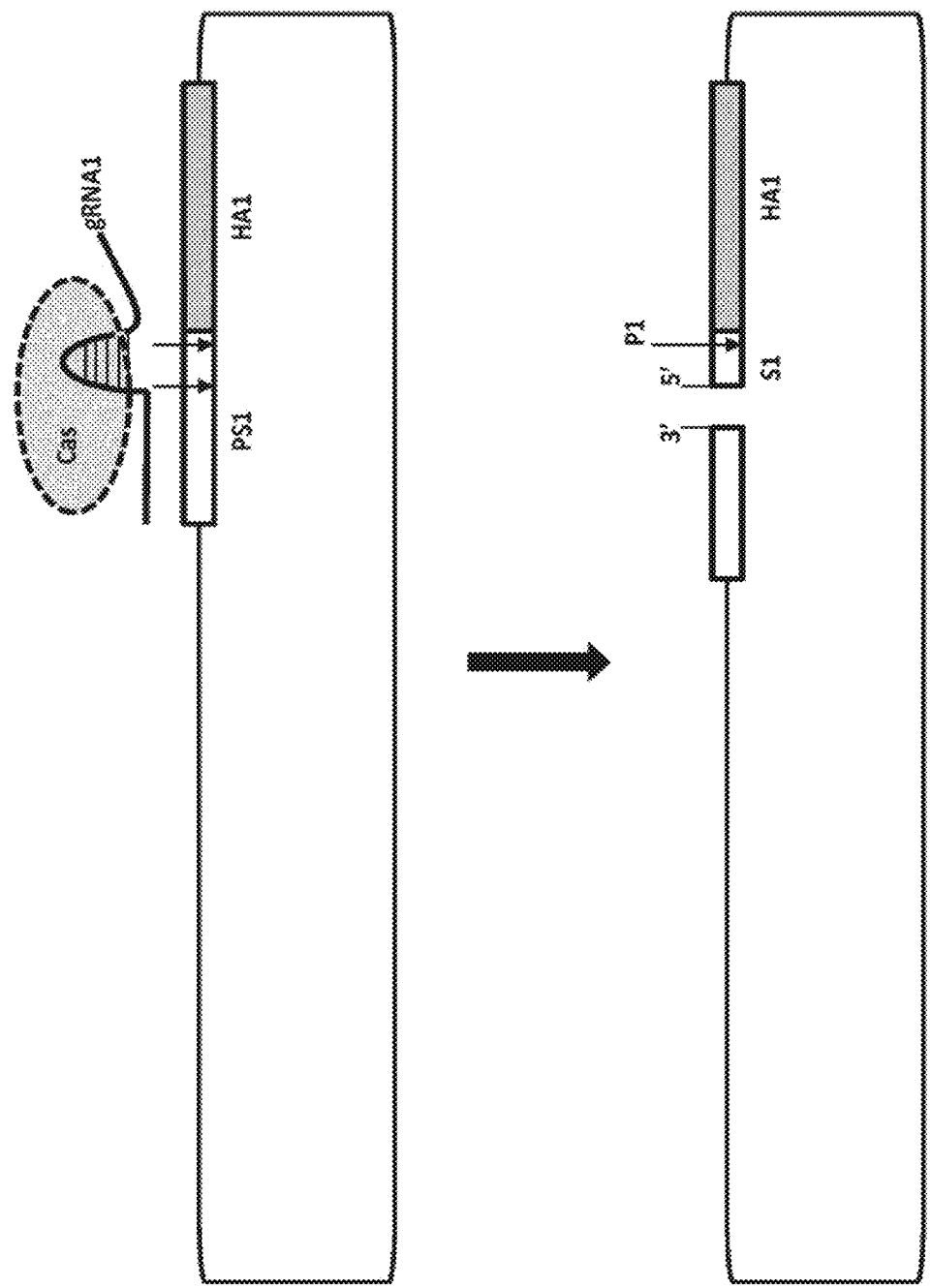

The invention, in its various configurations, addresses one or more of the problems of the art and provides a solution that focuses on vector nucleic acid, rather than host cell target nucleic acid, to enable design of specific, predetermined sites for cutting (eg, Cas cutting). In this way, the invention provides a flexible system. In which the user is free to choose and engineer specific sites for cutting, thereby avoiding the need to choose only limited sites in the target nucleic acid. Engineering can be simply performed in vitro using standard recombineering or other techniques to make a vector where cutting (eg, Cas cutting) sites have been carefully designed and positioned. This allows the user to freely position cutting (eg, Cas cutting) close to homology arms and markers which can be used in subsequent homologous recombination methods with target nucleic acid.

Although aspects of the invention are described with reference to use of Cas cutting, in an alternative other means of cutting can be used, eg, restriction endonucleases cutting, TALEN-mediated cutting, zinc finger-mediated cutting and meganuclease cutting. In an example, the cutting is enzymatic such as nuclease cutting, guided nuclease cutting or RNA guided nuclease cutting.

Thus, the invention relates to modifying target nucleic acids, such as host cell chromosomal DNA, by homologous recombination with vectors that have been precisely cut using Cas nuclease or other cutting means to provide recombinogenic nucleic acid strands. The invention, in one aspect, involves precise cutting to position recombinogenic end(s) close to homology arm(s) in the vector nucleic acid to promote homologous recombination. In this way, precision or efficiency may be promoted. This aspect is particularly useful, in an example, in the context of retrieval or insertion vectors and avoids the need to find appropriate locations in the target for cutting to promote homologous recombination.

Another advantage of the invention is the ability to construct vectors with very large insert sequences (eg, 100 kb or more). In an initial step empty vectors can be introduced, eg, as closed circular vectors, into host cells. Subsequent vector cutting with Cas or by other means inside the cell produces recombinogenic ends in situ for homologous recombination insertion of the large insert sequences into host nucleic acid. This avoids prior art problems with cutting outside cells to produce large sequences that are difficult to handle and purify, and are poorly taken up by target cells (see eg, Jiang et al (2015) infra). Jiang et al (2015) identified reduced efficiency in their technique due to mechanical shearing of long DNA fragments during manipulation outside cells and lower ligation efficiency of Gibson assembly with longer DNA. Furthermore, the requirement to embed cells in an agarose gel severely limited availability of enough DNA for Gibson assembly.

Advantageously, by focusing on engineering of incoming vector nucleic acid, the invention provides flexibility in the exact sequence of the motifs, such as protospacers, to used to direct cutting. In this respect, the user is able to choose sequences, such as protospacer sequences, that have sequence motifs that are not found in the host cell type or are rare in such host cells or are not found in the RS in the cell genome. In an example, the vector protospacers can be based on sequences found in prokaryotes (such as a sequence of a bacterial Pribnow box; bacterial leader sequence (eg, Pel B); bacterial −10 sequence or bacterial −35 element sequence (eg, TATAAT or TTGACA); a bacterial upstream promoter element (UP element) sequence; bacterial regulatory or operon sequence; or a bacterial origin of replication sequence). In this way, Cas cutting is directed by sequences that are not or extremely rarely found in eukaryotic cells (such as human cells) and this greatly assists in avoiding off-target Cas cutting inside the target cells. In an alternative, the invention allows use of entirely synthetic protospacer sequences that can be pre-checked against host cell genomic sequence to determine their uniqueness. These benefits find application in gene therapy of cells and organisms, for embodiment. The invention is also applicable to in vitro modification of target nucleic acids, eg, using recombineering in vitro.

The invention's advantages, in certain configurations, are therefore based on the focusing of cutting (eg, Cas cutting) in the vector, the ability to pre-design and simply engineer the cutting sites, the ability to pre-check and control cutting motif (eg, protospacer) uniqueness, the ability to choose the positioning of cutting sites relative to homology arms, insert sequences and markers, and the ability to handle and use very large sequences in compatible vector formats by confining cutting inside target cells to produce recombinogenic substrates. Beneficially, reliance on PCR (which can introduce sequence errors, eg, in retrieved sequences) is avoided. Furthermore, sequences retrieved using certain configurations of the invention are retrieved to produce vectors that are ready for further use. In many downstream applications, such as. In subsequent recombineering to produce modified sequences, in genetic engineering of cells, for gene therapy of cells or organisms (eg, humans, mice, plants, yeast or bacteria) etc.

Furthermore, sequence retrieval is not limited to a specific cell type, such as yeast cells as is necessary with prior techniques such as Transformation-associated recombination (TAR). TAR relies upon processes outside a cell for extraction and preparation of cellular DNA for introduction of fragments into linear TAR vectors prior to transformation into yeast cells. Genomic fragment generation (by shearing of genomic DNA) outside cells is also a feature of the CATCH method of Jiang at al 2015 (infra). That method must be performed with a DNA shearing step outside a cell. In a protective gel medium followed by. In vitro Gibson assembly of fragments into vectors. Unlike these prior methods, the invention in some configurations advantageously is performed inside the protective environment of a cell for generation of recombinogenic ends and sequence retrieval into vectors that may be ready for further use, and additionally shearing and the need to control this is not a feature of these invention configurations. In aspects of the invention, vectors can be advantageously constructed by creating recombinogenic nucleic acid ends. In situ in a cell which enables in-cell capture of large genomic fragments (eg, of the order of 100-250 kb or up to 1 Mb such as in a YAC) directly into nascently-linearised circular vectors (such as BACs and YACs) that can accommodate such insert sizes. Advantageously, in embodiments this enables the direct creation of circular (eg, closed circular, eg, supercoiled) vectors with large inserts that are very useful for downstream procedures such as introduction into target cells for insertion of some or all of the retrieved sequence into the genome or an episome of the target cell. For this purpose, it is useful that retrieved sequences in vectors of the invention may be flanked by homology arms that can be readily used for homologous recombination insertion of the retrieved sequence into the target cell genome.

Homologous recombination is initiated with recombinogenic (free) ends produced by cutting DNA. The cut ends enhance efficiency, as the skilled addressee will know. The invention usefully focuses cutting (eg, Cas cutting) to a site in a first strand which can be pre-designed (Ie, engineered), rather than a site already existing in the host cell genome. The first strand can be in a vector such as a BAC or plasmid or phage, in an example. This allows pre-engineering of the first strand so that the location and the nature of the protospacer/PAM combination or other cutting motif can be precisely chosen and predetermined prior to carrying out the homologous recombination with a second or donor strand, eg, a strand of a chromosome or episome of a cell. In an example, the location of cutting for subsequent homologous recombination is known and can be controlled relative to the location of other desired elements (eg, promoters, selection markers, lox sites etc) in the first strand or vector (eg, FIGS. 2A, 3A, 3B, 5A, 6A, 8A and 9A). This therefore provides an advantage over using sites already existing in the host cell genome, as the latter dictates the nature and location of the cutting motifs or protospacers and the nature of the associated (cognate) PAMs. In that case, the choice of nuclease is dictated by the nature of the available cutting motif, eg, Cas is dictated by the nature of an acceptable PAM (or vice versa), whereas. In the present invention the choice of motif/nuclease (eg, PAM/Cas combination) can be freely made as engineering of the first strand prior to carrying out the method allows for this. Furthermore, by choosing or designing a predetermined protospacer PS1 (and optionally PS2), the invention allows targeting of the homologous recombination to any desired region of the host cell genome (rather than being dictated by pre-existing host cell sites). In the present invention, by designing and including one or more homology arms (HA1, HA2) for use with the predetermined cutting motif (eg, protospacer/PAM combination(s)) in the vector (rather than in the target nucleic acid) there is a freer choice of homology sequence in the target nucleic acid, which means that the location of homologous recombination in the target can be controlled and more freely selected. In prior methods, the need to carefully select unique protospacer sites, appropriate PAMs and matching Cas severely restricts and dictates the choices for precise location of cutting and homologous recombination with the target strand. This is not desirable when wanting to choose a precise location in a host cell genome to be modified (eg, for gene therapy of an organism or modification of a human cell for therapy)—that precise location may not have appropriate protospacer/PAM combinations or other cutting motif for use. The invention instead avoids these problems by moving these choices to the design of the first strand instead. Thus, by purposeful design of the first strand, the invention can provide more flexibility in choosing locations to be modified in the host cell strand and can provide for more flexibility for the choice of Cas or other nuclease to be used. Additionally, close siting of cut, recombinogenic ends next to homology arm sequence can be achieved and controlled, and positioning of vector marker or insert sequence relative to cut ends can be pre-determined in order to allow for detectable deletions from and insertions into the vector during the in situ homologous recombination method inside a cell or In vitro (see, eg, FIGS. 5A, 56, 6B and 8A). The invention also provides the possibility to create new markers that indicate correct cutting for homologous recombination in situ (see, eg, FIG. 5A). This may be useful for recombineering methods, In an example.

Figure 4A:
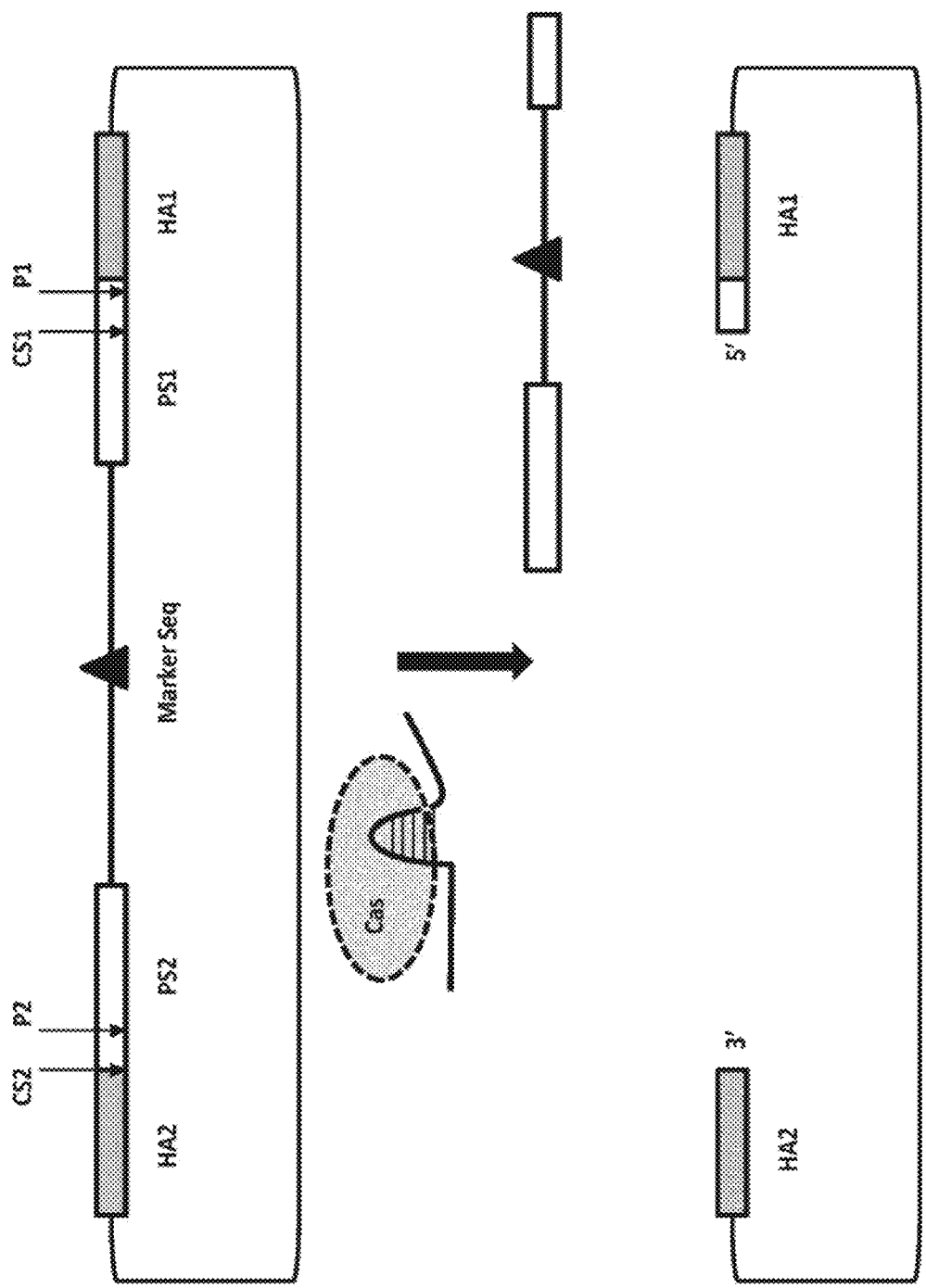
FIG. 4A shows release of a marker fragment to produce two recombinogenic ends in a retrieval vector.
Figure 4B:
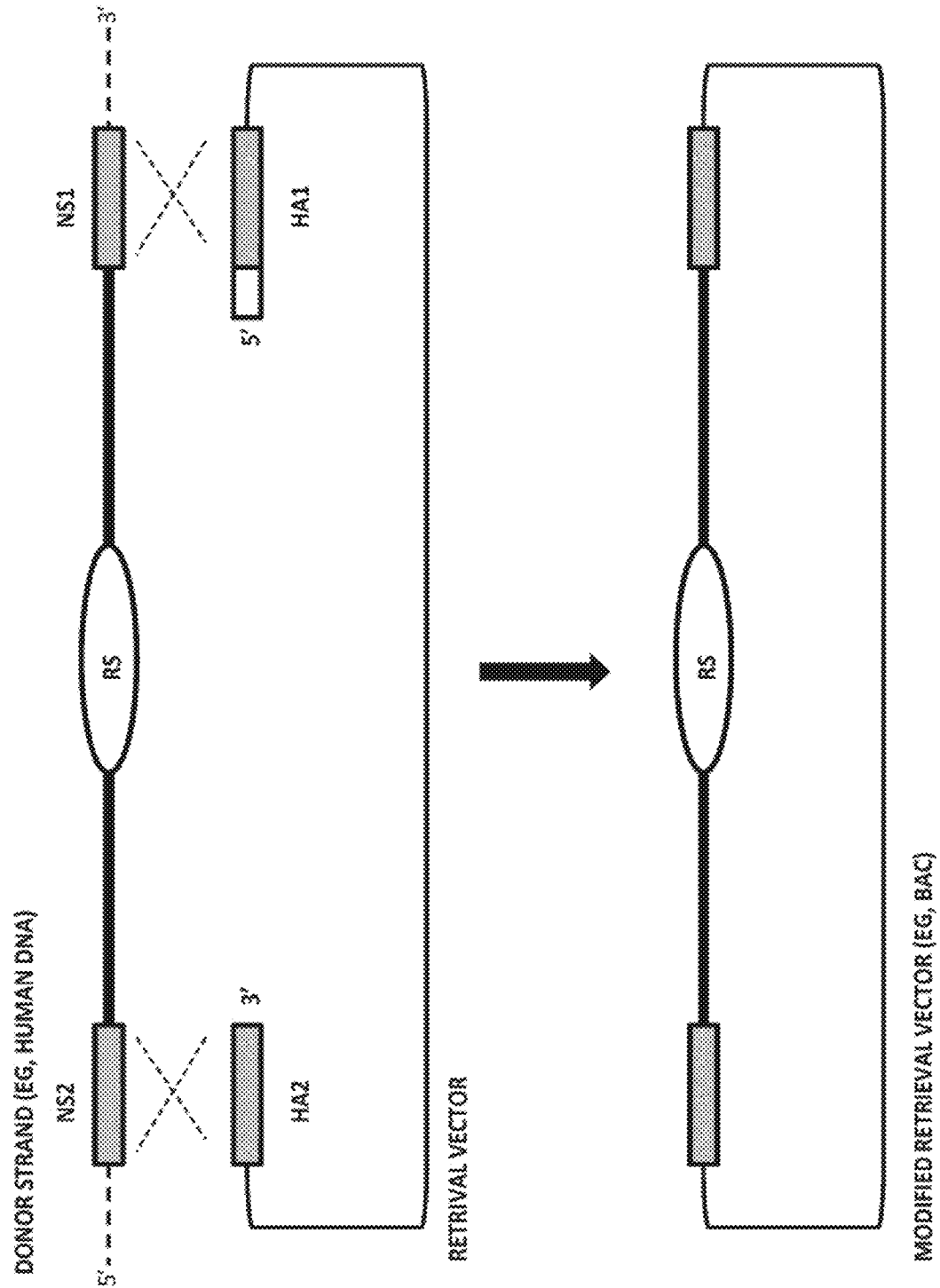
Figure 4C:
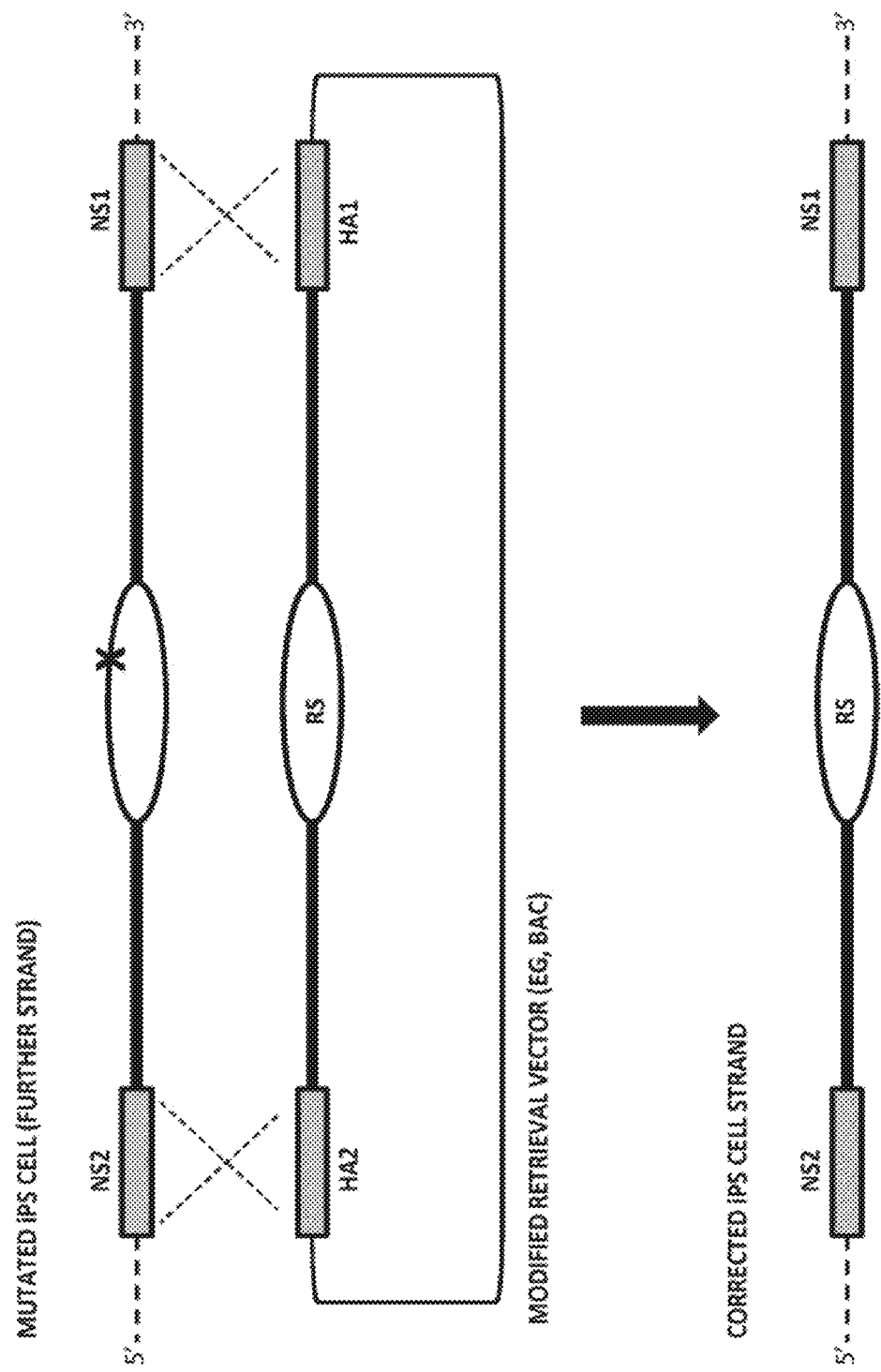
Figure 4D:
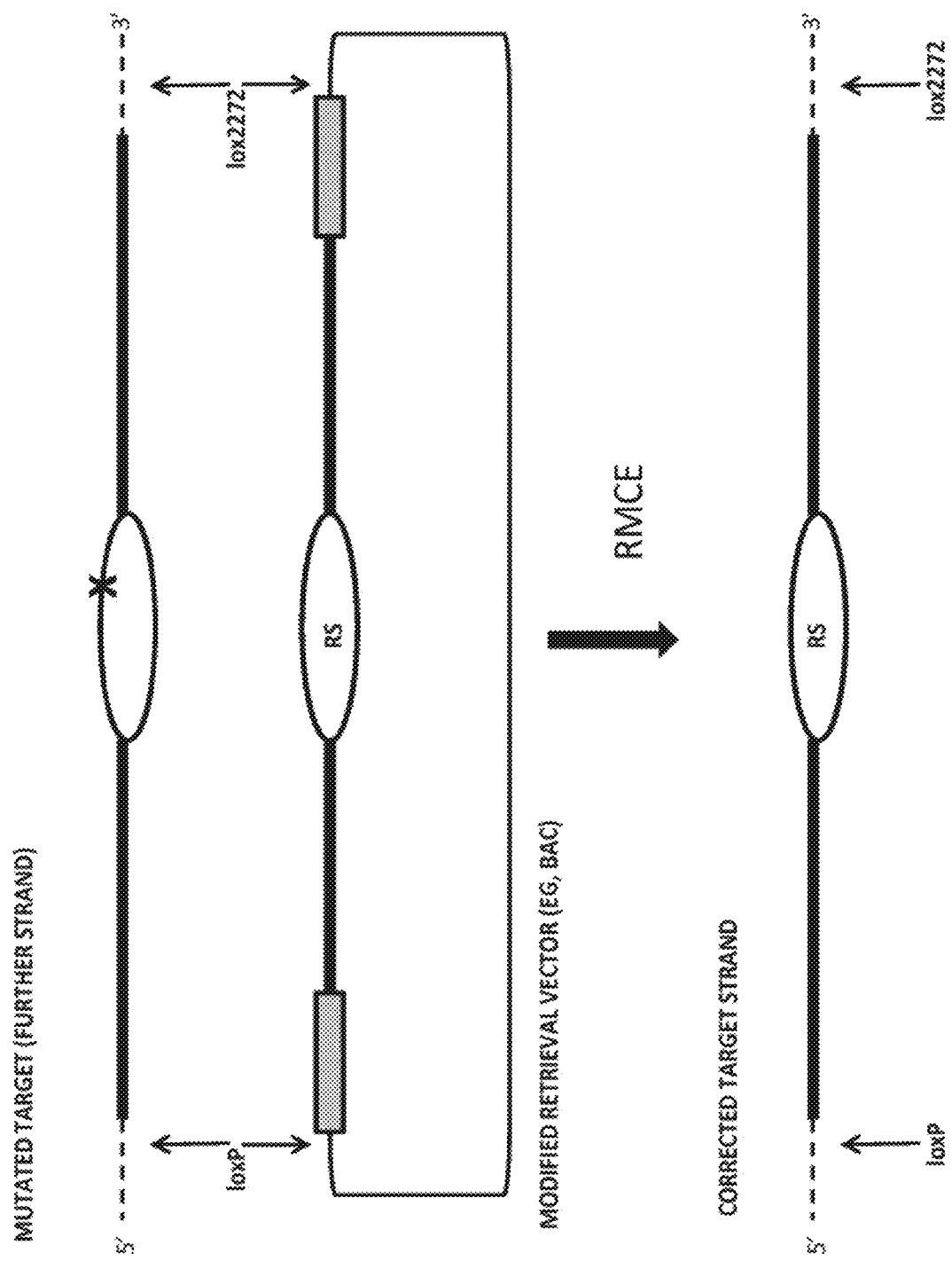
Figure 5A:
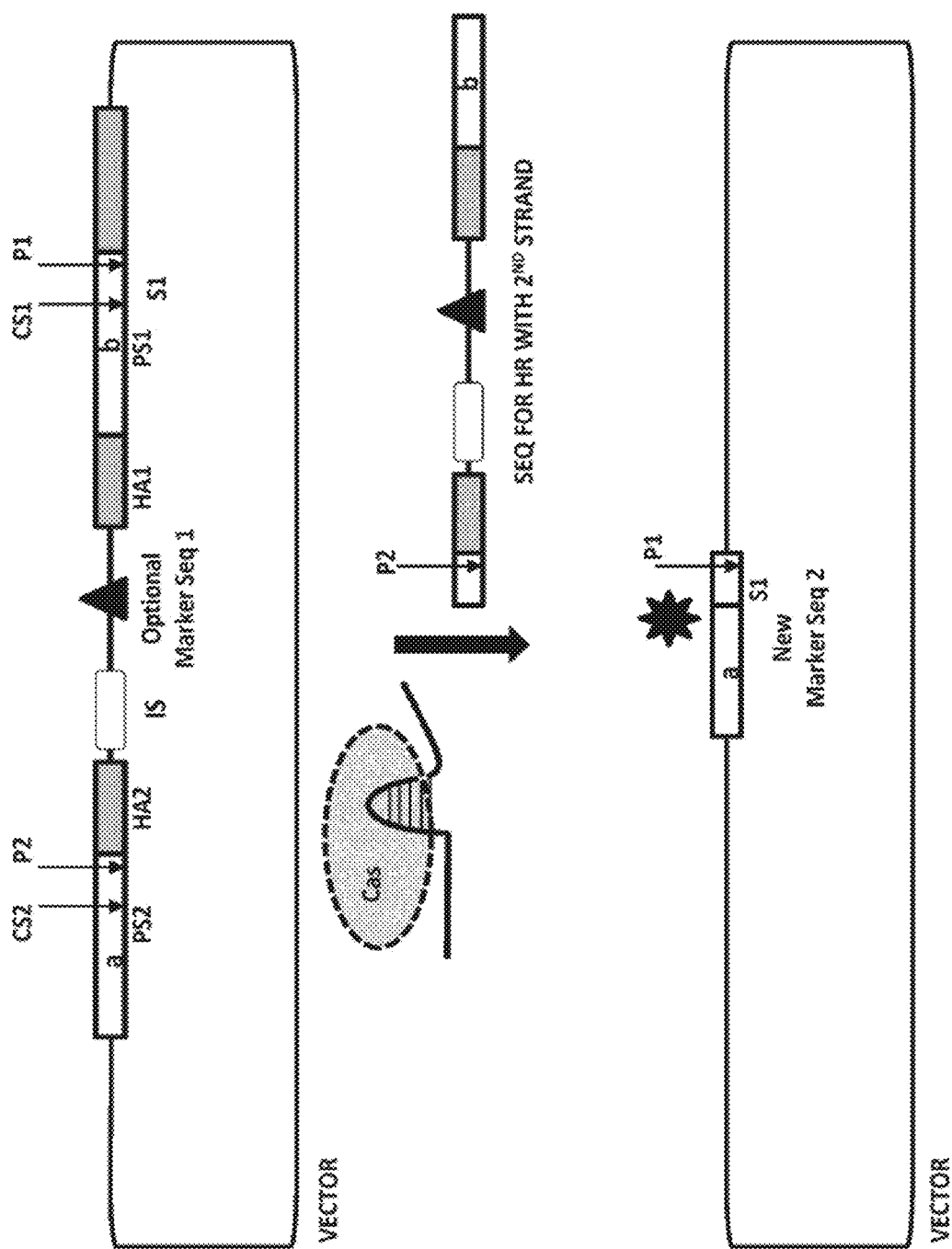
FIG. 5A shows the release of a recombinogenic nucleic acid fragment that can be used in a subsequent process of HR with a target (FIG. 5B) for insertion of an insert sequence (eg, a regulatory element or exon sequence).

Usefully, the invention also provides for the possibility of sequence retrieval from a donor or target strand to the first strand, eg, in a vector (see, eg, FIG. 4B). This is useful for retrieving sequence for further modification in the context of a vector, eg, in methods of recombineering and/or producing vectors for subsequent use in modifying further target strands or cells. In an example, this is useful in a subsequent method of homologous recombination insertion of retrieved sequence into a target strand (eg, FIG. 4C) or in a method using cre-lox sites engineered into the product first strand (such as flanking the retrieved insert) for subsequent cre-lox insertion of retrieved sequence into a target strand or cell genome (eg, FIG. 4D). The retrieved sequence in the first strand is used, In an example in a subsequent method of cell modification (eg, for human, animal or plant gene therapy). In an alternative, the invention provides the possibility to use cutting (eg, Cas cutting) of the first strand to release a recombinogenic nucleic acid for subsequent homologous recombination or site-specific recombination (eg, using lox sites, eg, RMCE using incompatible lox sites) with a target strand for insertion of sequence into the target strand (see, eg, FIGS. 5A & 5B) or deletion of sequence from the target strand (see, eg, FIG. 5C). As shown in FIG. 5A, release of the recombinogenic strand can create a new first strand marker sequence (eg, detectable by PCR or expressing a detectable marker).

Thus, in one embodiment, the invention provides the further steps of using the sequence inserted into the first strand in a method of homologous recombination or site-specific recombination (eg, using cre-lox) for modifying a target nucleic acid strand or genome of a target cell (eg, a prokaryotic, eukaryotic, plant, animal or human cell). In one example, some or all of the insert sequence is used to replace or insert sequence in the target (with or without concomitant deletion of target sequence) or to delete sequence in the target. The method optionally comprises isolating or sequencing the product target strand or modified nucleic acid comprised by the target cell. In an example, the insertion or replacement changes 1, 2, 3, 4, 5, 6, 7, 8, 9 or 10 nucleotides or codons in the target nucleic acid strand. In an example, this method renders the target strand sequence (eg, a gene comprised by the target strand) active, inactive, or increases the activity or decreases the activity thereof (eg, wherein the activity is the expression of a protein encoded by the gene. In an example, this corrects a genetic defect in the target (eg, for human cell gene therapy).

In an example, the invention further comprises using the product first strand in a method of recombineering to produce a further strand comprising all or part of the donor sequence that was inserted into the first strand in step (d). Optionally, the method comprises using the further strand product in a method of homologous or site-specific recombination modification of a target cell genome, and optionally isolating the product target cell and/or administering the target cell to a human or animal subject for medical use and/or culturing a population of such target cells and isolating the population or a sample thereof. In an example, a sequence is retrieved from a donor strand (eg, from a human cell chromosome DNA of a human subject), the retrieved sequence being in a product first strand. This retrieved sequence is then modified by genetic engineering (eg, recombineering or mutation, eg, to correct an undesirable mutation in the retrieved sequence). This produces a further strand. A sequence of this strand, wherein the sequence comprises the modification (eg, mutation correction) is then inserted into a strand of a target cell (eg, into a DNA strand of a chromosome of a human cell, eg, a cell of a different human or from the human subject, eg, wherein the cell is of the same or a different type to the first cell). In an example, the retrieved sequence is isolated from a first cell of a human subject, the method used. In vitro to correct a genetic defect in the retrieved sequence, and the correction is inserted into an PS cell derived from the same human subject to produce an iPS cell comprising the genetic correction (an optionally where the genetic defect has been deleted in the genome of the IPS cell). Optionally, the IPS cell is cultured to produce a population of iPS cells or a population of differentiated cells for human therapy (eg, a tissue for human therapy). The therapy is, In an example, therapy of said human subject. In this way, gene therapy can be performed in which the method enables ex vivo precise correction of a genetic defect (eg, a single nucleotide polymorphism, SNP) without the need to use human DNA sequence from different human (eg, using a human BAC source where the sequence may have unknown or unwanted changes versus the human subject genome). The invention, therefore, is for therapy of the human subject without introducing DNA mutation or sequence of another human. This is useful for precise and highly conservative genetic changes for human gene therapy of a human subject. The invention provides any of the product strands, vectors, populations or cells herein for any and all of these purposes.

In an example, the correction is the correction of one, two or three or more SNPs in a gene (eg, in an exon and/or regulatory sequence of a gene) In the human subject for gene therapy of the subject. In an alterative, the subject is a non-human animal (eg, rodent, mouse or rat). In an alternative, the subject is a plant or yeast. In an alternative, the subject is an insect. In an alternative, the subject is a bacterium or protozoan.

The invention enables precise small and large deletions by modification of a target strand in a homologous recombination step that deletes sequence from the target strand. This is useful. In an example, to inactivate genes or regulatory sequences in the target strand (eg, for modifying a host cell comprising the donor strand, such as when the donor strand is chromosomal or episomal, eg, comprised by a plasmid). In an example, a defective sequence can be deleted from the genome of such a host cell. In another example, the cell can be killed or its growth or proliferation inhibited by the modification, eg, wherein the cell is a prokaryotic cell, such as a human pathogen cell. An example is a bacterial cell, eg, *E. coli, S. aureus, P. aeruginosa, S. pyogenes, S. thermophilus* or another bacterial cell disclosed herein. In an example, the cell is a plant, yeast, mammalian, human, rodent, prokaryotic, eukaryotic, bacterial or arhcaeal cell wherein the method is used to replace a host cell sequence with a sequence from the first strand. Optionally, donor sequence is retrieved (inserted into) the first strand. The first strand can be comprised by a vector, such a BAC, PAC, YAC or plasmid.

In an example, the first strand is comprised by a vector selected from bacterial artificial chromosome (BAG), yeast artificial chromosome (BAC), PAC and a plasmid and the retrieved sequence is inserted into the vector. The product vector comprises, optionally, a first Cas nuclease cutting site at the 5' end of the retrieved sequence, or flanking 5' of said end and/or a Cas nuclease cutting site at the 3' end of the retrieved sequence, or flanking 3' of said end. Optionally, both cutting sites are present and the Cas sites are cognate to the same Cas nuclease (eg, a Cas9). The invention provides any such vector obtained or obtainable by a method of the invention. The invention provides a method of the invention for producing a library (eg, a BAC library) of said vectors, wherein the vectors are obtained or obtainable by a method of the invention. In an example, the or each retrieved sequence is a human sequence, eg, from the same or different (such as 2, 3 or 4) human genomes. In an example, the different human genomes are genomes of humans of the same ethnic population as defined by the 1000 Genomes project (eg, in an example, the different human genomes are genomes of humans of the different ethnic population as defined by the 1000 Genomes project). In an example, the ethnic population is selected from 1-14, eg, number 3, 4 or 9:—

1=ASW; 2=CEU; 3=CHB; 4=CHS; 5=CLM; 6=FIN; 7=GBR; 8=IBS; 9=JPT; 10=LWK; 11=MXL; 12=PUR; 13=TSI; 14=YRI.

In an example, the invention provides such a vector (eg, BAC) library. The inclusion of the Cas cutting site(s) facilitates generation of recombinogenic nucleic acid with one or two free ends as per the invention for subsequent homologous recombination with a further strand as described herein. In an example, when the library comprises human retrieved sequences, the recombinogenic nucleic acid can be used to modify a human or non-human animal cell, by insertion of retrieved human sequence into the genome of the cell (optionally to concomitantly replace a sequence of the cell genome). In an example, the human cell is an PS cell. In an example, the cell is a rodent, mouse or rat cell. The invention provides such a cell obtained or obtainable by this method, eg, for human or animal therapy. The invention provides a tissue developed from such a cell obtained or obtainable by this method, eg, for human or animal therapy, wherein the cell is a pluripotent, multipotent or totipotent cell (eg, a human or animal iPS cell), wherein the tissue is not a human or comprised by a human.

In an example of any method of the invention, up to 300, 200, 100, 75, 50, 25, 15, 10, 5 or 1 kb of strand DNA (eg, as contiguous sequence) is inserted into the first strand and/or further strand. The insertion(s) can be in multiple steps (eg, each step according to a method of the invention). In an example, the method comprises multiple insertions of DNA into the first and/or further strand, wherein up to 3 Mb, 2 Mb, 1 Mb or 900, 800, 700, 600, 500, 400, 300, 200, 100, 50, 25, 15, 10, 5 or 1 kb of retrieved DNA (eg, as contiguous sequence) is inserted into the or each strand. The invention provides such a product first or further strand or a cell comprising this. In addition or alternatively, no more than 3 Mb, 2 Mb, 1 Mb or 900, 800, 700, 600, 500, 400, 300 kb is inserted.

In an example of any method of the invention, up to 300, 200, 100, 75, 50, 25, 15, 10, 5 or 1 kb of first strand DNA (eg, as contiguous sequence) is inserted into the donor strand (with or without sequence retrieval into the first strand). In an example, additionally or alternatively up to 300, 200, 100, 50, 75, 25, 15, 10, 5 or 1 kb of donor strand DNA (eg, as contiguous sequence) is inserted into the first strand. The insertion(s) can be in multiple steps (eg, each step according to a method of the invention). In an example, the method comprises multiple insertions of first strand DNA into the donor strand, wherein up to 3 Mb, 2 Mb, 1 Mb or 900, 800, 700, 600, 500, 400, 300, 200, 100, 50, 25, 15, 10, 5 or 1 kb of first strand DNA (eg, as contiguous sequence) is inserted into the donor strand. The invention provides such a product donor strand or host cell comprising this. In addition or alternatively, no more than 3 Mb, 2 Mb, 1 Mb or 900, 800, 700, 600, 500, 400, 300 kb is inserted.

In an example of any method of the invention, up to 3 Mb, 2 Mb, 1 Mb or 900, 800, 700, 600, 500, 400, 300, 200, 100, 50, 25, 15, 10, 5 or 1 kb of first strand DNA (eg, as contiguous sequence) Is deleted. In an example, additionally or alternatively up to 3 Mb, 2 Mb, 1 Mb or 900, 800, 700, 600, 500, 400, 300, 200, 100, 50, 25, 15, 10, 5 or 1 kb of donor or further strand DNA (eg, as contiguous sequence) is deleted. The invention provides such a product donor strand or host cell comprising this. The deletion(s) can be in multiple steps (eg, each step according to a method of the invention). In an example, deletion from, and insertion into, the first strand are simultaneous. In an example, deletion from, and insertion into, the donor strand are simultaneous. In an example, deletion from, and insertion into, the further strand are simultaneous. In addition or alternatively, no more than 3 Mb, 2 Mb, 1 Mb or 900, 800, 700, 600, 500, 400, 300 kb is deleted.

The invention provides the possibility to include one or more sequences for producing guide RNA(s) in situ. The sequences can encode single guide RNA(s) (ie, chimaeric gRNAs) or cRNA(s) that combine with tracrRNA(s) to produce gRNA(s). The gRNA(s) or tracrRNA(s) are, in an example, encoded by one or more sequences comprised by the first strand (eg, a first vector comprising the strand) or comprised by a different nucleic acid (eg, a second vector) (see, eg, FIGS. 8A & 8B). Alternatively, the tracrRNA(s) are encoded by a target cell into which the first strand is introduced for Cas cutting inside the cell. In this case the target cell comprises an endogenous CRISPR/Cas system (eg, is an eukaryotic or prokaryotic cell that has been engineered to comprise such a system or is a bacterial or archaeal cell that naturally comprises such a system) and the tracrRNA is the endogenous tracrRNA.

The Cas nuclease(s) (eg, Cas9 or Cas3) can be introduced into a target cell (or mixed in vitro with the first nucleic acid) or can be encoded by sequence(s) comprised by the first strand (or first vector) or another nucleic acid (eg, a second vector) that is introduced into the target cell or combined. In vitro with the first strand and the guideRNA(s) or sequence(s) encoding these (see, eg, FIGS. 8A & 8B). In an alternative, the target cell comprises an endogenous CRISPR/Cas system and the Cas is the endogenous Cas nuclease (eg, Cas9 or Cas3). In an alternative, instead of Cas cutting, the invention uses cpf1 cutting and cognate sites and the disclosure herein applies mutatis mutandis to cpf1 instead of Cas.

A further advantage of the invention is the possibility to construct a universal precursor vector which is useful for adapting to produce bespoke vectors. The universal vector can be designed to include one or more cloning sites for insertion of homology arm(s) that are selected to target a desired and predetermined area of a target cell genome or target nucleic acid. The universal vector is provided with one or more cutting sites (eg, Cas nuclease cutting sites), each flanking or immediately adjacent to a respective site ("cloning site") for insertion of a homology arm. In this way, the positioning of recombinogenic ends can be controlled relative to homology arm(s) for subsequent homologous recombination. Positioning relative to SSR sites (eg, lox sites) in the vector can be controlled for subsequent use in cre-lox insertion of sequences into further or second strands as described herein. As shown in FIGS. 9A-E, each cloning site can, In an example be a restriction endonucleases site (eg, EcoR1, BamH1 or other site) or a SSR site (eg, a loxP, lox211, lox2272, frt or other site). As shown, a method of the invention comprises providing such a universal precursor vector and combining a homology arm into the vector adjacent a Cas nuclease site. In one embodiment, the arm is comprised by a nucleic acid that has been cut by a restriction endonuclease, wherein the endonuclease has also been used to cut a cloning site of the precursor vector, wherein the cut sites are recombined to insert the arm into the vector, thereby producing a vector comprising a first strand for use in a method of the invention. In an alternative, compatible SSR sites in a cloning site of the precursor vector and in a nucleic acid comprising the arm are used for site-specific recombination which inserts the arm into the vector adjacent or flanking a Cas nuclease site, thereby producing a vector comprising a first strand for use in a method of the invention.

In a further application of the universal precursor vector concept of the invention, there is provided a method of producing a collection of first vectors, wherein each vector comprises a first strand for use in a method of the invention. In this production method, a plurality of precursor vectors are combined with a plurality of nucleic acids, each comprising a respective homology arm, wherein the method comprises cloning the homology arms into the vectors, wherein each product vector comprises at least one said homology arm adjacent or flanking a cutting (eg, Cas nuclease) site, thereby producing a collection of vectors, each comprising a first strand for use in a method of the invention. In an example, each of the nucleic acids is cut with the same restriction endonucleases, wherein a cloning site of the precursor vectors is cut with the same endonucleases, wherein the homology arms are inserted into the precursor vectors by recombining cut sites in the precursor vectors with the cut nucleic acids. In an alternative, SSR recombination is used to insert the arms into compatible SSR sites in the precursor vectors. In an example, the nucleic acids are obtained by cutting genomic DNA of a first cell (eg, whole genome DNA, or DNA of one or more chromosomes or episomes of the cell), wherein the cutting is with said restriction endonucleases, thereby producing a population of cut nucleic acids that are combined with a plurality of precursor vectors that have cloning sites cut with the same endonucleases, wherein a plurality of cut nucleic acid sequences are inserted into a plurality of precursor vectors to produce a collection of product vectors, each comprising a said first strand for use in a method of the invention. This is useful for retrieving many different genomic sequences of a cell, or different sequences of a target nucleic acid, wherein retrieved sequences can act as homology arms in product vectors, for use in the invention, eg, for retrieval of further sequences from cells (eg, of the same type as the first cell(s) or from a different species or from a different member of the species, eg, the first cell is a cell of a first human subject and the retrieved sequence is from a cell of a different human subject or the same human subject). Additionally or alternatively, the product vectors comprise insert sequence(s) adjacent or flanking retrieved sequences, wherein the retrieved sequences are used as homology arms for inserting the insert sequence(s) into a further nucleic acid strand or a target cell genome or episome. This enables one to insert at multiple sites in one cell or a population of cells, In an example, to determine the various effects of the inserted sequence in the cell or cells of the population. This can be used, eg, to find one or more sites in a target cell genome that is desirable for expression of an insert sequence (eg, a foreign gene sequence). In an example, the target cell is a prokaryotic (eg, bacterial) or yeast cell, and the method may be useful for generating a cell population for industrial or lab manufacture of the product of the insert sequence. In another example, the target cell is a eukaryotic cell (eg, a human cell, eg, CHO or HEK293 or Cos cell), and the method may be useful for generating a cell population for industrial or lab manufacture of the product of the insert sequence. The invention includes a method of producing such a prokaryotic or eukaryotic cell for expression of the product of the insert sequence, wherein the method comprises expressing the product of the insert sequence and optionally isolating the product. The invention comprises the product for use in any industry disclosed herein, eg, for medical use or for medicine, cosmetic, food, environmental, beverage, water or petrochemical production or treatment.

Each nucleic acid (eg, first strand or vector) that is introduced into a cell as per the invention may comprise one or more nuclear localisation signals (NLSs), as is conventionally known, to localise to the cell nucleus.

In an embodiment, one or more nucleotide sequences is inserted into the genome (eg, into a chromosome or episome) of the cell. The inserted sequences then can act as bait sites, ie, sequences that are homologous to, and hybridise to respective vector (first strand) homology arms in the method of the invention. For example, N1 and/or N2 can be sequences that have been inserted into the cell genome and these are homologous to HA1 and HA2 respectively.

Insertion of the bait sites can be effected using any available method, such as SSR insertion using one or more site-specific recombination sites (eg, lox or frt sites) flanking each bait sequence. One or more bait sites may be randomly inserted (which then enables retrieval of random (non-predetermined) RS sequences from donor strands or insertion of IS or RS into random sites in the recipient cell genome, eg, to assess the effect of the inserted sequence at different locations in a plurality of recipient cells. In an embodiment, each bait nucleotide sequence is flanked by long terminal repeats (LTRs) of a transposon (eg, flanked by piggyBac or Sleeping Beauty LTRs) and the resulting nucleic acid is introduced into the cell using an expressed respective tranposase for random and optionally multiple insertion of copies of the bait sequence in the cell genome. In an example, a nucleotide sequence comprising in 5' to 3' order: a transposon LTR, NS1, optional spacer sequence, NS2 and LTR of the same transposon type is introduced into the cell and the NS1/NS2 combination is inserted into the cell genome ready for subsequent HR with homology arms of a strand or vector of the invention. In this way, RS or any other sequence flanked by appropriate homology arms can be inserted into the cell genome using the NS1/NS2 bait sequences. In an example only a single type of bait sequence (a NS1 or NS2, for example) is inserted in the cell genome and this is used in a RS retrieval method of the invention using a vector (first strand) that comprises a homologous HA (eg, a one-arm strand or vector). Use of bait sequences of predetermined sequence is advantageous as a sequence can be chosen or designed that is not found in the original cell genome, which reduces the chances of HR events with the strand or vector of the invention at genomic sites that are unintended. For example, the cell is a eukaryotic cell (eg, a human, rodent, mouse or rat cell) and the bait sequence is a bacterial or viral sequence.

Thus the invention provides the following embodiments:—

1. A method of retrieving a nucleic acid sequence from a donor nucleic acid strand, the method comprising
    (a) providing a nucleic acid vector comprising a first nucleic acid strand, wherein the first strand comprises:—
        i. a first homology arm (HA1) that is homologous to a first nucleotide sequence (NS1) of the donor strand for homologous recombination between the strands:
        ii. a second homology arm (HA2) that is homologous to a second nucleotide sequence (NS2) of the donor strand for homologous recombination between the strands; and
iii. an intervening nucleotide sequence joining the 3' end of HA1 to the 5' end or HA2;
wherein HA1 is 5' to HA2 in the first strand; and NS1 is 3' of NS2 in the donor strand,
wherein the donor strand comprises a retrieval sequence (RS) between NS1 and NS2;
(b) combining the first strand with the donor strand;
(c) cutting (eg, nuclease or Cas nuclease cutting) of a first cut site (CS1) of the first strand at the 5' end of HA1, or flanking 5' of said end; and/or Cas nuclease cutting of a second cut site (CS2) of the first strand at the 3' end of HA2, or flanking 3' of said end;
wherein steps (b) and (c) are carried out in any order or simultaneously;
(d) carrying out homologous recombination of the cut first strand with the donor strand, whereby gap repair of the first strand produces a vector in which RS is retrieved between HA1 and HA2; and
(e) optionally isolating or sequencing the vector or the RS sequence thereof.

In an alternative, step (d) uses SSR (not HR).

In an example, the cutting is performed using Cas, eg a Cas9.

In an alternative, embodiment 1 provides:—

1a. A method of modifying a nucleic acid sequence, the method comprising
(a) providing a nucleic acid vector comprising a first nucleic acid strand, wherein the first strand comprises:—
i. a first homology arm (HA1) that is homologous to a first nucleotide sequence (NS1) of a further nucleic acid strand for homologous recombination between the strands;
ii. a second homology arm (HA2) that is homologous to a second nucleotide sequence (NS2) of the donor strand for homologous recombination between the strands; and
iii. an intervening sequence (IS) joining the 3' end of HA1 to the 5' end of HA2;
wherein HA2 is 5' to HA1 in the first strand; and NS2 is 5' of NS1 in the further strand,
wherein the further strand optionally comprises a sequence (DS) between NS1 and NS2;
(b) combining the first strand with the further strand;
(c) cutting (eg, using Cas nuclease cutting) of a cut site (CS3) of the first strand at the 3' end of HA1, or flanking 3' of said end; and/or Gas nuclease cutting of a cut site (CS4) of the first strand at the 5' end of HA2, or flanking 5' of said end;
wherein steps (b) and (c) are carried out in any order or simultaneously;
(d) carrying out homologous recombination or site-specific recombination of the first strand with the further strand, whereby a product further strand is produced in which IS is inserted between NS1 and NS2 and optionally DS is deleted from the further strand; and
(e) optionally isolating or sequencing after (d) the vector, the product further strand or IS thereof.
Optionally in method 1a the first strand is not cut at both CS1 and CS2.

References to embodiment 1 herein, are alternatively to read as references to embodiment 1a.

In an example, a Cas used herein is a Cas9, optionally *S. pyogenes* or *S. aureus* Cas9. In an example, HA1 is identical (or at least 90 or 95% identical to) to the sequence of NS1 and/or HA2 is identical (or at least 90 or 95% identical to) to the sequence of NS2.

Herein, in any configuration of the invention, the first strand, vector or any other strand or vector herein may optionally comprise one or more nuclear localisation signal sequences, NLSs (eg, when the method is carried out in a eukaryotic cell). For example, the Cas nucleotide sequence, gRNA-encoding sequence or IS sequence can comprise one or more NLSs.

When CS1 is at the 5' end of HA1, or flanking 5' of said end, it is meant that CS1 Is immediately adjacent to the 5' end of HA1 (ie, cutting (eg, Cas cutting) is immediately 5' of the first (5'-most) nucleotide of HA1); or cutting (eg, Cas cutting) is on the 5' side of the first nucleotide of HA1 (eg, separated from the end by no more than 1 kb or 500, 250, 200, 150, 50, 25, 20, 10 or 5 nucleotides 5' of the end). When CS2 is at the 3' end of HA2, or flanking 3' of said end, it is meant that CS2 is immediately adjacent to the 3' end of HA2 (ie, cutting (eg, Cas cutting) is immediately 3' of the last (3'-most) nucleotide of HA2); or cutting (eg, Cas cutting) is on the 3' side of the last nucleotide of HA2 (eg, separated from the end by no more than 1 kb or 500, 250, 200, 150, 50, 25, 20, 10 or 5 nucleotides 3' of the end).

When CS3 is at the 3' end of HA1, or flanking 3' of said end, it is meant that CS3 is immediately adjacent to the 3' end of HA1 (ie, cutting (eg. Cas cutting) is immediately 3' of the first (3'-most) nucleotide of HA1); or cutting (eg, Cas cutting) is on the 3' side of the last nucleotide of HA1 (eg, separated from the end by no more than 1 kb or 500, 250, 200, 150, 50, 25, 20, 10 or 5 nucleotides 3' of the end). When CS4 is at the 5' end of HA2, or flanking 5' of said end, it is meant that CS4 is immediately adjacent to the 5' end of HA2 (ie, cutting (eg, Cas cutting) is immediately 5' of the first (5'-most) nucleotide of HA2); or cutting (eg, Cas cutting) is on the 5' side of the first nucleotide of HA2 (eg, separated from the end by no more than 1 kb or 500, 250, 200, 150, 50, 25, 20, 10 or 5 nucleotides 5' of the end).

The concepts of "at" and "flanking" ends herein are to be similarly construed.

The method, optionally comprises using a cutting site motif to direct cutting (eg, Cas, meganuclease-, zinc finger protein-mediated or TALEN-mediated cutting) of the donor or further strand before said homologous recombination (HR), wherein the HR is carried out with cut first and donor/further strands. Optionally, the motif is destroyed by the homologous recombination (eg, a protospacer and/or PAM in the donor or further strand that was used for cutting the donor strand is destroyed).

The method, optionally comprises using a respective cutting site motif to direct each cutting (eg, Cas, meganuclease-, zinc finger protein-mediated or TALEN-mediated cutting or restriction endonucleases cutting) of the first strand or retrieval vector before said homologous recombination (HR) retrieval of the RS, wherein the motif is destroyed by the homologous recombination (eg, a protospacer and/or PAM in the donor or further strand that was used for cutting the first strand or vector is destroyed).

In an example, the inserted nucleic acid sequence in the first strand product is flanked (eg, added after the HR step of embodiment 1) on one or both sides by a site-specific recombination (SSR) site (eg, loxP or incompatible lox sites, eg, loxP and lox511 or loxP and lox2272—this enables recombinase mediated cassette exchange (RMCE) to be used with the incompatible lox sites so that the insert sequence can be subsequently inserted into a further nucleic acid strand (eg, a chromosome of a target cell) by RMCE with matching SSR sites in the target (see, eg, FIG. 4D). Thus, in an example, the invention further comprises using this first strand product in a is method of site-specific recombination with a target nucleic acid strand (eg, comprised by a chromosome or episome of a target cell, eg, a human, bacterial, plant, yeast or rodent cell, eg, in vitro), wherein the insert sequence between the site-specific sites is inserted into the target nucleic acid strand by recombination with compatible SSR sites in the target nucleic acid.

In an example, the cell comprising the donor or further strand and/or a target cell is a human cell (eg, in vitro). In an example, the cell is a lymphocytic cell, a B-cell or a T-cell (eg, a human cell). In one embodiment, a method of the invention is used to modify a human T-cell, eg, by inserting and/or deleting DNA into the genome of the T-cell, eg, by inserting one or more DNA sequences for producing an antigen receptor in the product T-cell. The invention provides such a T-cell product obtained or obtainable by this method. Optionally, the method comprises isolating the T-cell or a progeny thereof, and optionally administering the cell or progeny (or a population thereof) to a human subject for treating or preventing a disease or condition (eg, a cancer or autoimmune disease or condition). In an example, the invention provides a cell (eg, T-cell or B-cell) product obtained or obtainable by the method of the invention for treating or preventing a disease or condition (eg, a cancer or autoimmune disease or condition). In an example, the invention provides such a cell or progeny thereof or population thereof when comprised by a medicament for treating or preventing a disease or condition (eg, a cancer or autoimmune disease or condition).

In an example the cell comprising the donor or further strand and/or a target cell is a cell of a bacterial species or strain (eg, that is a human or animal pathogen or comprised by a foodstuff, beverage, petrochemical substance or in an environment (eg, waterway) or industrial water store). In an example, the cell is a bacterial cell of a human or animal microbiome species or strain (eg, a human or animal gut, oral, vaginal, skin or armpit microbiome species or strain). In an example, the invention provides the product cell (or progeny thereof) of the method for treating or preventing a disease or condition in a human or animal mediated by said bacterial strain or species. In an example, the invention provides the method for treating or preventing an infection of a human or animal with bacteria of a species or strain that is a human or animal pathogen, or bacteria of a human or animal microbiome species or strain (eg, a human or animal gut, oral, vaginal, skin or armpit microbiome species or strain). In an example, the invention provides the method for killing or inhibiting growth or proliferation of bacteria in a foodstuff, beverage, petrochemical substance or in an environment (eg, waterway) or industrial water store).

2. The method of embodiment 1, wherein steps (b) to (d) are performed in a host cell; optionally wherein the donor strand is a strand of a chromosome or episome of the cell.

In an example, the cell is a eukaryotic cell (eg, a human, non-human animal, yeast or plant cell).

In an example, the method is carried out in a human (eg, wherein the method is a cosmetic method), embryo (eg, non-human embryo), zygote (eg, non-human zygote), germ cell (eg, human or non-human germ cell) or non-human animal.

In an example, the method is carried out. In vitro. In an example, the method is carried out in vivo (eg, but not in a human or human embryo).

For use in the invention, vector(s) can be introduced into cell(s), eg, by injection or electroporation, or by cell fusion.

3. The method of embodiment 2, wherein the vector is circular in step (a) and the circular vector is introduced into the cell in step (b).

4. The method of embodiment 1, 2 or 3, wherein the first, donor or further (eg, the first strand) strand is comprised by a BAC.

For example, the donor strand is comprised by a BAC and wherein RS is a human or rodent (eg, mouse) sequence of said BAC.

5. The method of any preceding embodiment, wherein the vector is circular in step (a) and/or wherein the product of step (d) is a circular vector.

This aspect is advantageous to accommodate large (>10 kb) or very large (>100 kb) IS or RS in the vector. This avoids the problems known in the art of handling and purifying large linear nucleic fragments for HR or SSR, as this embodiment of the invention produces recombinogenic linear substrates in situ for HR; earlier or later handling steps (such as combining strands or introducing the first strand into a target cell) are, however, carried out with circular substrates which facilitate use of larger retrieval fragments or insertion of larger fragments. Furthermore, circular vectors are useful for the present invention as they are taken up readily by cells, for performance of the methods of the invention in a cell. In an example, the vector is a closed circular vector (eg, a supercoiled closed circular vector). The inventor realised that this is very efficiently taken up by cells. Supercoiled DNA transforms *E. coli* at least a hundred-fold better than relaxed open-circular DNA.

6. The method of any preceding embodiment, wherein the vector is a BAC, YAC, PAC, plasmid or cosmid; optionally wherein the donor strand is comprised by a BAC, YAC. PAC, cosmid or plasmid.

Reference Is made to Nucleic Acids Res. 2000 Sep. 1; 28(17): e81; PMCID: PMC110718; Massimo Cocchia et al for details about the recovery and potential utility of YACs as circular YACs/BACs. In an example, the vector of the invention is a circular YAC that comprises an IS or RS of up to 250, 500 or 670 kb.

In an example, the vector is a circular BAC that comprises an IS or RS of up to 250 or 300 kb.

7. The method of any preceding embodiment, wherein RS or IS is at least 1 kb in length.

8. The method of embodiment 7, wherein RS or IS is at least 10 kb in length.

9. The method of embodiment 7, wherein RS or IS is at least 100 kb in length.

For example, RS is at least 1, 10, 100, 200, 300, 400, 500, 600, 700, 800 or 900 kb or 1 Mb in length and the product of step (d) Is a closed circular vector comprising RS. For example, IS is at least 1, 10, 100, 200, 300, 400, 500, 600, 700, 800 or 900 kb or 1 Mb in length and the vector of step (a) is a closed circular vector comprising IS.

10. The method of any preceding embodiment, wherein CS1 or CS3 is no more than 250 nt (ie, 250 contiguous nucleotides) from HA1.

The term "nt" refers to contiguous nucleotides.

11. The method of any preceding embodiment, wherein CS2 or CS4 is no more than 250 nt from HA2.

12. The method of any preceding embodiment, wherein each of HA1 and HA2 is at least 15 nt in length.

In an example, HA1 is at least 50, 100, 150, 200, 300, 400, 500, 600, 700, 800 or 900 nt in length, or at least 1, 2, 3, 4, 5, 6, 7, 8, 9, 10, 20, 30, 50 or 100 kb in length. In an example, HA2 is at least 50, 100, 150, 200, 300, 400, 500, 600, 700, 800 or 900 nt in length, or at least 1, 2, 3, 4, 5, 6, 7, 8, 9, 10, 20, 30, 50 or 100 kb. In length.

13. The method of any preceding embodiment, wherein HA1 and HA2 comprise a total length of at least 0.2 kb. In an example, HA1 and HA2 comprise or consist of a total length of at least 0.2, 0.3, 0.4, 0.5, 0.6, 0.7, 0.8, 0.9, 1, 2, 3, 4, 5, 6, 7, 8, 9, 10, 20, 30, 50 or 100 kb in length.

14. The method of any preceding embodiment, wherein HA1 and HA2 are isogenic (ie, are 100% Identical nucleotide sequences) to NS1 and NS2 respectively.

In an embodiment, HA1 and HA2 are each at least 80, 85, 90 or 95% identical to the nucleotide sequences of NS1 and NS2 respectively.

15. The method of any preceding embodiment, wherein the Cas cutting, retrieval of RS into the first strand, or insertion of IS into the further strand deletes or inactivates a marker sequence from the first strand or vector (eg, a sequence for expression of a first detectable marker), optionally wherein the method comprises detecting the deletion of the marker sequence (eg, absence of a detectable marker that is encoded by the marker sequence).

Examples of markers (eg, when the method is carried out in a cell) are antibiotic resistance markers, eg, neo, hygromycin, kanamycin, chlormaphenicol, puromycin (eg, puro-deltaTK) resistance etc as will be known to the skilled addressee. In an example, the marker is a sequence that is created by the method of the invention, wherein the marker sequence is in the product of the method but not present in the starting strands of the method. Thus, the marker sequence is detectable by PCR, eg, junction PCR.

In an example, the marker sequence is a HPRT sequence and the method is carried out inside a cell. Cells deficient in HPRT are selected by resistance to 6-thioguanine (6-TG). Thus, in this example deletion or inactivation of the HPRT sequence by RS insertion into the first strand or IS deletion from the first strand (and insertion into the further strand) can be selected as the resulting cell is resistant to 6-TG. Another example is a tk sequence for expressing thymidine kinase, explained further below.

16. The method of any preceding embodiment, wherein the first strand or vector comprises a marker sequence (eg, for expression of a second detectable marker) which is not deleted by the method; and optionally the method comprises after step (d) detecting the presence of the marker sequence (or expression product thereof) with or without detection of the absence of the marker sequence (or expression product) (eg, HPRT sequence) that was deleted by the method of embodiment 15.

NeoR, HygR and PuroR are widely used as markers. In mammalian and other cells. Cells carrying the resistance sequence can be determined by administration of G418 (resistance conferred by NeoR sequence), hygromycin (resistance conferred by HygR sequence) or puromycin (resistance conferred by PuroR sequence). Thus, in one example, the marker. In this embodiment number 16 is selected from NeoR, HygR and PuroR.

Appropriate selection agents for use in the present invention, therefore, are:—

G418: An aminoglycoside antibiotic similar to gentamycin. Toxic to bacteria, yeast, higher plant and mammalian cells in addition to protozoans and helminths.

Hygromycin: An aminoglycoside antibiotic that inhibits protein synthesis in bacteria, fungi and higher eukaryotes.

Puromycin: A broad spectrum antibiotic that inhibits protein synthesis in both prokaryotic and eukaryotic organisms.

In an example, the method comprises using positive-negative selection marker detection to determine that RS has been inserted into the first strand or IS has been deleted from the first strand. In this example, the method is carried out in cells and cells that have undergone the method survive the negative selection agent and grow in the presence of the positive agent (eg, antibiotic resistance, such as an antibiotic resistance mentioned above). The gancyclovir will kill any cell that contains the thymidine kinase (tk) sequence. So the method of the invention can be performed in cells and the first strands comprise tk for expressing thymidine kinase as the marker according to the embodiment 15 above. Cells undergoing successful homologous recombination or SSR in the method of the invention are grown in antibiotic to select for recombination and gancyclovir to kill any cells that didn't successfully undergo recombination according to the method (le, tk sequence retained).

17. The method of any preceding embodiment, wherein in step (a) the vector comprises (in 5' to 3' direction):—
   A. A first protospacer sequence (PS1) comprising CS1;
   B. A first PAM (P1) adjacent to the 3' end of PS1: and
   C. HA1;
wherein a seed sequence (S1) of PS1 joins CS1 to P1; and optionally wherein HA1 comprises S1 and P1.

18. The method of any preceding embodiment, wherein in step (a) the vector comprises (in 5' to 3' direction):—
   D. HA2;
   E. A second protospacer sequence (PS2) comprising CS2;
   F. A second PAM (P2) adjacent to the 3' end of PS2;
wherein a seed sequence (S2) of PS2 joins CS2 to P2; and optionally wherein the remainder of PS2 is at the 3' end of HA2.

In any configuration of the invention herein, each protospacer (eg, PS1 or PS2) consists of 15 to contiguous nucleotides, eg, 18, 19, 20, 21, 22, 23, 24 or 25 contiguous nucleotides. For example, PS1 consists of 18-21 nucleotides, eg, 20 nucleotides. For example, PS2 consists of 18-21 nucleotides, eg, 20 nucleotides. In any configuration of the invention herein, each seed sequence (eg, S1 or S2) consists of 2 to 15 contiguous nucleotides, eg, 12, 11, 10, 9, 8, 7, 6, 5, 4, 3 or 2 contiguous nucleotides. For example, S1 consists of 5-12 or 8-12 nucleotides, eg, 12 nucleotides. For example, S2 consists of 5-12 or 8-12 nucleotides, eg, 12 nucleotides.

In any configuration of the invention herein, each PAM (eg, P1 or P2) is 2, 3, 4 or 5 contiguous nucleotides. The choice of PAM matches the Cas to be used for cutting, as the skilled addressee knows. In an example, the PAM is any PAM disclosed herein.

In any configuration of the invention herein, each Cas cutting site is for example 2-5, eg, 2, 3, 4 or 5 nucleotides immediately 5' of the cognate PAM. For example, CS1 is 3 or 4 nucleotides 5' of P1. For example, CS2 is 3 or 4 nucleotides 5' of P2.
19. The method of any preceding embodiment, wherein the same nuclease (eg, Cas nuclease (eg, a Cas9)) is used to cut CS1 and CS2.
20. The method of any preceding embodiment, wherein the same guide RNA (gRNA1) is used to guide Cas cutting of CS1 and CS2.
   In an example, P1 and P2 consist of the same PAM sequence, CS1 Is the same number of nucleotides 5' of P1 as CS2 is 5' of P2. Additionally or alternatively, PS1 consists of the same sequence as PS2. Additionally or alternatively, S1 consists of the same sequence as S2. In an example, the sequence of PS1 to (and including) P1 is the same as the sequence of PS2 to (and including) P2, and optionally P1 and P2 are cognate to the same Cas9.
   The term "cognate to" or "cognate with" or similar will be readily understood to the skilled person. For example the PAM NGG functions with *S. pyogenes* Cas9, and thus this PAM is cognate to *S. pyogenes* Cas9.
21. The method of embodiment 20 when dependent upon embodiment 18, wherein said remainder of PS2 is comprised by NS2 (eg, at the 3' end of NS2) or is adjacent NS2 in the donor strand (eg, adjacent the 3' end of NS2 or flanking 3' of said end).
22. The method of any preceding embodiment, wherein NS1 and NS2 are not at or adjacent protospacer/PAM sites recognised by the Cas nuclease(s) used in step (c).
   Thus, in the method the donor or further strand is not cut by the Cas nuclease(s). In an alternative embodiment, the donor or further strand is cut by the Cas nuclease(s). This is useful for HR.
23. The method of any one of embodiments 1 to 21, wherein before or during step (d) the donor or further strand is cut at the 5' end of NS2 or flanking 5' of said end; and/or at the 3' end of NS1 or flanking 3' of said end.
24. The method of any preceding embodiment, further comprising inserting all or part of said RS of the product vector into a further nucleic acid strand; optionally wherein the product vector is a closed circular vector and the vector is cut (eg, using Cas) outside the RS (eg, outside HA1 and HA2) and/or the further strand is cut (eg, using Cas) before the RS is inserted into the further strand.
   For example, the further strand is cut as defined in embodiment 23.
25. The method of embodiment 24, wherein RS sequence is inserted into the further strand using HA1 and/or HA2 in homologous recombination with said further strand; optionally wherein said further strand comprises NS1 and NS2 or sequences each at least 80, 90 or 95% Identical (or 100% Identical) to NS1 and NS2.
26. The method of embodiment 25, wherein the further strand is comprised by a cell and the vector product of step (d) (eg, a closed circular vector or supercoiled vector) is inserted into the cell before said homologous recombination.
27. The method of embodiment 24, 25 or 26, wherein said further strand is comprised by a stem cell, eg, an induced pluripotent stem cell (iPS cell) (eg, a human iPS cell in vitro); an immune cell (eg, T- or B-cell); an embryonic stem cell (eg, a mouse or rat ES cell); optionally wherein the method comprises developing the stem cell product into tissue or a non-human organism (eg, a mouse or rat).
   For example, the stem cell is a pluripotent, multipotent or totipotent stem cell. In an example, the stem cell is non-human and in vitro.
28. The method of any one of embodiments 24 to 27 for gene therapy, wherein a mutation of the further strand is removed by said homologous recombination insertion of RS into the further strand; the method optionally comprising isolating or sequencing the further strand product or RS in said product.
   In an example, the gene therapy is therapy of a human, animal, plant or yeast cell. In another example, the therapy is therapy of a human, animal or plant.
29. The method of any one of embodiments 24 to 28 (eg, when dependent from embodiment 1 using HR in step (d)) for correcting a genetic mutation. In vitro in a target human cell or progeny thereof, wherein the cell or progeny comprises said further strand, wherein the further strand comprises said genetic mutation, the method comprising
   (i) obtaining a second human cell (eg, a progeny or ancestor of the target cell, eg, cultured cells from the same culture) and carrying out the method of any one of embodiments 1 to 24 inside the second cell, wherein RS in the product vector of step (d) comprises said genetic defect;
   (ii) using genetic engineering (eg, recombineering) to correct the defect, thereby producing a product vector comprising a corrected RS sequence;
   (iii) inserting the corrected RS sequence (eg, by inserting the corrected product vector, such as a closed circular or supercoiled vector) into the uncorrected target cell or an uncorrected progeny thereof (eg, an PS cell), wherein the corrected RS sequence supplements or replaces the uncorrected RS sequence, thereby producing a corrected target cell or progeny thereof; and
   (iv) optionally culturing the corrected cell or developing tissue from the corrected cell.
30. The method of embodiment 29, wherein the method uses homologous recombination of the uncorrected RS sequence. In the target cell or progeny with HA1 and/or HA2 flanking the corrected RS sequence, thereby replacing the uncorrected RS sequence; optionally wherein the uncorrected and corrected RS sequences differ only by the corrected mutation(s).
31. The method of embodiment 29 or 30, wherein in step (iii) a closed circular corrected product vector is inserted Into the target cell or progeny; optionally wherein the corrected RS is at least 10 or 100 kb in length.
   Optionally, the corrected RS is up to 300 kb and/or the vector is a SAC.
32. The method of any one of embodiments 29 to 31, wherein the cells are cells of the same human subject and optionally the same cell type (eg, adult stem cells or cord blood stem cells from the same human subject).
33. A corrected cell, corrected vector or corrected RS sequence as recited in any one of embodiments 29 to 32 for treating a genetic defect in a human.
   In an example, the method provides a method of medically treating a human subject, the method comprising administering to the subject the corrected cell or progeny (eg, an IPS cell) or tissue developed therefrom, whereby a medical treatment in the subject is obtained.

34. The method of any one of embodiments 24 to 32, wherein the further strand is comprised by an immune cell, eg, a T- or B-cell (eg, a human cell); optionally wherein RS in the further strand encodes an antigen receptor or chain or domain thereof (eg, a T-cell receptor or a B-cell receptor, eg, a chimaeric antigen receptor or component thereof).
35. The method of any one of embodiments 1 to 32 and 34 for producing a Chimaeric Antigen Receptor T-cell (CAR-T cell) (eg, a human CAR-T cell).
36. The method of any one of embodiments 1 to 35, wherein the first vector is an adenoviral vector.
37. The method of embodiment 24, 25 or 26, wherein the further strand is comprised by an adenoviral vector.
38. The method of any one of embodiments 1 to 26, wherein the method is a recombineering method.
   In an example, the method is carried out in a bacterial cell (eg, an *E. coli* cell) in vitro.
39. The method of any preceding embodiment, comprising administering the vector product, strand product or cell product or RS product to a human or animal subject to treat or prevent a disease or condition in the subject; or a vector product, nucleic acid strand product or cell product or RS product obtainable by the method of any preceding embodiment for administration to a human or animal subject to treat or prevent a disease or condition in the subject.
40. The method of any preceding embodiment, wherein in step (b) and/or (d) the vector is a closed circular vector.
   For example, the vector is a covalently closed circular vector, which is optionally supercoiled. In an example, the method is carried out in a cell and in step (b) the cell is combined with a plurality of said vectors. In an example, the plurality comprises a plurality of said closed circular vectors, wherein one or more of said circular vectors is introduced into the cell. In an example, the vector or vectors are introduced into the cell by injection, electroporation or cell fusion.
41. The method of embodiment 40, wherein in step (b) the vector is supercoiled.
   This is particularly useful for efficient transformation of cells in the invention, wherein large (>10 kb) or very large (>100 kb) RS or IS are retrieved or inserted in the method.
42. The method of any preceding embodiment, wherein sequence between HA1 and HA2 (eg, between the 3' end of HA2 and the 5' end of HA1, eg, when the vector is circular in step (a)) is deleted from the first strand and/or sequence between NS1 and NS2 is deleted from the donor or further strand.
43. The method of embodiment 42 when dependent from embodiment 1, wherein RS is deleted from the donor strand.
44. The method of any preceding embodiment when dependent from embodiment 1, wherein a protospacer/PAM combination at the 5' end of HA1 or flanking 5' of said end is destroyed by step (d), eg. PS1 sequence is deleted, whereby PS1 is rendered non-functional in the first strand.
   This is useful for locking-in the changes produced by the method, as is the next embodiment.
45. The method of any preceding embodiment when dependent from embodiment 1, wherein a protospacer/PAM combination at the 3' end of HA2 or flanking 3' of said end is destroyed by step (d), eg, PS2 sequence and/or P2 is deleted, whereby PS2 is rendered non-functional in the first strand.
46. The method of any preceding embodiment, wherein donor or further strand sequence is inserted into the first strand and/or sequence (eg, IS) is deleted from the first strand, to form a new protospacer/PAM combination (eg, between the 3' end of HA2 and the 5' end of HA1 when the vector is circular in step (d) of embodiment 1) or a new marker sequence.
47. The method of embodiment 46 when dependent from embodiment 1, wherein a donor strand sequence is inserted immediately 5' of CS1 and the donor sequence and PS1 sequence together form a new protospacer adjacent P1 (or form a new marker sequence for detection that said homologous recombination has taken place); and/or donor sequence is inserted immediately 3' of CS2 and the donor sequence and PS2 sequence together form a new protospacer (or form a new marker sequence for detection that said homologous recombination has taken place).
   The new marker can be, for example, an antibiotic resistance marker sequence as disclosed herein. Optionally the method comprises detecting the presence of the new marker sequence or the expression product thereof.
48. The method of embodiment 46 or 47 comprising Cas cutting the protospacer of the new combination after step (d), eg, for subsequent insertion of a further sequence into the first strand or for carrying out the method of any one of embodiments 24 to 32 and 34 to 37; the method optionally comprising cutting the protospacer of the new combination using a Cas nuclease that is different from the Cas used in step (c); or the method comprising detecting said new maker(s).
49. The method of any preceding embodiment, wherein donor sequence is deleted from the donor or further strand to form a new protospacer/PAM combination (eg, between the 3' end of NS2 and the 5' end of NS1) or a new marker sequence.
50. The method of embodiment 49, wherein sequence of the new protospacer/PAM sequence or marker are comprised by nucleotide sequences (NS3 and NS4) found in the donor or further strand before step (d) and the new protospacer/PAM combination or marker sequence is formed after deletion of a donor sequence (eg, RS) or further strand sequence in step (d) and joining of NS3 to NS4.
51. The method of embodiment 49 or 50 comprising Cas cutting the protospacer of the new combination in the donor or further strand after step (d), eg, for subsequent insertion or deletion of a further sequence into or from the donor or further strand; the method optionally comprising cutting the protospacer of the new combination in the donor or further strand using a Cas nuclease that is different from the Cas used in step (c); or the method comprising detecting said new maker. In the donor strand.
52. The method of embodiment 51, wherein before step (d) NS3 is flanking 5' of the donor or further strand sequence to be deleted, and wherein NS4 is flanking 3' of the donor or further sequence to be deleted, wherein in step (d) the sequence is deleted and the 3' end of NS3 is joined to the 5' end of NS4, thereby forming the new protospacer/PAM combination or marker sequence. In the donor or further strand.
   In an example, NS3 is immediately adjacent to the 5' end of the sequence to be deleted, or within 10 nucleotides 5' of said end. In an example, NS4 is immediately adjacent to the 3' end of the sequence to be deleted, or within 10 nucleotides 3' of said end.
53. The method of any preceding embodiment, the method comprising isolating or copying the modified donor or further strand or the region of donor or further nucleic acid sequence where deletion occurred.
For example, the isolating or copying uses PCR.
54. The method of any preceding embodiment, wherein RS or IS comprises or consists of a regulatory element, protein-encoding sequence, an exon or a marker sequence.
55. The method of any preceding embodiment when dependent on embodiment 1, wherein RS is inserted into the first strand in step (d) and the inserted sequence is functional for expression from the modified first strand, the method optionally comprising detecting the expression product of the inserted sequence.
56. The method of embodiment 55, wherein the inserted sequence is a protein-encoding sequence, an exon or a marker sequence that is inserted in functional arrangement with a first strand regulatory element, whereby the regulatory element is capable of controlling expression of the donor sequence from the modified first strand.
57. The method of any preceding embodiment, wherein the inserted sequence is a marker sequence, and the method comprises detecting the marker sequence in the modified first or further strand; or detecting the expressed marker, wherein the marker is not detectable before step (d).
58. The method of embodiment 2 or any preceding embodiment when dependent from embodiment 2, wherein RS is deleted from the donor strand and the deletion is lethal to the host cell.
59. The method of embodiment 2 or any preceding embodiment when dependent from embodiment 2, wherein the method down-regulates cell viability, growth or proliferation (eg, kills the cell).
60. The method of embodiment 2 or any one of embodiments 3 to 58 when dependent from embodiment 2, wherein the method up-regulates cell viability, growth or proliferation (eg, kills the cell).
61. The method of embodiment 2 or any preceding embodiment when dependent from embodiment 2, wherein the method is carried out in a bacterial or archaeal cell, eg, an *E. coli* cell.
62. The method of embodiment 61, wherein the cell is of a human pathogen species.
63. The method of embodiment 61 or 62, wherein the cell is a cell of a human microbiome species, eg, a human gut microbiome species.
64. The method of any one of embodiments 61 to 63, wherein the first strand is a bacteriophage nucleic acid strand, wherein the bacteriophage strand is introduced into the host cell by infecting the host cell with the bacteriophage.
65. The method of embodiment 2 or any preceding embodiment when dependent from embodiment 2, wherein the cell comprises an endogenous CRISPR/Cas system and wherein endogenous host Cas is used to cut in step (c).
66. The method of embodiment 2 or any preceding embodiment when dependent from embodiment 2, wherein the method is carried out without introducing exogenous Cas or a sequence encoding exogenous Cas Into the cell.
67. The method of embodiment 2 or any preceding embodiment when dependent from embodiment 2, wherein the method is carried out in cells to kill a population of prokaryotic cells, wherein the cells are of the same species or strain.
This is useful as an antibiod method, eg, for treatment, removal or prevention of a population of bacteria in a human, animal, foodstuff, beverage, cosmetic, petrochemical or environmental substance (eg, soil or water or aqueous fluid).
68. The method of embodiment 67, wherein the population is comprised by a mixed population of prokaryotic (eg, bacterial) cells and the method selectively kills some but not all cells in the mixed population, wherein the killed cells are cells in which the first strand was introduced and CS1 and/or CS2 cut by a Cas.
69. The method of embodiment 67 or 68, wherein PS1 and P1 are cognate to a Cas nuclease (eg, an endogenous Cas) of the cells that are killed, but not cognate to cells in the population that are not killed, wherein CS1 is selectively cut in the cells that are killed; and/or wherein PS2 and P2 are cognate to a Cas nuclease (eg, an endogenous Cas) of the cells that are killed, but not cognate to cells in the population that are not killed, wherein CS2 is selectively cut in the cells that are killed
70. The method of any one of embodiments 67 to 69, comprising isolating the product population or a sample of said product.
71. The method of any preceding embodiment, wherein the donor strand, cell or population is comprised by a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor).
72. The method of any preceding embodiment, wherein step (c) comprises exposing the first strand to a guide RNA (gRNA1, eg, a single gRNA) that hybridises to PS1 to guide the Cas to cut PS1; optionally wherein step (c) comprises expressing gRNA1 or crRNA sequence thereof from a nucleotide sequence used (eg, as part of the first strand) In step (b); and/or wherein step (c) comprises exposing the first strand to gRNA1 or a second guide RNA (gRNA2, eg, a single gRNA) that hybridises to PS2 to guide the Cas to cut PS2; optionally wherein step (c) comprises expressing gRNA1 or gRNA2 or crRNA sequence thereof from a nucleotide sequence used (eg, as part of the first strand) in step (b);
73. The method of any preceding embodiment, wherein the first or each strand is a dsDNA.
For example, all of said strands (eg, first and donor, or first and further strands) are dsDNA strands.
74. The method of any preceding embodiment, wherein the first or each strand is a ssDNA.
For example, all of said strands (eg, first and donor, or first and further strands) are ssDNA strands.
75. The method of any preceding embodiment (eg, when carried out in a eukaryotic cell, eg, a human cell), wherein in step (c) Cas cutting is in protospacer sequence(s) (eg, PS1 and/or PS2) in the first strand wherein the protospacer comprises a seed sequence (eg, S1 or S2) wherein the seed sequence comprises a nucleotide sequence rare or not found in the cell genome.

This is useful to minimise the chances of off-site cutting elsewhere than in the desired location of the strands used in the method. Off-site cutting is to be avoided, eg, in human cell gene therapy. The invention realises the utility, therefore, of using prokaryotic sequences to direct Cas cutting in eukaryotic (eg, human or animal or plant or yeast) target cells. The invention thus provides further embodiments of this concept as follows.

76. The method of embodiment 75, wherein the seed sequence comprises a prokaryotic start codon, eg, GTG and/or TTG codon, and optionally the seed sequence does not comprise an ATG codon.
77. The method of embodiment 75 or 76, wherein the seed sequence comprises a Shine Dalgamo sequence, eg, the seed sequence comprises GAGG or AGGAGG.
78. The method of any preceding embodiment, wherein (eg, when carried out in a eukaryotic cell, eg, a human cell), wherein in step (c) Cas cutting is in protospacer sequence(s) that is optimised for prokaryotic (eg, *E. coli*), archaeal or viral use, or is not found in the cell genome.

This embodiment is based on the observation that sequences in prokaryotes etc are optimised (codon optimised) for use in those organisms, and thus sequence optimisation is different from that for eukaryotic use. This increases the chances of specificity of cutting when the method is performed in a eukaryotic (eg, human, eg, iPS) cell.

79. The method of embodiment 78, wherein the protospacer sequence (eg which is up to 25, 21 or 20 contiguous nucleotides) comprises a sequence of a bacterial Pribnow box; bacterial leader sequence (eg, Pel B); bacterial −10 sequence or bacterial −35 element sequence (eg, TATAAT or TTGACA); a bacterial upstream promoter element (UP element) sequence; bacterial regulatory or operon sequence; or a bacterial origin of replication sequence.
80. A method of making a first nucleic acid strand suitable for homologous recombination with a second nucleic acid strand, eg, in a method according to any preceding embodiment when dependent from embodiment 1, the method of making comprising:—
    (a) identifying first and second nucleotides sequences (NS1 and NS2) of the second strand, optionally wherein NS1 Is selected so that. It is 3' of NS2 in the second strand;
    (b) combining in another nucleic acid strand
        i. a first homology arm (HA1) complementary to first predetermined target nucleotide sequence NS1 of the second strand for homologous recombination between HA1 and NS1;
        ii. a second homology arm (HA2) complementary to second predetermined target nucleotide sequence NS2 of the second strand for homologous recombination between HA2 and NS2; and
        iii. a first protospacer sequence (PS1) adjacent a PAM (P1), wherein P1 is cognate to a first Cas nuclease for cutting PS1 at a first cut site (CS1), wherein CS1 is at the 5' end of HA1 or flanking 5' of said end; and/or a second protospacer sequence (PS2) adjacent a PAM (P2), wherein P2 is cognate to said first or a different Cas nuclease for cutting PS2 at a second cut site (CS2), wherein CS2 is at the 3' end of HA2 or flanking 3' of said end; whereby the first strand is produced.
81. The method of embodiment 80, wherein the first strand product is comprised by a closed circular vector, optionally wherein the vector is supercoiled.
82. The method of embodiment 80 or 81, wherein the first strand product is comprised by a vector that is a BAC, YAC, PAC, cosmid or plasmid.
83. The method of any one of embodiments 80 to 82, wherein CS1 is no more than 250 nt from said end of HA1.
    In an example, CS1 is no more than 3, 4, 5, 6, 7, 8, 9, 10, 20, 30, 40, 50, 60, 70, 80, 90, 100, 150, 200 or 250 nt from said end of HA1.
84. The method of any one of embodiments 80 to 83, wherein CS2 is no more than 250 nt from said end of HA2.
    In an example, CS1 is no more than 3, 4, 5, 6, 7, 8, 9, 10, 20, 30, 40, 50, 60, 70, 80, 90, 100, 150, 200 or 250 nt from said end of HA2.
85. The method of any one of embodiments 80 to 84, wherein each of HA1 and HA2 is at least 15 nt in length.
    In an example, HA1 Is at least 20, 30, 40, 50, 60, 70, 80, 90, 100, 150, 200, 250, 300, 400, 500, 600, 700, 800 or 900 nt, 1, 2, 3, 4, 5, 6, 7, 8, 9, 10, 50, 100, 200, 300, 400 or 500 kb in length. In an example, HA2 is at least 20, 30, 40, 50, 60, 70, 80, 90, 100, 150, 200, 250, 300, 400, 500, 600, 700, 800 or 900 nt, 1, 2, 3, 4, 5, 6, 7, 8, 9, 10, 50, 100, 200, 300, 400 or 500 kb in length.
86. The method of any one of embodiments 80 to 85, wherein HA1 and HA2 comprise a total length of at least 0.2 kb.
    In an example, HA1 and HA2 comprise or consist of a total length of at least 0.2, 0.3, 0.4, 0.5, 0.6, 0.7, 0.8, 0.9, 1, 2, 3, 4, 5, 6, 7, 8, 9, 10, 20, 30, 50 or 100 kb.
87. The method of any one of embodiments 80 to 86, wherein HA1 and HA2 are isogenic or at least 80, 90 or 95% identical to NS1 and NS2 respectively.
88. The method of any one of embodiments 80 to 87, wherein the first strand product comprises (in 5' to 3' direction):—
    G. A first protospacer sequence (PS1) comprising CS1;
    H. A first PAM (P1) adjacent to the 3' end of PS1; and
    I. HA1;
wherein a seed sequence (S1) of PS1 joins CS1 to P1; and optionally wherein HA1 comprises S1 and P1.
    And/or the first strand product comprises:—
    J. HA2;
    K. A second protospacer sequence (PS2) comprising CS2;
    L. A second PAM (P2) adjacent to the 3' end of PS2;
wherein a seed sequence (S2) of PS2 joins CS2 to P2; and optionally wherein the remainder of PS2 is at the 3' end of HA2.
89. The method of any one of embodiments 80 to 88, comprising providing in the first strand an expressible nucleotide sequence encoding said first Cas (eg, a Cas9); optionally wherein the first strand comprises (or the first strand is combined with a further strand that comprises) an expressible nucleotide sequence that encodes a gRNA (gRNA1 eg, a single gRNA) that is complementary to PS1; or the sequence encodes an expressible crRNA that forms gRNA1 in a host cell, optionally with a tracrRNA encoded by host cell sequence.

In an example, the tracrRNA is encoded by vector sequence, eg, by the first vector or another vector combined with the first vector (eg, co-transformed into a cell where the method is performed).

90. The method of any one of embodiments 80 to 89, the method comprising after step (b) Cas cutting CS1 and/or CS2, optionally with the same Cas nuclease.
91. The method of any one of embodiments 80 to 90, wherein the method is carried out in a cell, eg, a prokaryotic cell.
92. The method of embodiment 91, wherein the method comprises recombineering.
93. The method of any one of embodiments 80 to 92, wherein NS1 and NS2 flank a sequence of an essential gene, antibiotic resistance gene or virulence gene, eg of a prokaryotic cell.
    In an example, the prokaryotic cell is any prokaryotic cell (eg, human pathogen cell) described herein.
94. The method of embodiment 93, further producing an antibiotic composition or kit comprising the product of the method in combination with an antibiotic, wherein NS1 and NS2 flank a sequence of an antibiotic resistance gene (eg, of a said prokaryotic cell), wherein the antibiotic is the antibiotic combined with the nucleic acid.
95. The method of any one of embodiments 80 to 94, further including in the first strand (or on a further nucleic strand in addition to the first strand) a nucleotide sequence that encodes a guide RNA (gRNA1, eg, a single gRNA) that is complementary to PS1 and/or PS2, or the sequence encodes a crRNA that forms gRNA1 in the cell (optionally with a tracrRNA encoded by host cell sequence); and/or further including in the first strand (or on a further nucleic strand in addition to the first strand) a nucleotide sequence that encodes a second guide RNA (gRNA2, eg, a single gRNA) that is complementary to PS2 or the sequence encodes a crRNA that forms gRNA2 in the cell (optionally with a tracrRNA encoded by host cell sequence).
    In an example, the tracrRNA is encoded by vector sequence, eg, by the first vector or another vector combined with the first vector (eg, co-transformed into a cell where the method is performed).
96. The method of any one of embodiments 80 to 95, further comprising producing a composition comprising the first strand, composition or kit product of any one of embodiments 80 to 95, wherein the composition is an agricultural agent (eg, herbicide or fertiliser), a foodstuff, food ingredient or precursor ingredient; beverage; aqueous composition (eg, intended for human consumption); an industrial or environmental substance (eg, oil, petroleum product, soil or a waterway or reservoir; or for use with equipment for recovering or processing oil, petroleum product, soil, water, a foodstuff, foodstuff ingredient or precursor, or a beverage or beverage ingredient of precursor).
97. The method of any one of embodiments 80 to 95, further comprising producing a medicament comprising the first strand, composition or kit product of any one of embodiments 80 to 95 for treating and/or preventing a disease or condition in a human or non-human animal.
98. The method of any one of embodiments 80 to 97, step (b) comprising
    (i) obtaining a nucleic acid strand (eg, comprised by a BAC) comprising a cloned genomic sequence of a cell, the sequence comprising (in 5' to 3' direction) HA2 and HA1 and optionally a joining sequence (JS1) therebetween;
    (ii) obtaining a targeting sequence comprising (in 5' to 3' direction) a first homology box (HB2) and a second homology box (HB1); wherein the sequence of HB2 is identical to a sequence of HA2 or a sequence at the 5' end of JS1 or a sequence spanning HA2 and the 5' end of JS1; and wherein the sequence of HB1 is identical to a sequence of HA1 or a sequence at the 3' end of JS1 or a sequence spanning HA1 and the 3' end of JS1; wherein the targeting sequence comprises a joining sequence (JS2) joining the 5' end of HB1 to the 3' end of HB2; wherein JS2 comprises said PS1/P1/CS1 combination and/or said PS2/P2/CS2 combination, wherein CS1 is no more than 250 nt from the 5 end of HA1; and wherein CS2 is no more than 250 nt from the 3' end of HA2;
    (iii) carrying out homologous recombination (eg, using recombineering) between the nucleic acid strand of step (i) with the homology boxes of the targeting sequence, to produce a nucleic acid strand (first nucleic acid strand) comprising (in 5' to 3' direction)
        a. HA2, PS2 (comprising CS2), P2, PS1 (comprising CS1), P1 and HA1, optionally comprising a selectable marker sequence between CS1 and CS2;
        b. HA2, PS2 (comprising CS2), P2 and HA1; or
        c. HA2 PS1 (comprising CS1), P1 and HA1.
99. The method of embodiment 98 for producing a first strand or vector for gene therapy of a human cell or producing a CAR-T cell, wherein said cell is the cell of step (i) or a progeny or ancestor thereof; optionally wherein the method comprises carrying out the method of any one of embodiments 28 to 32, 34 and 35 to carry out said human cell gene therapy or to produce said CAR-T cell.
100. A first strand, vector, composition, medicament or kit obtainable by the method of any one of embodiments 80 to 99, optionally comprising a retrieved sequence (RS) or IS between HA1 and HA2, wherein RS is as defined in any one of embodiments 1 to 79, eg, for gene therapy of a human or animal or for treating or preventing a bacterial infection in a human or animal.
101. The first strand or vector of embodiment 100 for use in gene therapy of a human cell, the strand or vector comprising protospacer sequence(s) (eg, PS1 and/or PS2) in the first strand wherein the protospacer comprises a seed sequence (eg, S1 or S2) wherein the seed sequence comprises a nucleotide sequence rare or not found in human cell genome.
102. The first strand or vector of embodiment 101, wherein the seed sequence comprises a prokaryotic start codon, eg, GTG and/or TTG codon, and optionally the seed sequence does not comprise an ATG codon.
103. The first strand or vector of embodiment 101 or 102, wherein the seed sequence comprises a Shine Dalgarno sequence, eg, the seed sequence comprises GAGG or AGGAGG.
104. The first strand or vector of any one of embodiments 101 to 103, wherein the strand comprises protospacer sequence(s) (eg, PS1 and/or PS2) that is optimised for prokaryotic (eg, E. coli), archaeal or viral use, or is not found in human cell genome.
105. The first strand or vector of embodiment 104, wherein the protospacer sequence (eg which is up to 25 or 20 contiguous nucleotides) comprises a sequence of a bacterial Pribnow box; bacterial leader sequence (eg, Pei B); bacterial −10 sequence or bacterial −35 element sequence (eg, TATAAT or TTGACA); a bacterial upstream promoter element (UP element) sequence; bacterial regulatory or operon sequence; or a bacterial origin of replication sequence.

106. The first strand or vector of any one of embodiments 101 to 105 for gene therapy of a human or human cell (eg, in a method according to any one of embodiments 28 to 32) or for producing a Chimaeric Antigen Receptor T-cell (CAR-T cell) (eg, a human CAR-T cell) for administration to a human to treat or prevent a disease or condition in the human (eg, a cancer or autoimmune disease or condition).

107. A method of inhibiting viability, growth or proliferation of a prokaryotic host cell, the method comprising
   (e) providing a first vector comprising a protospacer sequence (PS1) adjacent a PAM (P1) that is cognate to a first Cas nuclease;
   (f) providing a toxin or toxin precursor; or a vector comprising a sequence encoding a toxin or toxin precursor, wherein the toxin is toxic to the prokaryotic cell;
   (g) combining the cell with the vector(s) wherein the vector(s) are introduced into the cell, and providing the toxin in the cell; and
   (h) using Cas nuclease cutting of PS1 of the first vector using the first Cas nuclease, wherein the cutting promotes toxin activity in the cell, whereby the cell is killed or cell growth or proliferation reduced.

In an example, the method of any configuration of the invention is not a therapeutic, prophylactic or diagnostic method practised on a human or animal body or embryo. In an example, the method is cosmetic method or method for producing or processing a cosmetic, medicament, foodstuff, beverage, water or a petrochemical.

108. The method of embodiment 107, wherein the first Cas is guided by a first guide RNA (gRNA1, eg, a single guide RNA) in the cell which hybridises to PS1, whereby the Cas cuts PS1.
   Optionally, the sequence encoding gRNA1 is comprised by a vector (eg, the first vector) that is introduced into the cell.

109. The method of embodiment 108, wherein the method comprises providing. In the cell before step (d) gRNA1 or a sequence for producing gRNA1 in the cell, wherein the sequence is comprised by the first or another vector introduced into the cell in step (c).
   In an example, the sequence encodes a crRNA or comprises an expressible CRISPR array.

110. The method of any one of embodiments 107 to 109, wherein the first Cas nuclease is endogenous to the cell.

111. A method of transforming a host cell, the method comprising
   (a) providing a first nucleic acid vector, the vector being in a first state comprising
      i. a protospacer sequence (PS1) adjacent a PAM (P1) that is cognate to a first Cas nuclease; and
      ii. a first nucleotide sequence comprising a first marker sequence for marking the first state of the vector;
   (b) combining the cell with the vector wherein the vector is introduced into the cell; and
   (c) using Cas nuclease cutting of PS1 of the first vector using the first Cas nuclease, wherein the cutting converts the vector to a second state in which the marker sequence is rendered non-functional or deleted; and
   (d) optionally detecting the second state by detecting that the marker is non-functional in the cell or deleted from the vector.

The marker sequence can be any marker sequence disclosed herein, eg, a tk or HPRT sequence.

112. The method of embodiment 111, wherein marker sequence is rendered non-functional or deleted by allowing the cut vector to undergo homologous recombination with a chromosomal or episomal nucleic acid of the cell.

113. The method of embodiment 112, wherein vector sequence is inserted into the host nucleic acid.

114. The method of embodiment 111 or 112, wherein a sequence of the host nucleic acid is inserted into the vector.

115. The method of embodiment 114, wherein PS1 and/or P1 is destroyed in the vector by insertion of the host sequence.

116. The method of any one of embodiments 111 to 115, wherein the marker sequence is Cas excised from the vector and the vector undergoes gap repair by homologous recombination insertion of a sequence of the host nucleic acid into the vector.

117. The method of any one of embodiments 107 to 116, wherein PS1 and/or P1 is destroyed in the vector by the cutting.

118. The method of any to any one of embodiments 107 to 116, wherein the method is carried out in one or more cells without introducing exogenous Cas or a sequence encoding exogenous Cas into the cells.
   For example, the cell is a prokaryotic cell as described herein, eg, a bacterial or archaeal or human pathogen or microbiome cell.

119. The method of any one of embodiments 107 to 118, wherein the method is carried out in a cell and PS1 and P1 are cognate to a Cas that is endogenous to the cell for carrying out the cutting of step.

120. The method of any one of embodiments 107 to 119, wherein the method is carried out in cells to kill a population of prokaryotic cells, wherein the cells are of the same species or strain.

121. The method of embodiment 120, wherein the population is comprised by a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor).

122. The method of embodiment 120 or 121, wherein the population is comprised by a mixed population of prokaryotic (eg, bacterial) cells and the method selectively kills some but not all cells in the mixed population, wherein the killed cells are cells in which the first vector or first strand was introduced and PS1 cut by a Cas.

123. The method of embodiment 122, wherein the first vector or first strand comprises a sequence encoding a gRNA (gRNA1, eg, a single gRNA) that hybridises to PS1 in the cells or the vector or strand encodes a crRNA that forms gRNA1 in the cells, optionally with a tracrRNA encoded by host cell sequence.

Optionally, the tracrRNA is encoded by vector sequence, eg, by the first vector.

124. The method of embodiment 122 or 123, wherein PS1 and P1 are cognate to a Cas nuclease (eg, an endogenous Cas) of the cells that are killed, but not cognate to cells in the population that are not killed, wherein PS1 is selectively cut in the cells that are killed.

125. The method of any one of embodiments 122 to 124, wherein the mixed population is a human or non-human animal microbiome population, eg, a gut, vaginal, armpit or oral microbiome population.

126. The method of embodiment 125, comprising isolating the product population of embodiment 125 or a sample of said product.

127. A vector for transformation of a cell (eg, eukaryotic cell), wherein the vector comprises a first nucleic acid strand and the cell comprises a second nucleic acid strand, the first strand comprising
   (a) an insert sequence (IS) flanked by a first homology arm (HA1), wherein HA1 is complementary to a predetermined nucleotide sequence (NS1) of the second strand, wherein HA1 is capable of homologous recombination with NS1 in the cell to modify one or both strands;
   (b) a first protospacer sequence (PS1) adjacent a PAM (P1), wherein P1 is cognate to a first Cas nuclease for cutting PS1 at a first cut site (CS1);
   (c) wherein CS1 is at the end of, or flanking, HA1, wherein CS1 is capable of being cut by the first Cas to produce a cut first strand wherein HA1 is capable of homologous recombination with NS1.
   In an example, IS is immediately adjacent to HA1, eg, adjacent the 5' or 3' end of HA1. In an example, P1 is immediately adjacent (3' of) PS1. In an example, CS1 is not comprised by IS. For example, CS1 is at the end of HA1 furthest away from IS, or said end is between CS1 and IS.

128. The vector of embodiment 127, wherein the vector is a closed circular vector that is capable of transforming the cell and IS additionally comprises a nucleotide sequence of at least 10 kb (eg, a human sequence), wherein the circular vector is capable of transforming the cell for homologous recombination between HA1 and NS1.
   For example, IS is at least 50, 100, 200, 300, 400, 500, 600, 700, 800 or 900 kb or 1 Mb in length.
   The IS sequence is capable of insertion into the second strand by homologous recombination between HA1 and NS1.

129. The vector of embodiment 128, wherein the vector is supercoiled.

130. The vector of embodiment 127, 128 or 129, wherein the first strand is in combination with a guide RNA (gRNA1, eg, a single guide RNA); or is in combination with or comprises an expressible nucleotide sequence for producing gRNA1, wherein gRNA1 comprises a nucleotide sequence complementary to PS1 for guiding Cas to cut PS1.
   gRNA1 Is cognate to PS1, P1 and the first Cas for guiding the Cas to PS1 for cutting PS1.

131. The vector of any one of embodiments 127 to 130, wherein CS1 is no more than 250 nt away from HA1.
   In an example, CS1 is no more than 3, 4, 5, 6, 7, 8, 9, 10, 20, 30, 40, 50, 60, 70, 80, 90, 100, 150, 200 or 250 nt from said end of HA1

132. The vector of any one of embodiments 127 to 131, wherein
   (a) the first strand comprises a second homology arm (HA2) that is homologous to a second nucleotide sequence (NS2) of the second strand for homologous recombination between HA2 and NS2 in the cell and said modification of one or both strands; and
   (b) IS is between HA1 and HA2;
   (a) the first strand comprises a second protospacer sequence (PS2) adjacent a PAM (P2), wherein P2 Is cognate to the first Cas or a different Cas nuclease for cutting PS2 at a cut site (CS2);
   (c) wherein CS2 is at the end of, or flanking, HA2, wherein CS2 is capable of being cut by Cas to produce a cut first strand wherein HA2 is capable of homologous recombination with NS2.
   (d) CS1 of the first strand at the 5' end of HA1, or flanking 5' of said end; and/or Cas nuclease (eg, a Cas9, optionally *S. pyogenes* or *S. aureus* Cas9) cutting of a second cut site (CS2) of the first strand at the 3' end of HA2, or flanking 3' of said end.
   For example, P1 is immediately adjacent (3' of) PS1. In an example, CS1 is not comprised by IS. In an example, CS1 Is at the end of HA1 furthest away from IS, or said end is between CS1 and IS.
   In an example, directly IS joins HA1 to HA2. In an example, the vector (eg, a circular vector) is a retrieval vector, HA1 Is 5' to HA2 in the first strand; and NS1 is 3' of NS2 in the second strand, wherein the second strand comprises a retrieval sequence (RS) between NS1 and NS2; and wherein IS optionally comprises a marker sequence that is deleted when HA1 and HA2 recombine with NS1 and NS2 respectively and RS is retrieved into the first strand.
   In another example, the vector is an insertion vector and HA1 is 3' of HA2 in the first strand; and NS1 is 3' of NS2 in the second strand, A sequence of IS (eg a sequence of at least 10 kb) is inserted into the second strand when HA1 and HA2 recombine with NS1 and NS2 respectively. Optionally, IS is between HA1 and HA2 and comprises a marker sequence that is also inserted into the second strand and/or deleted from the first strand when HA1 and HA2 recombine with NS1 and NS2 respectively. This is useful for determining that successful homologous recombination has taken place. The second strand optionally comprises a nucleotide sequence joining NS1 to NS2 (or alternatively NS1 is directly adjacent NS2).

133. The vector of embodiment 132, wherein the first strand comprises in 5' to 3' direction, either (i) CS1, P1, HA1, IS, HA2, CS2 and P2; or (ii) CS2, P2, HA2, IS, HA1, CS1 and P1.

134. The vector of embodiment 133, wherein option (i) applies and P1 is comprised by HA1, eg, flanking 3' of the 5' end of HA1 or at said end; or option (ii) applies and wherein P2 is comprised by HA2, eg, flanking 3' of the 5' end of HA2 or at said end.

135. The vector of embodiment 132, 133 or 134, wherein CS2 is no more than 250 nt from HA2.
   In an example, CS2 is no more than 3, 4, 5, 6, 7, 8, 9, 10, 20, 30, 40, 50, 60, 70, 80, 90, 100, 150, 200 or 250 nt from said end of HA2.

136. The vector of any one of embodiments 127 to 135, wherein each of HA1 and HA2 is at least 100 nt in length.
   In an example, HA1 is at least 50 or at least 100, 150, 200, 300, 400, 500, 600, 700, 800 or 900 nt in length, or at least 1, 2, 3, 4, 5, 6, 7, 8, 9, 10, 20, 30, 50 or 100 kb in length. In an example, HA2 Is at least 50 or at least 100, 150, 200, 300, 400, 500, 600, 700, 800 or 900 nt in length, or at least 1, 2, 3, 4, 5, 6, 7, 8, 9, 10, 20, 30, 50 or 100 kb in length.
137. The vector of any one of embodiments 127 to 136, wherein HA1 and HA2 comprise a total length of at least 0.2 kb.
   In an example, HA1 and HA2 comprise or consist of a total length of at least 0.2, 0.3, 0.4, 0.5, 0.6, 0.7, 0.8, 0.9, 1, 2, 3, 4, 5, 6, 7, 8, 9, 10, 20, 30, 50 or 100 kb in length.
138. The vector of any one of embodiments 127 to 137, wherein HA1 and HA2 are isogenic (ie, are 100% identical nucleotide sequences) to NS1 and NS2 respectively.
   In an example, HA1 and HA2 are each at least 80, 85, 90 or 95% identical to the nucleotide sequences of NS1 and NS2 respectively.
139. The vector of any one of embodiments 127 to 138, wherein the first or each strand is a dsDNA.
140. The vector of any one of embodiments 127 to 138, wherein the first or each strand is a ssDNA.
141. The vector of any one of embodiments 127 to 140, wherein PS1 and/or PS2 each comprises a seed sequence that comprises a nucleotide sequence rare or not found in the cell genome (eg, a human cell genome).
142. The vector of embodiment 141, wherein each seed sequence comprises a prokaryotic start codon, eg, GTG and/or TTG codon, and optionally the seed sequence does not comprise an ATG codon.
143. The vector of embodiment 141 or 142, wherein each seed sequence comprises a Shine Dalgamo sequence, eg, the seed sequence comprises GAGG or AGGAGG.
144. The vector of any one of embodiments 141 to 143, wherein the PS1 and/or PS2 sequence each is optimised for prokaryotic (eg, E col), archaeal or viral use, or is not found in the cell genome (eg, human cell genome).
145. The vector of embodiment 144, wherein each said protospacer sequence (eg which is up to 25 or 20 contiguous nucleotides) comprises a sequence of a bacterial Pribnow box; bacterial leader sequence (eg, Pel 8); bacterial −10 sequence or bacterial −35 element sequence (eg, TATAAT or TTGACA); a bacterial upstream promoter element (UP element) sequence; bacterial regulatory or operon sequence; or a bacterial origin of replication sequence.
146. The vector of any one of embodiments 127 to 145, wherein the vector is in combination with, or comprises, an expressible nucleic acid encoding the first Cas (eg, a Cas9); or wherein the vector is. In combination with said Cas.
147. The vector of any one of embodiments 127 to 146, wherein the vector is inside said eukaryotic cell (eg, a human cell, eg, a human stem cell or IPS cell in vitro).
148. A collection of vectors comprising a population of closed circular (eg, supercoiled vectors), wherein each said circular vector is according to any one of embodiments 127 to 147, eg, wherein IS in each vector comprises a sequence (eg, human sequence) of at least 10 kb in length.
149. An antibiotic (eg, anti-bacterial or anti-archaeal) composition comprising the vector, combination or collection of any one of embodiments 127 to 148.
150. A medicament for treating or preventing a disease or condition (eg, a bacterial infection or obesity) in a human, the medicament comprising the vector, combination or collection of any one of embodiments 127 to 149.
151. The vector, combination, collection, antibiotic or medicament according to any one of embodiments 127 to 150, wherein the vector or each vector of the collection is further according to any one of embodiments 100 to 106.
152. A method of producing a precursor vector, eg, wherein the vector is a precursor of the vector recited in embodiment 80, the precursor vector comprising
   (a) in 5' to 3' order, a first protospacer sequence (PS1) adjacent a PAM (P1), wherein P1 is cognate to a first Cas nuclease for cutting PS1 at a first cut site (CS1); and
   (b) a first nucleotide sequence immediately 3' of P1, wherein the first sequence comprises a first cloning site adjacent the 3' end of P1, or flanking 3' of said end, for cloning a second nucleic acid sequence into the precursor vector, wherein the second sequence comprises one or both of HA1 and HA2;
   the method comprising
   (c) obtaining a precursor nucleic acid;
   (d) identifying the cloning site in the nucleic acid or creating the cloning site in the nucleic acid; and
   (e) identifying the PS1/P1 combination in the nucleic acid or creating the combination in the nucleic acid;
      wherein (d) and (e) are carried out in any order or simultaneously, and wherein at least one of (d) and (e) comprises a said creating step, whereby said precursor vector is produced and optionally isolated.
In an alternative, there is provided:—
152a. A method of making a first nucleic acid strand suitable for homologous recombination with a second nucleic acid strand, eg, in a method according to any preceding claim, the method of making comprising:—
   (a) identifying first and second nucleotides sequences (NS1 and NS2) of the second strand, optionally wherein NS1 is selected so that it is 3' of NS2 in the second strand;
   (b) combining in another nucleic acid strand
      i. a first homology arm (HA1) complementary to first predetermined target nucleotide sequence NS1 of the second strand for homologous recombination between HA1 and NS1:
      ii. a second homology arm (HA2) complementary to second predetermined target nucleotide sequence NS2 of the second strand for homologous recombination between HA2 and NS2; and
      iii. a first protospacer sequence (PS1) adjacent a PAM (P1), wherein P1 is cognate to a first Cas nuclease for cutting PS1 at a first cut site (CS1), wherein CS1 is at the 5' end of HA1 or flanking 5' of said end; and/or a second protospacer sequence (PS2) adjacent a PAM (P2), wherein P2 is cognate to said first or a different Cas nuclease for cutting PS2 at a second cut site (CS2), wherein CS2 is at the 3' end of HA2 or flanking 3' of said end;
      whereby the first strand is produced.
153. The method of embodiment 152 or 152a, wherein the product vector is a circular vector, eg, a closed circular vector.
154. The method of embodiment 152 or 153, wherein the cloning site is no more than 1, 2, 3, 4, 5, 6, 7, 8, 9, 10, 15, 20, 25, 30, 40, 50, 100, 200 or 250 nt away from CS1.
155. The method of any one of embodiments 152 to 154, wherein the precursor vector comprises a second cloning site 3' of the first cloning site, the method comprising identifying the second cloning site in the nucleic acid or creating the second cloning site in the nucleic acid.
156. The method of embodiment 155, wherein the precursor vector comprises in 5' to 3' order, a second protospacer sequence (PS2) adjacent a PAM (P2), wherein P2 is cognate to said first Cas or a different Cas nuclease for cutting PS2 at a second cut site (CS2); wherein the second cloning site is adjacent the 5' end of PS2, or flanking 5' of said end.
157. The method of embodiment 156, wherein the method comprises identifying or creating the PS2/P2 combination, wherein at least one of said second cloning site and the PS2/P2 combination is created.
158. The method of embodiment 155, 156 or 157, wherein the precursor vector comprises a marker sequence (eg, for expressing a detectable marker) between the cloning sites, wherein the marker is lost from the vector when the second sequence is inserted into the cloning sites.
   The marker sequence can be any marker sequence disclosed herein, eg, a tk or HPRT sequence.
159. The method of any one of embodiments 152 to 158, wherein the first or each cloning site is a restriction endonuclease site (eg, wherein the sites are recognised by the same endonucleases).
160. The method of any one of embodiments 152 to 158, wherein the first or each cloning site is a site-specific recombination (SSR) site (eg, wherein the same SSR sites); optionally wherein the first or each site is a lox or frt site.
   In an example, incompatible lox sites are used (eg, loxP and lox511; or loxP and lox2272).
161. The method of any one of embodiments 155 to 160, further comprising obtaining said second nucleic acid sequence and cloning the second sequence into the cloning sites, wherein HA1 and HA2 are inserted into the precursor vector 3' of P1 and the marker sequence is deleted from the vector, and optionally detecting at least one of (i) the loss of the marker sequence from the vector or loss of the marker expression product, (i) the presence of HA1 sequence in the vector and (iii) the presence of HA2 sequence in the vector; and optionally isolating the product vector.
162. The method of embodiment 156 to 160, comprising after producing the product precursor vector, using Cas cutting of CS1 and/or CS2, optionally with the same Cas nuclease.
163. The method of any one of embodiments 152 to 162, further comprising obtaining said second nucleic acid sequence and cloning the second sequence into the first cloning site, wherein HA1 and HA2 are inserted into the precursor vector 3' of P1; and optionally isolating the product vector.
164. The method of embodiment 161, 162 or 163, comprising thereafter using the product vector in a further method according to any one of embodiments 1 to 79, wherein the product vector of embodiment 161, 162 or 163 provides said first strand in the further method.
165. The method of any one of embodiments 80 to 99, wherein step (b) uses the method of any one of embodiments 152 to 164.
166. A precursor vector obtainable by the method of any one of embodiments 152 to 163.
167. The vector of embodiment 166, wherein the vector is a dsDNA vector and optionally circular.
168. The vector of embodiment 166, wherein the vector is a ssDNA vector and optionally circular.
169. The vector of any one of embodiments 166 to 168, wherein PS1 and/or PS2 each comprises a seed sequence that comprises a nucleotide sequence rare or not found in the cell genome (eg, a human cell genome).
170. The vector of embodiment 169, wherein each seed sequence comprises a prokaryotic start codon, eg, GTG and/or TTG codon, and optionally the seed sequence does not comprise an ATG codon.
171. The vector of embodiment 169 or 170, wherein each seed sequence comprises a Shine Dalgarno sequence, eg, the seed sequence comprises GAGG or AGGAGG.
172. The vector of any one of embodiments 169 to 171, wherein the PS1 and/or PS2 sequence each is optimised for prokaryotic (eg. E col), archaeal or viral use, or is not found in the cell genome (eg, human cell genome).
173. The vector of embodiment 172, wherein each said protospacer sequence (eg which is up to 25 or 20 contiguous nucleotides) comprises a sequence of a bacterial Pribnow box; bacterial leader sequence (eg, Pel 8); bacterial −10 sequence or bacterial −35 element sequence (eg, TATAAT or TTGACA); a bacterial upstream promoter element (UP element) sequence; bacterial regulatory or operon sequence; or a bacterial origin of replication sequence.
174. The vector of any one of embodiments 166 to 173, wherein the vector is in combination with, or comprises, an expressible nucleic acid encoding the first Cas (eg, a Cas9); or wherein the vector is in combination with said Cas.
175. The vector or combination of any one of embodiments 166 to 174, wherein the precursor vector is in combination with a guide RNA (gRNA1, eg, a single guide RNA); or is in combination with or comprises an expressible nucleotide sequence for producing gRNA1, wherein gRNA1 comprises a nucleotide sequence complementary to PS1 for guiding Cas to cut PS1.
   gRNA1 Is cognate to PS1. P1 and the first Cas for guiding the Cas to PS1 for cutting PS1.
176. The vector or combination of any one of embodiments 166 to 175, wherein the precursor vector is obtainable by the method of embodiment 156 and is in combination with a guide RNA (gRNA2, eg, a single guide RNA); or is in combination with or comprises an expressible nucleotide sequence for producing gRNA2, wherein gRNA2 comprises a nucleotide sequence complementary to PS2 for guiding Cas to cut PS2.
   gRNA2 is cognate to PS2, P2 and the first Cas for guiding the Cas to PS2 for cutting PS2.

The invention provides the following clauses:—
1. A method of retrieving a donor nucleic acid sequence in a prokaryotic or eukaryotic cell (eg, a human cell, eg, an iPS cell), the method comprising
   (a) providing a first nucleic acid strand (eg, comprised by an engineered vector), the strand comprising a protospacer sequence (PS1) adjacent a PAM (P1) that is cognate to a first Gas nuclease;
   (b) introducing the first strand into a host cell to combine a donor nucleic acid strand inside the cell with the first strand; and
   (c) using Gas nuclease cutting of PS1 of the first strand with the first Gas nuclease;
   (d) allowing the cut first strand to undergo homologous recombination with the donor strand inside the cell, wherein a sequence of the donor strand is inserted into the first strand to form a modified first strand, whereby PS1 and/or P1 is not re-formed in the modified first strand by the insertion of the donor sequence.

In an example, the donor strand is comprised by a chromosomal or episomal nucleic acid of the cell.

2. A method of deleting a donor nucleic acid sequence in a or eukaryotic prokaryotic cell, the method comprising
   (a) providing a first nucleic acid strand (eg, comprised by an engineered vector), the strand comprising a protospacer sequence (PS1) adjacent a PAM (P1) that is cognate to a first Cas nuclease;
   (b) introducing the first strand into a host cell to combine a donor nucleic acid strand inside the cell with the first strand; and
   (c) using Cas nuclease cutting of PS1 of the first strand with the first Cas nuclease;
   (d) allowing the cut first strand to undergo homologous recombination with the donor strand inside the cell, wherein a sequence of the donor strand is deleted to form a modified donor strand, wherein PS1 and/or P1 is not formed at or flanking the deletion in the modified donor strand.

3. The method of clause 1 or 2, wherein sequence is deleted from the first strand and/or donor strand in step (c) or (d).

4. The method of any preceding clause, wherein PS1 sequence is deleted, whereby PS1 is rendered non-functional in the first strand.

5. The method of any preceding clause, wherein P1 sequence is deleted, whereby P1 is rendered non-functional in the first strand.

6. The method of any preceding clause, wherein donor sequence is inserted into the first strand, or sequence is deleted from the first strand, to form a new protospacer adjacent P1; the method optionally comprising cutting the new protospacer after step (d).

7. The method of clause 6, wherein the new protospacer is cut to produce a further modified first strand that is used for homologous recombination with a further nucleic acid strand for sequence insertion into or deletion from the further modified first strand.

8. The method of any one of clauses 1 to 5, wherein donor sequence is inserted into the first strand, or sequence is deleted from the first strand, to form a new PAM adjacent PS1; the method optionally comprising cutting PS1 after step (d) using a Cas nuclease that is different from the first Cas.

9. The method of clause 8, wherein PS1 is cut with said different Cas to produce a further modified first strand that is used for homologous recombination with a further nucleic acid strand for sequence insertion into or deletion from the further modified first strand.

10. The method of any one of clauses 1 to 4, wherein step (c) or (d) deletes a marker sequence (eg, an antibiotic resistance gene sequence) of the first strand, wherein the method optionally comprises detecting that the absence or reduction of the marker after step (d).

11. The method of any preceding clause, wherein first strand sequence is inserted into the donor strand, or sequence is deleted from the donor strand, to form (i) a new protospacer adjacent a PAM; the method optionally comprising cutting the new protospacer after step (d) and/or (ii) a new marker sequence in the donor strand, eg, wherein the marker sequence is functional for expressing a detectable marker.

12. The method of clause 11, wherein (i) the new protospacer is cut to produce a further modified donor strand that is used for homologous recombination with a further nucleic acid strand for sequence insertion into or deletion from the further modified donor strand and/or (ii) the marker is detected to determine that homologous recombination. In step (d) has taken place.

13. The method of clause 11 or 12, wherein the new protospacer and PAM sequences or marker sequences are comprised by nucleotide sequences (NS3 and NS4) found in the donor strand before step (d) and the new protospacer/PAM combination or marker sequence is formed after deletion of a donor sequence in step (d) and joining of NS3 to NS4.

14. The method of clause 13, wherein the first strand in step (a) comprises a first homology arm (HA1), wherein HA1 is homologous to a predetermined first nucleotide sequence (NS1) of the donor nucleic acid strand; in step (d) homologous recombination is carried out between HA1 and NS1 to produce the modified strand; before step (d) NS1 is flanking 3' of the donor sequence to be deleted and NS3 is at (at or spaced by up to 10 nucleotides) the 5' end of NS1, and wherein NS4 is flanking 5' of the donor sequence to be deleted, wherein in step (d) the donor sequence is deleted and the 5' end of NS3 is joined to the 3' end of NS4, thereby forming the new protospacer/PAM combination or marker sequence in the donor strand.

15. The method of clause 13, wherein the first strand in step (a) comprises a first homology arm (HA1), wherein HA1 is homologous to a predetermined first nucleotide sequence (NS1) of the donor nucleic acid strand; in step (d) homologous recombination is carried out between HA1 and NS1 to produce the modified strand; before step (d) NS1 is flanking 5' of the donor sequence to be deleted and NS3 is at (at or spaced by up to 10 nucleotides) the 3' end of NS1, and wherein NS4 is flanking 3' of the donor sequence to be deleted, wherein in step (d) the donor sequence is deleted and the 3' end of NS3 is joined to the 5' end of NS4, thereby forming the new protospacer/PAM combination or marker sequence in the donor strand.

16. The method of clause 14 or 15 wherein the first strand in step (a) comprises first and second homology arms (HA1 and HA2 respectively), wherein HA1 is homologous to NS1 of the donor nucleic acid strand, and HA2 is homologous to a predetermined second nucleotide sequence (NS2) of the donor nucleic acid strand; wherein an intervening sequence connects NS1 to NS2 in the donor strand before step (d) and comprises the sequence to be deleted, and wherein NS2 comprises NS4; optionally wherein the deletion sequence comprises a sequence (marker sequence) for indicating homologous recombination between HA1 and NS1 and between HA2 and NS2; wherein the deletion sequence is deleted from the donor strand in step (d) by homologous recombination between HA1 and NS1 and between HA2 and NS2.

17. The method of any preceding clause, comprising using a cutting site motif to direct cutting (eg, Cas-, meganuclease-, zinc finger protein- or TALEN-mediated cutting) of the donor strand before step (d), wherein step (d) is carried out with cut first and donor strands.

18. The method of clause 17, wherein the motif is destroyed by the homologous recombination in step (d)

(eg, a protospacer and/or PAM in the donor strand that was used for cutting according to clause 17 is destroyed).

19. The method of any preceding clause, wherein the first strand in step (a) comprises:—
   (a) a first homology arm (HA1), wherein HA1 is homologous to a predetermined first nucleotide sequence (NS1) of the donor nucleic acid strand; and
   (b) a first cut site (CS1) comprised by PS1, wherein CS1 is cut by the first Cas in step (c);
   (c) wherein (i) CS1 is at the 5' end of HA1 of flanking 5' of said end; or (ii) wherein CS1 is at the 3' end of HA1 of flanking 3' of the 3' end; and
      wherein step (d) comprises allowing HA1 of the cut first strand to undergo homologous recombination with NS1 of the donor strand, wherein a sequence of the donor strand is inserted into the first strand and/or a donor sequence is deleted.

20. The method of clause 19, wherein the first strand in step (a) comprises
   (c) a second homology arm (HA2), wherein HA2 is homologous to a predetermined second nucleotide sequence (NS2) of the donor nucleic acid strand; and
   (d) an intervening sequence connecting the homology arms, and
   wherein either
   (e) the intervening sequence comprises a deletion sequence, optionally wherein the deletion sequence comprises a sequence (marker sequence) for indicating homologous recombination between HA1 and NS1 and between HA2 and NS2; wherein the deletion sequence is deleted from the first strand in step (c) or (d) by homologous recombination between HA1 and NS1 and between HA2 and NS2; or
   (f) the intervening sequence comprises CS1 (eg, wherein CS1 is spaced no more than 250 nt away from HA1 and/or HA2) and optionally NS1 and NS2 flank either side of a sequence that is deleted from the donor strand.

21. The method of clause 19 or 20, wherein the first strand in step (a) comprises:—
   (e) a second homology arm (HA2), wherein HA2 is homologous to a second predetermined nucleotide sequence (NS2) of the donor nucleic acid strand; and
   (f) a second protospacer (PS2) and cognate PAM (P2) that is cut at a second cutting site (CS2) in step (c) by the first or a different (second) Cas nuclease;
      wherein (i) CS1 is at the 5' end of HA1 of flanking 5' of said end and CS2 is at the 3' end of HA2 or flanking 3' of said end of HA2; or (ii) wherein CS1 is at the 3' end of HA1 of flanking 3' of the 3' end of HA1 and CS2 Is at the 5' end of HA2 or flanking the 5' end of the 5' end of HA2; and
      wherein step (d) comprises allowing HA1 of the cut first strand to undergo homologous recombination with NS1 of the donor strand and HA2 to undergo homologous recombination with NS2, wherein a sequence of the donor strand is inserted into the first strand.

22. The method of any preceding clause, wherein the first stand of step (a) comprises a second protospacer (PS2) and cognate PAM (P2), wherein PS2 is cut in step (c) by the first or a different (second) Cas nuclease, wherein cutting of PS1 and PS2 excises first strand sequence between PS1 and PS2.

23. The method of clause 22, wherein the excised sequence renders a first strand marker sequence non-functional. In the cell, wherein the method optionally comprises detecting that the absence or reduction of the marker after step (d).

24. The method of any one of clauses 21 to 23, wherein cutting of PS1 and PS2 produces cut first strand ends which recombine with the donor nucleic acid, wherein a sequence of the donor nucleic acid is inserted into the first strand between the ends.

25. The method of any one of clauses 20 to 24, wherein PS2 and/or P2 is not re-formed in the modified first strand by the insertion of the donor sequence.

26. The method of any preceding clause, the method comprising isolating or copying (eg, using PCR) the modified first strand or the donor nucleic acid sequence in the modified first strand.

27. The method of any preceding clause, the method comprising isolating or copying (eg, using PCR) the modified donor strand or the region of donor nucleic acid sequence where deletion occurred.

28. The method of any preceding clause, wherein donor sequence is inserted into the first strand in step (d) and the inserted sequence comprises or consists of a regulatory element, protein-encoding sequence, an exon or a marker sequence.

29. The method of any preceding clause, wherein donor sequence is inserted into the first strand in step (d) and the inserted sequence is functional for expression from the modified first strand.

30. The method of clause 29, wherein the inserted sequence is a protein-encoding sequence, an exon or a marker sequence that is inserted in functional arrangement with a first strand regulatory element, whereby the regulatory element is capable of controlling expression of the donor sequence from the modified first strand.

31. The method of any preceding clause, wherein donor sequence is inserted into the first strand in step (d) and the inserted sequence is a marker sequence, and the method comprises detecting the marker sequence in the modified first strand; or detecting the expressed marker, wherein the marker is not detectable before step (d).

32. The method according to preceding clause, the method comprising before step (d) using Cas cutting of the donor nucleic acid strand at or flanking one or both ends of said sequence to be inserted into the first strand, optionally using the first or second Cas nuclease.
   For example, cutting is at both ends, flanking both ends, at the 5' end and flanking the 3' end, flanking the 5' end and at the 3' end, at the 5' end, at the 3' end.

33. The method of any preceding clause, wherein the donor strand is comprised by a host cell chromosomal or episomal nucleic acid.

34. The method according to clause 33, wherein the donor nucleic acid sequence is deleted from the host chromosome or episome (eg, plasmid) in step (d).

35. The method of clause 34, wherein the deletion from the chromosome or episome is lethal to the host cell.

36. The method of any one of clauses 33 to 35, wherein the method down-regulates cell viability, growth or proliferation (eg, kills the cell).

37. The method of any one of clauses 33 to 35, wherein the method up-regulates cell viability, growth or proliferation.

38. The method of any preceding clause, the method comprising after step (d) isolating the modified cell, modified first strand, modified donor strand and/or modified host chromosomal or episomal nucleic acid in which the host nucleic acid sequence has been deleted by the method.
39. The method of any preceding clause, wherein the method is carried out in a bacterial or archaeal cell, eg, an *E. coli* cell.
40. The method of clause 39, wherein the cell is of a human pathogen species.
41. The method of clause 39 or 40, wherein the cell is a cell of a human microbiome species, eg, a human gut microbiome species.
42. The method of any preceding clause, wherein the method is a recombineering method.
43. The method of any preceding clause, wherein the cell comprises an endogenous CRISPR/Cas system and wherein endogenous host Cas is used to cut in step (c).
44. The method of any preceding clause, wherein the method is carried out without introducing exogenous Cas or a sequence encoding exogenous Cas into the cell.
45. The method of any preceding clause, wherein the method is carried out in cells to kill a population of prokaryotic cells, wherein the cells are of the same species or strain.
46. The method of clause 45, wherein the population is comprised by a mixed population of prokaryotic (eg, bacterial) cells and the method selectively kills some but not all cells in the mixed population, wherein the killed cells are cells in which the first strand was introduced and PS1 cut by a Cas.
47. The method of clause 45 or 46, wherein PS1 and P1 are cognate to a Cas nuclease (eg, an endogenous Cas) of the cells that are killed, but not cognate to cells in the population that are not killed, wherein PS1 is selectively cut in the cells that are killed.
48. The method of any one of clauses 45 to 47, comprising isolating the product population or a sample of said product.
49. The method of any one of clauses 45 to 48, wherein the cell or population is comprised by a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor).
50. The method of any preceding clause, wherein the cutting comprises exposing the first strand to a guide RNA (gRNA1, eg, a single gRNA) that hybridises to PS1 in the cell to guide the Cas to cut PS1; optionally wherein the step comprises expressing gRNA1 or crRNA sequence thereof from a nucleotide sequence introduced (eg, as part of the first strand) in step (b).
51. The method of any preceding clause, wherein the first or each strand is a dsDNA.
52. The method of any preceding clause, wherein the first or each strand is a ssDNA.
53. The method of any preceding clause, wherein the first strand and/or donor strand is comprised by a BAC, PAC, YAC, cosmid or plasmid.
54. The method of any preceding clause, wherein the first strand is circular prior to cutting.
In any configuration herein, the first strand or a vector (eg, first strand or donor or further strand vector) is a linear DNA.
55. The method of any one of clauses 1 to 52 and 54, wherein the cell is a bacterial cell and the first strand is a bacteriophage nucleic acid strand, wherein the bacteriophage strand is introduced into the host cell by infecting the host cell with the bacteriophage.
56. The method of clause 19, or any preceding clause when dependent from clause 19, wherein HA1 Is spaced no more than 250 nt away from CS1 (or any other spacing disclosed herein).
57. The method of any one of clauses 14 to 16 and 19, or any preceding clause when dependent from any one of clauses 14 to 16 and 19, or the method of claim 56 wherein HA1 comprises at least 15 contiguous nucleotides (or any other length disclosed herein).
58. The method of any one of clauses 14 to 16 and 19, or any preceding clause when dependent from any one of clauses 14 to 16 and 19, or the method of clause 56 or 57 wherein the sequence of HA1 is isogenic to NS1 (or any other % identity disclosed herein).
59. The method of clause 21, or any preceding clause when dependent from clause 16 or 20, or the method of clause 56, 57 or 58, wherein HA2 Is spaced no more than 250 nt away from CS2 (or any other distance disclosed herein).
60. The method of any one of clauses 16 and 20 to 22, or any preceding clause when dependent from any one of clauses 16 and 20 to 22, or the method of any one of clauses 56 to 59, wherein HA2 comprises at least 15 contiguous nucleotides (or any other length disclosed herein).
61. The method of any one of clauses 16 and 20 to 22, or any preceding clause when dependent from any one of clauses 16 and 20 to 22, or the method of any one of clauses 56 to 60, wherein the sequence of HA2 is isogenic to NS2 (or any other % identity disclosed herein).
62. A method of making a first nucleic acid strand (eg, comprised by a retrieval vector) suitable for homologous recombination with a second nucleic acid strand, eg, in a method according to any preceding clause, the method of making comprising combining in a nucleic acid strand
    (a) an insert sequence (IS) comprising (or consisting of) a first homology arm (HA1) complementary to a first predetermined target nucleotide sequence (NS1) of the second strand for insertion of IS into the second strand by homologous recombination;
    (b) a first protospacer sequence (PS1) adjacent a PAM (P1), wherein P1 is cognate to a first Cas nuclease for cutting PS1 at a first cut site (CS1);
wherein CS1 is at an end of, or flanking, HA1, wherein when CS1 is cut by Cas HA1 is capable of homologous recombination with NS1 for said insertion of IS.
In any configuration herein, a or each strand or vector is for example isolated.
63. The method of clause 62, the method comprising further combining in the nucleic acid strand
    (c) a second homology arm (HA2) complementary to a second predetermined sequence (NS2) of the second strand; and
    (d) optionally a second protospacer sequence (PS2) adjacent a second PAM (P2), wherein P2 is cognate to a Cas nuclease for cutting PS2 at a second cut site (CS2); wherein when CS2 is cut by Cas HA2 Is capable of homologous recombination with NS2 for insertion of IS.

64. The method of clause 63, comprising cutting CS2 with the Cas nuclease that is cognate to P2.
65. The method of clause 64, the method comprising cutting CS1 and CS2 with the same Cas nuclease.
66. The method of any one of clauses 62 to 65, wherein NS1 and NS2 flank a sequence of an essential gene, antibiotic resistance gene or virulence gene of the cell.
67. The method of clause 66, further producing an antibiotic composition or kit comprising product of the method in combination with an antibiotic, wherein NS1 and NS2 flank a sequence of an antibiotic resistance gene, wherein the antibiotic is the antibiotic combined with the nucleic acid.
68. The method of any one of clauses 62 to 67, wherein CS1 is spaced no more than 250 nt away from HA1 and/or HA2.
69. The method of any one of clauses 62 to 68, wherein the strand is as defined in any one of clauses 51 to 61.
70. The method of any one of clauses 62 to 69, the method comprising cutting CS1 with the first Cas (eg, a Cas9, optionally S. pyogenes or S. aureus Cas9).
71. The method of any one of clauses 52 to 70, further including in the first strand (or on a further nucleic strand in addition to the first strand) a nucleotide sequence that encodes a gRNA (gRNA1, eg, a single gRNA) that is complementary to PS1 or the sequence encodes a crRNA that forms gRNA1 in the cell, optionally with a tracrRNA encoded by host cell sequence.
In an example, the tracrRNA is encoded by vector sequence, eg, by the first vector.
72. The method of any one of clauses 1 to 71, wherein the first strand product of the method is in a vector, eg, a closed circular vector which is optionally supercoiled.
73. An engineered first nucleic acid strand obtainable by the method of any one of clauses 62 to 72, the strand comprising
    (a) a first homology arm (HA1), wherein HA1 Is homologous to a first predetermined nucleotide sequence (NS1) of a donor nucleic acid strand of a prokaryotic cell;
    (b) a first protospacer sequence (PS1) adjacent a PAM (P1), wherein P1 is cognate to a first Cas nuclease for cutting PS1 at a first cut site (CS1);
    (g) a second homology arm (HA2), wherein HA2 is homologous to a second predetermined nucleotide sequence (NS2) of the donor nucleic acid strand; and
    (c) an intervening sequence connecting the homology arms, wherein the intervening sequence comprises CS1; or wherein CS1 is outside the intervening sequence and at or flanking an end of HA1.
74. The nucleic strand of clause 73 for carrying out the method of clause 16, 20 or 21, wherein NS1 and NS2 flank a sequence of an essential gene, antibiotic resistance gene or virulence gene of the cell.
75. The nucleic acid strand of clause 74 in combination with an antibiotic, wherein NS1 and NS2 flank a sequence of an antibiotic resistance gene, wherein the antibiotic is the antibiotic combined with the nucleic acid.
76. The nucleic acid strand of clause 73, 74 or 75, wherein CS1 is spaced no more than 250 nt away from HA1 and/or HA2.
77. The first nucleic acid strand of any one of clauses 73 to 76, optionally in combination with a further nucleic acid strand, wherein the first strand or further strand comprises an expressible nucleotide sequence that encodes a gRNA (gRNA1, eg, a single gRNA) that is complementary to PS1; or the sequence encodes an expressible crRNA that forms gRNA1 in the cell, optionally with a tracrRNA encoded by host cell sequence, the first strand or the further strand.
In an example, the tracrRNA is encoded by vector sequence, eg, by the first vector.
78. The first nucleic acid strand of any one of clauses 73 to 77, wherein CS1 is outside the intervening sequence and at or flanking an end of HA1; the strand comprising a second protospacer (PS2) and cognate PAM (P2) for cutting PS2 at a second cutting site (CS2) in step (c) by the first or a different (second) Cas nuclease; wherein CS2 Is outside the intervening sequence and at or flanking an end of HA2.
79. The first nucleic acid strand of clause 78, optionally in combination with said or another further nucleic acid strand, wherein the first strand or further strand comprises an expressible nucleotide sequence that encodes a gRNA (gRNA2, eg, a single gRNA) that is complementary to PS2; or the sequence encodes an expressible crRNA that forms gRNA2 in the cell, optionally with a tracrRNA encoded by host cell sequence, the first strand or the further strand.
In an example, the tracrRNA is encoded by vector sequence, eg, by the first vector.
80. The first nucleic acid strand of clause 78 when dependent from clause 77, wherein the gRNA1- and gRNA2-encoding sequences (or respective crRNA-encoding sequences) are comprised by the same nucleic acid strand, optionally the first strand.
81. The first nucleic acid strand of any one of clauses 77 to 80, in combination with an expressible nucleotide sequence encoding said first Cas (eg, a Cas9), wherein the first Cas nucleotide sequence is comprised by the first strand, said further nucleic strand or another further nucleic acid strand; optionally wherein P2 is cognate to the first Cas.
82. The nucleic acid strand of any one of clauses 73 to 81, wherein the strand is as defined in any one of clauses 51 to 61.
83. An antimicrobial composition comprising the nucleic acid strand of any one of clauses 73 to 82.
84. A foodstuff, beverage or industrial fluid (eg, stored water) comprising the composition of clause 83.
85. A composition comprising one or more nucleic acid vectors, a first said vector comprising the first nucleic acid strand as defined in any one of clauses 73 to 84, wherein said further strand(s) are comprised by the composition and each further strand is comprised a vector that is different from the first vector.
86. The composition of clause 85, comprising a first vector that comprises the first strand, a second vector that comprises an expressible nucleotide sequence encoding said first Cas and optionally a third vector, wherein the first, second or third vector comprises said gRNA1-encoding nucleotide sequence recited in clause 77; and optionally the first, second or third vector comprises said gRNA2-encoding nucleotide sequence recited in clause 79.
In any configuration herein, optionally said or each Cas is a nickase, or one of the Cas nucleases (eg, the first Cas) is a nickase.
87. The composition of clause 85 or 86, wherein the first or each vector is a dsDNA vector.
88. The composition of clause 85 or 86, wherein the first or each vector is a ssDNA vector.

89. The composition of any one of clauses 85 to 88, wherein the first vector or each vector is a BAC, PAC, YAC or plasmid, eg, all vectors are plasmids or the first vector is a BAC and the other vectors are plasmids.
90. The composition of any one of clauses 85 to 89, wherein the first vector or each vector is circular prior to cutting.
91. A first vector or combination of vectors, wherein
    (a) the first vector comprises an engineered first nucleic acid strand, the strand comprising a first protospacer sequence (PS1) adjacent a PAM (P1), wherein P1 is cognate to a first Cas nuclease for cutting PS1 at a first cut site (CS1); and
    (b) the first vector or another vector of said combination comprises an expressible nucleotide sequence that encodes a gRNA (gRNA1, eg, a single gRNA) that is complementary to PS1 for guiding Cas to cut PS1; or the expressible sequence encodes a crRNA that forms gRNA1 with a tracrRNA.
92. The vector or combination of clause 91, in combination with an expressible nucleotide sequence encoding said first Cas (eg, a Cas9), wherein the first Cas nucleotide sequence is comprised by the first vector and said expressible sequence of (b) is comprised by the first vector or another vector of said combination.
93. The vector or combination of clause 92, wherein CS1 is comprised by the expressible nucleotide sequence encoding said first Cas or the sequence of a regulatory element thereof, wherein CS1 is capable of being cut by the first Cas to down-regulate or inactivate expression of the first Cas from the expressible nucleotide sequence thereof.
94. The vector or combination of clause 91, in combination with an expressible nucleotide sequence encoding said first Cas (eg, a Cas9), wherein the first Cas nucleotide sequence is comprised by a second vector that is in combination with the first vector; and said expressible sequence of (b) is comprised by the first vector or another vector of said combination (eg, said second vector).
95. The vector or combination of any one of clauses 91 to 94, wherein the first strand comprising a second protospacer (PS2) and cognate PAM (P2) for cutting PS2 at a second cutting site (CS2) by the first or a different (second) Cas nuclease.
96. The vector or vector combination of clause 95, wherein P1 and P2 are joined by an intervening sequence (IS) that is excisable from the vector when CS1 and CS2 are cut, wherein IS comprises a regulatory element, protein-encoding sequence, an exon or a marker sequence.
97. A kit comprising the vector or combination of clause 96 and first and second PCR primers, wherein the first primer is complementary to a nucleotide sequence of IS and the second primer is complementary to a nucleotide sequence outside IS, wherein the primers are capable of detecting the presence of the marker in the first vector.
98. The vector or combination of clause 95, wherein P1 and P2 are joined by an intervening sequence (IS) that is excisable from the vector when CS1 and CS2 are cut, wherein IS (i) comprises P1 and PS2 sequences, or (ii) comprises P2 and PS1 sequences, wherein excision of the intervening sequence is detectable by the absence of sequences (i) or (ii).
99. The vector or combination of any one of clauses 96 to 98, wherein the first vector comprises first and second homology arms (HA1 and HA2) flanking (eg, immediately 5' and 3' of) CS1 and CS2 respectively for homologous recombination with predetermined target nucleotide sequences (NS1 and NS2 respectively).
100. The vector or combination of clause 99, wherein NS1 and NS2 are sequences of a prokaryotic cell genome, eg, are sequences of an essential gene, virulence gene or antibiotic resistance gene (eg, in or flanking an exon or regulatory element).
101. The vector or combination of any one of clauses 91 to 100 for treating, preventing or diagnosing a disease or condition in a human or non-human animal, eg, for gene therapy of a human or animal, human or animal cell when the method is carried out in a human or animal cell; or for treating or preventing a bacterial infection in a human or animal when the method is carried out in a bacterial cell.

The invention also provides the following paragraphs:—
1. A method of inhibiting viability, growth or proliferation of a prokaryotic host cell, the method comprising
    (a) providing a first vector comprising a protospacer sequence (PS1) adjacent a PAM (P1) that is cognate to a first Cas nuclease;
    (b) providing a toxin or toxin precursor; or a vector comprising a sequence encoding a toxin or toxin precursor, wherein the toxin is toxic to the prokaryotic cell;
    (c) combining the cell with the vector(s) wherein the vector(s) are introduced into the cell, and providing the toxin in the cell; and
    (d) using Cas nuclease cutting of PS1 of the first vector using the first Cas nuclease, wherein the cutting promotes toxin activity in the cell, whereby the cell is killed or cell growth or proliferation reduced.
2. The method of paragraph 1, wherein the cutting cuts a vector sequence that represses toxin expression or toxin activity.
3. The method of paragraph 1 or 2, wherein the cutting cuts a vector sequence required for expression or activity of a repressor of toxin expression or toxin activity.
4. The method of any preceding paragraph, wherein the cutting converts a toxin precursor sequence to a sequence encoding the toxin, for expression of the toxin. In the cell; optionally wherein PS1 is comprised by the sequence encoding the toxin or precursor or PS1 is comprised by a regulatory element (eg, promoter or repressor sequence) thereof.
5. The method of any preceding paragraph, wherein the cutting causes expression or increased activity of an activator of the toxin or increased activity of a promoter regulating the sequence encoding the toxin or precursor.
    In an example, the activator is encoded by the first vector.
6. The method of any preceding paragraph, wherein the cutting promotes toxin expression in the cell.
7. The method of paragraph 1, 2 or 5, wherein the first vector comprises a nucleic acid sequence (AT) encoding an anti-toxin, wherein step (d) comprises using Cas nuclease cutting of the first vector in the cell to reduce or eliminate anti-toxin. In the cell, wherein the cutting promotes toxin activity in the cell, whereby the cell is killed.
8. The method of paragraph 7, wherein the cutting inactivates or reduces expression from the nucleic acid sequence encoding the anti-toxin.

9. The method of paragraph 7 or 8, wherein the AT sequence of the first vector comprises or is flanked on one side by a first Cas cutting site; and said sequence (AT) comprises or is flanked on the other side by a second Cas cutting site, each site being in a respective protospacer which is adjacent 5' to a respective PAM, wherein one of the protospacers and respective PAM is PS1 and P1, wherein Cas cutting is used in step (d) to cut the first and second sites, whereby anti-toxin sequence (or promoter sequence) is excised from the first vector and anti-toxin expression from the first vector is reduced or eliminated.

10. The method of paragraph 1, wherein the product of step (c) is a cell that comprises sequence encoding an anti-toxin, wherein the first vector comprises a nucleic acid sequence (AAT) of an anti-antitoxin agent, wherein step (d) comprises using Cas nuclease cutting of the first vector In the cell to increase the agent or increase agent anti-antitoxin activity in the cell, thereby reducing or eliminating anti-toxin expression or activity in the cell, wherein the cutting promotes toxin activity in the cell, whereby the cell is killed.

11. The method of paragraph 10, wherein the anti-toxin is encoded by the cell, eg, encoded by a host cell chromosomal or host episomal (eg, plasmid) nucleotide sequence.

12. The method of paragraph 10, wherein the anti-toxin is encoded by a vector of step (c).

13. The method of any one of paragraphs 10 to 12, wherein the agent is a nucleic acid, eg a DNA.

In an example, the agent (eg, DNA agent fragment) hybridises to the anti-toxin gene (eg, an exon or regulatory element thereof) to inhibit or reduce anti-toxin expression. For example, the DNA fragment comprises one or more regions of homology to sequence in the anti-toxin gene (eg, in a regulatory element or exon thereof), whereby one or more sequences of the DNA fragment are inserted into the anti-toxin gene, thereby inactivating or reducing anti-toxin gene expression (insertion can be with or without deletion of a sequence of the gene). Alternatively, the agent hybridises to mRNA encoding the anti-toxin or a subunit thereof. In an example, the fragment encodes a guide RNA that guides nuclease cutting (eg, Cas cutting) of the anti-toxin gene (eg, an exon or regulatory element thereof) to inhibit or reduce anti-toxin expression. The gRNA may be cognate to an endogenous Cas of the host or may be cognate to a vector-encoded Cas (eg, a Cas9). In an example, where DNA fragment sequence is inserted into the anti-toxin gene, the inserted sequence may encode a toxin that is toxic to the cell or may encode a guide RNA for Cas targeting to the anti-toxin gene or to any other nucleotide sequence in the cell, eg, a host chromosomal or host episomal sequence, eg, the sequence of a host essential, virulence or antibiotic resistance gene. In that way, the anti-toxin (eg, antibiotic) gene is inactivated or activity is reduced by insertion of the DNA fragment sequence and furthermore, the inserted sequence (eg, including a promoter that functions in the cell; or using the endogenous promoter of the anti-toxin gene when the sequence is inserted in functional arrangement with this endogenous promoter) can express a functional guide RNA (eg, a single gRNA) that can be used to modify a further site in the cell (eg, a site whose cutting aids cell killing).

In this and other configurations of the invention, generally there is provided a method comprising Gas cutting of a vector that has been introduced into a cell (eg, prokaryotic or eukaryotic cell) to release a DNA fragment from the vector. In an example, fragment nucleotide sequence is inserted into a host chromosomal or episomal nucleic acid (eg, DNA) (or into an introduced vector) by homologous recombination. In an example, the insertion downregulates (eg, inactivates) or upregulates (eg, activates) a gene of the host nucleic acid. Additionally or alternatively to this, the inserted sequence can express a desirable RNA or encode a desirable protein (eg, a marker to indicate successful production of the DNA fragment and insertion into the host nucleic acid, thereby allowing a further step. In the method of selecting one or more host cells detected using the marker). In another embodiment, the inserted sequence encodes an expressed guide RNA (eg, single guide RNA) in the cell for targeting a respective location. In a host chromosomal or episomal nucleic acid (or alternatively for targeting a sequence in an introduced vector, eg, to modify a gene carried by the vector, such as a selection marker that is up- or down-regulated for providing an indication of successful production of the DNA fragment in the cell by Cas cleavage). Thus, the theme of the invention harnesses Cas cleavage in the cell to release a DNA for homologous insertion into a target sequence, where importantly that insertion up- or down-regulates its target sequence, eg, to provide a marker of successful Cas cleavage and insertion into the target or for incorporation into the target of sequences that have knock-on utility for producing desirable expression products (protein or RNA, eg, gRNA). This expressed gRNA can be employed for further host or vector modification in the cell, eg, for guiding Cas-mediated cutting, activation or inactivation (of host or vector sequence) in the cell. Where the DNA fragment comprises homology arms that target sequence for insertion under the influence of an endogenous regulatory element, this is useful for harnessing endogenous regulatory control (eg, promoter control or enhancer control) to control expression of the inserted sequence, eg, for providing temporal expression of the inserted sequence tuned to the cell (eg, the cell cycle of growth and replication).

14. The method of any one of paragraphs 10 to 12, wherein the agent is a protein.

15. The method of paragraph 13, wherein the first vector is a DNA vector and the AAT sequence of the first vector comprises or is flanked on one side by a first Cas cutting site; wherein said sequence (AAT) comprises or is flanked on the other side by a second Cas cutting site, each site being. In a respective protospacer which is adjacent 5' to a respective PAM, wherein one of the protospacers and respective PAM is PS1 and P1, wherein Cas cutting is used in step (d) to cut the first and second sites, whereby anti-antitoxin agent is released from the first vector and anti-toxin expression in the cell is reduced or eliminated by insertion of anti-antitoxin sequence into a chromosomal or episomal nucleic acid of the host cell, eg, by homologous recombination.

16. The method of paragraph 9 or 15, wherein the first and second sites are cut by the same Cas nuclease species (eg, endogenous Cas or encoded by a vector sequence).
17. The method of paragraph 9 or 15, wherein the first and second sites are cut by different Cas nuclease species (eg, wherein both Cas are endogenous to the cell; one is endogenous and the other encoded by a vector sequence; or both encoded by vector sequences).
18. The method of any one of paragraphs 7 to 17, comprising allowing cut first vector sequence (eg, anti-toxin or AAT sequence) to recombine with a host cell nucleic acid to produce a recombined product in which anti-toxin nucleotide sequence is deleted from the vector.
19. The method of paragraph 18, wherein a host cell sequence is inserted into the vector, eg, to replace the anti-toxin or AAT sequence.
20. The method of paragraph 13 or any one of paragraphs 15 to 19 when dependent on paragraph 13, comprising allowing the DNA agent to recombine with a host cell nucleic acid to produce a recombined product in which agent sequence is inserted into an anti-toxin nucleotide sequence or regulatory element thereof, thereby reducing or eliminating anti-toxin expression or activity.
21. The method of paragraph 20, wherein an anti-toxin nucleotide sequence or regulatory element sequence is deleted from the host cell nucleic acid.
22. The method of any preceding paragraph, wherein the first Cas is guided by a first guide RNA (gRNA1, eg, a single guide RNA) in the cell which hybridises to PS1, whereby the Cas cuts PS1.
    In an example, the sequence encoding gRNA1 is comprised by a vector (eg, the first vector) that is introduced into the cell.
23. The method of paragraph 22, wherein the method comprises providing in the cell before step (d) gRNA1 or a sequence for producing gRNA1 In the cell, optionally wherein the sequence is comprised by the first or another vector introduced into the cell in step (c).
24. The method of any preceding paragraph, wherein the first or each Cas nuclease is endogenous to the cell.
25. The method of any one of paragraphs 1 to 23, wherein the or each Cas nuclease is introduced into the cell before step (d) or a respective nucleotide sequence (eg, comprised by the first vector or another vector) encoding said Cas Is Introduced into the cell.
26. The method of any preceding paragraph, wherein the first or each Cas is a Cas9 (eg, *S. pyogenes* or *S. aureus* Cas9).
27. The method of any one of paragraphs 1 to 25, wherein the first or each Cas is an *E. coli* Cas.
28. The method of any preceding paragraph, wherein the toxin is an antibiotic, eg, an antibiotic medicament.
29. The method of any preceding paragraph, wherein the toxin and anti-toxin are components of a prokaryotic toxin/anti-toxin module, eg, a Type I or II module or a plasmid addiction module.
    For example, the module is a Type I module, eg, a Hok-Sok module. For embodiment, the module is a Type II module, eg, a HiCa-HicB module. For example, the module is a tad-ata-type toxin-antitoxin module. For example, the module is a plasmid addiction module.
30. A method of transforming a host cell, the method comprising
    (a) providing a first nucleic acid vector, the vector being in a first state comprising
        i. a protospacer sequence (PS1) adjacent a PAM (P1) that is cognate to a first Cas nuclease; and
        ii. a first nucleotide sequence comprising a first marker sequence for marking the first state of the vector;
    (b) combining the cell with the vector wherein the vector is introduced into the cell; and
    (c) using Cas nuclease cutting of PS1 of the first vector using the first Cas nuclease, wherein the cutting converts the vector to a second state in which the marker sequence is rendered non-functional; and
    (d) optionally detecting the second state by detecting that the marker is non-functional in the cell.
31. The method of paragraph 30, wherein marker sequence is rendered non-functional by allowing the cut vector to undergo homologous recombination with a chromosomal or episomal nucleic acid of the cell.
32. The method of paragraph 31, wherein vector sequence is inserted into the host nucleic acid.
33. The method of paragraph 31 or 32, wherein a sequence of the host nucleic acid is inserted into the vector.
34. The method of paragraph 33, wherein PS1 and/or P1 is destroyed in the vector by insertion of the host sequence.
35. The method of any preceding paragraph, wherein PS1 and/or P1 is destroyed in the vector by the cutting.
36. The method of any one of paragraphs 30 to 35, wherein the cutting promotes cytotoxic activity of a toxin in the cell, whereby the cell is killed or cell growth or proliferation is reduced.
37. The method of paragraph 36, wherein the toxin is an antibiotic, eg, an antibiotic medicament.
38. The method of any one of paragraphs 30 to 37, wherein the cutting excises marker sequence from the vector, whereby the marker is rendered non-functional.
39. The method of any preceding paragraph, wherein PS1 comprises a target site that is cut by the first Cas, and wherein the target site is at the 5' end of the marker sequence or flanking 5' of the marker sequence.
40. The method of any preceding paragraph, wherein the vector comprises a second protospacer (PS2) and cognate PAM (P2) that is cut in step (c) by the first or a different (second) Cas nuclease, wherein cutting of PS1 and PS2 renders the marker non-functional in the cell.
41. The method of paragraph 40, wherein PS2 comprises a target site that is cut, and wherein the target site is at the 3' end of the marker sequence or flanking 3' of the marker sequence.
42. The method of paragraph 41 when dependent on paragraph 39, wherein the marker sequence is excised from the vector and the vector undergoes gap repair by homologous recombination insertion of a sequence of the host nucleic acid into the vector.
43. The method of paragraph 42, wherein PS1 and/or P1 are destroyed.
44. The method of paragraph 42 or 43, wherein PS2 and/or P2 are destroyed.
45. The method according to any one of paragraphs 33, any one of paragraphs 33 to 44 when dependent upon paragraph 33, or according to any one of paragraphs 42 to 44, wherein the inserted host nucleic acid sequence is a regulatory element, protein-encoding sequence, an exon or a second marker sequence.
46. The method of paragraph 45, wherein the inserted sequence is functional for expression from the vector.

47. The method of paragraph 46, wherein the inserted sequence is a protein-encoding sequence, an exon or a second marker sequence that is inserted in functional arrangement with a vector regulatory element, whereby the regulatory element controls expression of the host sequence from the vector.
48. The method of any one of paragraphs 45 to 47, wherein the host sequence is a second marker sequence, and the method comprises detecting the second marker sequence in the vector; or detecting the second marker, wherein the second marker is not detectable in the cell before step (c) and the second marker sequence is not detectable in the first vector before step (c).
49. The method according to any one of paragraphs 33, any one of paragraphs 34 to 48 when dependent upon paragraph 33, or according to any one of paragraphs 42 to 48, the method comprising using Cas cutting of the host at or flanking one or both ends of said host nucleic acid.
50. The method according to any one of paragraphs 33, any one of paragraphs 34 to 49 when dependent upon paragraph 33, or according to any one of paragraphs 42 to 49, wherein the host nucleic acid sequence is deleted from a host chromosome or episome (eg, plasmid); optionally wherein the deletion from the chromosome or episome is lethal to the cell.
51. The method of any preceding paragraph, wherein the Cas cutting or insertion of host nucleic acid into the vector or first strand down-regulates cell viability, growth or proliferation (eg, kills the cell).
52. The method of any preceding paragraph, wherein the Cas cutting or insertion of host nucleic acid into the vector or first strand up-regulates cell viability, growth or proliferation.
53. The method of any preceding paragraph, wherein, wherein the method is carried out in a host cell, the method comprising isolating the modified cell, modified first vector or first strand and/or modified host chromosomal or episomal nucleic acid in which the host nucleic acid sequence has been deleted by the method.
54. The method of any preceding paragraph, wherein the method is carried out in a bacterial or archaeal cell, eg, an *E. coli* cell.
55. The method of paragraph 54, wherein the cell is of a human pathogen species.
56. The method of paragraph 54 or 55, wherein the cell is a cell of a human microbiome species, eg, a human gut microbiome species.
57. The method of any preceding paragraph for human or animal medical therapy, prophylaxis or diagnosis.
58. The method of any preceding paragraph, wherein the method is carried out in vitro.
59. The method of paragraph 58, wherein the method is a recombineering method.
60. The method of any one of paragraphs 1 to 57, wherein the method is carried out in vivo (eg, but not in a human or human embryo).
61. The method of any one of paragraphs 1 to 57 and 60, wherein the method is carried out in a human (eg, wherein the method is a cosmetic method), embryo (eg non-human embryo), zygote (eg, non-human zygote), germ cell (eg, human or non-human germ cell) or non-human animal.
62. The method of any preceding paragraph, wherein the method is carried out in one or more cells without introducing exogenous Cas or a sequence encoding exogenous Cas into the cells.
63. The method of any preceding paragraph, wherein the method is carried out in a cell and PS1 and P1 are cognate to a Cas that is endogenous to the cell for carrying out the cutting of step.
64. The method of any preceding paragraph, wherein the method is carried out in cells to kill a population of prokaryotic cells, wherein the cells are of the same species or strain.
65. The method of paragraph 64, wherein the population is comprised by a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor).
66. The method of paragraph 64 or 65, wherein the population is comprised by a mixed population of prokaryotic (eg, bacterial) cells and the method selectively kills some but not all cells in the mixed population, wherein the killed cells are cells in which the first vector or first strand was introduced and PS1 cut by a Cas.
67. The method of paragraph 66, wherein the first vector or first strand comprises a sequence encoding a gRNA (gRNA1, eg, a single gRNA) that hybridises to PS1 in the cells or the vector or strand encodes a crRNA that forms gRNA1 in the cells, optionally with a tracrRNA encoded by host cell sequence.
68. The method of paragraph 66 or 67, wherein PS1 and P1 are cognate to a Cas nuclease (eg, an endogenous Cas) of the cells that are killed, but not cognate to cells in the population that are not killed, wherein PS1 is selectively cut in the cells that are killed.
69. The method of any one of paragraphs 66 to 68, wherein the mixed population is a human or non-human animal microbiome population, eg, a gut, vaginal, armpit or oral microbiome population.
70. The method of paragraph 69, comprising isolating the product population of paragraph 69 or a sample of said product.
71. The method of paragraph 70, comprising transplanting said sample or a progeny sample thereof into a human for treating or preventing a disease or condition (eg, obesity).
72. A method of treating or preventing a prokaryotic cell (eg, bacterial) infection in a human or non-human animal subject, the method comprising carrying out the method of any preceding paragraph to kill bacterial cells in the subject, thereby treating or preventing the infection.
73. The method of any preceding paragraph, wherein the first strand or the first or each vector is a dsDNA vector.
74. The method of any preceding paragraph, wherein the first strand or the first or each vector is a ssDNA vector.
75. The method of any preceding paragraph, wherein the first strand or the first vector is circular prior to cutting.
76. The method of any preceding paragraph, wherein the first strand or the first vector is a BAC, PAC, YAC or plasmid.
77. The method of any one of paragraphs 1 to 75, wherein the method is carried out in a bacterial host cell and the first vector is a bacteriophage (or the first strand is comprised by a bacteriophage) that is capable of infecting the host cell for introduction of the first vector or first strand, wherein the vector or strand is introduced into the cell by infecting the cell with the bacteriophage.

78. A first nucleic acid strand (eg, comprised by a vector, eg a retrieval or insertion vector) (optionally for use in any method herein) comprising
    (a) an insert sequence (IS) immediately adjacent to or flanked by a first homology arm (HA1) complementary to a predetermined target nucleotide sequence (NS1) of a second strand for insertion of IS into the second strand by homologous recombination;
    (b) a first protospacer sequence (PS1) adjacent a PAM (P1), wherein P1 is cognate to a first Cas nuclease for cutting PS1 at a first cut site (CS1);
        wherein CS1 is at an end of, or flanking, HA1, wherein when CS1 is cut by Cas HA1 is capable of homologous recombination with NS1 for said insertion of IS.

79. The nucleic acid strand of paragraph 78, wherein CS1 is at the 5' end of HA1.

80. The nucleic acid strand of paragraph 79, wherein P1 is immediately 3' of a seed sequence (S1) of n nucleotides in the first strand (wherein n=3-5 contiguous nucleotides, eg, 3 contiguous nucleotides), wherein 81 joins P1 to CS1 and wherein (I) the 5'-most sequence of n nucleotides (eg, 3 contiguous nucleotides) of NS1 differs from the sequence of S1 and/or (ii) the sequence of 13 contiguous nucleotides immediately 5' of NS1 in the second nucleic acid strand differs from the sequence of 13 contiguous nucleotides immediately 5' of CS1 in the first nucleic acid.
    In an example, in (i) the difference is 1, 2, 3, 4, or 5 or all of said contiguous nucleotides. For example, there is a difference at the 3rd nucleotide of NS1. For example, there is a difference at the 2nd and 3rd, or 3rd and 4th nucleotides of NS1, eg, when S1 is 3 nucleotides in length.
    For example in (ii) the sequences are identical. In sequence except at 3, 4, 5, 6, 7, 8, 9, 10, 11 or 12 or more nucleotides positions.

81. The nucleic acid strand of paragraph 80, wherein the 5'-most nucleotide of NS1 is different from the 5'-most nucleotide of S1; optionally wherein S1 is 3 contiguous nucleotides in length and P1 is cognate to a Cas9 (eg, *S. pyogenes* Cas9).

82. The nucleic acid strand of paragraph 78, wherein CS1 is flanking the 5' end of HA1.

83. The nucleic acid strand of paragraph 78, wherein CS1 is at the 3' end of HA1.

84. The nucleic acid strand of paragraph 83, wherein CS1 is immediately 5' of a seed sequence (S2) of n nucleotides in the first strand (wherein n=3-5 contiguous nucleotides, eg, 3 contiguous nucleotides), wherein S2 joins P1 to CS1 and wherein (i) the sequence n nucleotides (eg, 3 contiguous nucleotides) of the second strand immediately 3' of NS1 differs from the sequence of S2 and/or (ii) the 3'-most sequence of 13 contiguous nucleotides of HA1 differs from the 3'-most sequence of 13 contiguous nucleotides of NS1.

85. The nucleic acid strand of paragraph 84, wherein the 5'-most nucleotide of said second strand sequence of (i) is different from the 5'-most nucleotide of S2; optionally wherein S2 is 3 contiguous nucleotides in length and P1 is cognate to a Cas9 (eg, *S. pyogenes* Cas9).

86. The nucleic acid strand of paragraph 78, wherein CS1 is flanking the 3' end of HA1.

87. The nucleic acid strand of any one of paragraphs 78 to 86, wherein the first strand is not capable of recreating PS1 in combination with P1 when IS inserted into the second nucleic acid strand by recombination of HA1 with NS1.

88. The nucleic acid strand of any one of paragraphs 78 to 87, wherein the first strand is not capable of recreating CS1 when IS inserted into the second nucleic acid strand by recombination of HA1 with NS1.

89. The nucleic acid strand of any one of paragraphs 78 to 88, wherein IS comprises a donor sequence and HA1 is 5' of IS, wherein when CS1 is cut by Cas HA1 is capable of homologous recombination with NS1 for insertion of IS.

90. The nucleic acid strand o of any one of paragraphs 78 to 88, wherein IS comprises a donor sequence and HA1 is 3' of IS, wherein when CS1 is cut by Cas HA1 is capable of homologous recombination with NS1 for insertion of IS.

91. The nucleic acid strand of paragraph 89 or 90, wherein the first nucleic acid comprises a further protospacer and cognate PAM, wherein one or both of the further protospacer and PAM are comprised by IS.

92. The nucleic acid strand of paragraph 91, wherein the further PAM is cognate to a Cas that is different from the Cas that is cognate to P1.

93. The nucleic acid of any of paragraphs 89 to 92, wherein IS comprises a sequence encoding a regulatory element, a protein-encoding sequence, an exon or a marker sequence.

94. The nucleic acid strand of any one of paragraphs 78 to 93, wherein IS comprises
    (e) a second homology arm (HA2) complementary to a second predetermined sequence (NS2) of the second strand;
    (f) a second protospacer sequence (PS2) adjacent a second PAM (P2), wherein P2 is cognate to a Cas nuclease for cutting PS2 at a second cut site (CS2);
        wherein when CS2 is cut by Cas HA2 is capable of homologous recombination with NS2 for insertion of IS.

95. The nucleic acid strand of paragraph 94, wherein P2 is cognate to the first Cas.

96. The nucleic acid strand of paragraph 94 or 95, wherein HA1 and HA2 are capable of insertion together without any sequence between HA1 and HA2, and optionally without insertion of any sequence flanking HA1 and HA2 in the first nucleic acid strand.

97. The nucleic acid strand of paragraph 94, 95 or 96, wherein NS1 and NS2 are spaced apart in the second nucleic acid strand, wherein HA1 and HA2 are capable of being inserted into the second strand to delete sequence between NS1 and NS2.

98. The nucleic acid strand of paragraph 94, 95 or 96, wherein NS1 and NS2 are not spaced apart in the second nucleic acid strand, wherein HA1 and HA2 are capable of being inserted into the second strand without deleting sequence between NS1 and NS2.

99. The nucleic acid strand of any one of paragraphs 94 to 98, wherein IS comprises a donor sequence between HA1 and HA2.

100. The nucleic acid strand of paragraph 99, wherein the first nucleic acid comprises a further protospacer and cognate PAM, wherein one or both of the further protospacer and PAM are comprised by IS.

101. The nucleic acid strand of paragraph 100, wherein the further PAM is cognate to a Cas that is different from the Cas that is cognate to P1.
102. The nucleic acid strand of paragraph 100 or 101, wherein the further PAM is cognate to a Cas that is different from the Cas that is cognate to P2.
103. The nucleic acid of any of paragraphs 94 to 102, wherein IS comprises a sequence encoding a regulatory element, a protein-encoding sequence, an exon, a predetermined restriction endonucleases site, an additional Cas cutting site or a marker sequence.
104. The nucleic acid strand of any one of paragraphs 94 to 103 when dependent from paragraph 79 or 82, wherein CS1 is immediately 3' of a sequence (TS1) in the first nucleic acid strand, wherein P2 is immediately 3' of a seed sequence (S2') in the first strand, wherein S2' Joins P2 to CS2, wherein the sequence TS1-S2 is not a further protospacer cognate to P2, wherein TS1-S2 is capable of being formed upon recombination of HA1 with NS1 and recombination of HA2 with NS2 and deletion of the sequence between CS1 and CS2 from the strand, whereby TS1-S2 Is not capable of being cut by Cas cognate to P2.
105. The nucleic acid strand of any one of paragraphs 94 to 103 when dependent from paragraph 79 or 82, wherein CS1 is immediately 3' of a sequence (TS1) in the first nucleic acid strand, wherein P2 is immediately 3' of a seed sequence (S2') in the first strand, wherein S2' Joins P2 to CS2, wherein the sequence TS1-S2 Is a further protospacer (PS3) cognate to P2, wherein PS3 is capable of being formed upon recombination of HA1 with NS1 and recombination of HA2 with NS2 and deletion of the sequence between CS1 and CS2 from the strand.
106. The nucleic acid strand of any one of paragraphs 78 to 105, wherein P1 is immediately 3' of a seed sequence (S1), wherein S1 Joins P1 to CS1, wherein IS is capable of insertion into the second nucleic acid strand to form a protospacer (PS4) cognate to P1, wherein PS4 comprises S1 at its 3' end and second strand nucleic acid sequence at its 5' end.
107. The nucleic acid strand of any one of paragraphs 78 to 106, wherein the strand is comprised by a multi-copy vector that is capable of transforming a cell.
108. The nucleic acid strand of any one of paragraphs 78 to 107, wherein the strand is in combination with a guide RNA (gRNA1, eg, a single guide RNA) or an expressible nucleotide sequence for producing gRNA1 in vitro or In a cell, wherein gRNA1 comprises a nucleotide sequence complementary to PS1 for guiding Cas to cut PS1.
   gRNA1 Is cognate to PS1, P1 and the first Cas for guiding the Cas to PS1 for cutting PS1.
109. The nucleic acid strand of any one of paragraphs 78 to 108 when dependent from paragraph 94, wherein the strand is in combination with a guide RNA (gRNA2, eg, a single guide RNA) or an expressible nucleotide sequence for producing gRNA2 in vitro or in a cell, wherein gRNA2 comprises a nucleotide sequence complementary to PS2 for guiding Cas to cut PS2.
   gRNA1 is cognate to PS2. P2 and the Cas for guiding the Cas to PS2 for cutting PS2.
110. The nucleic acid strand of any one of paragraphs 78 to 109 when dependent from paragraph 105, wherein the strand is in combination with a guide RNA (gRNA3, eg, a single guide RNA) or an expressible nucleotide sequence for producing gRNA3 in vitro or in a cell, wherein gRNA3 comprises a nucleotide sequence complementary to PS3 for guiding Cas to cut PS3.
   gRNA1 is cognate to PS3. P3 and the Cas for guiding the Cas to PS3 for cutting PS3.
111. The nucleic acid strand of any one of paragraphs 78 to 110 when dependent from paragraph 130, wherein the strand is in combination with a guide RNA (gRNA4, eg, a single guide RNA) or an expressible nucleotide sequence for producing gRNA4 in vitro or in a cell, wherein gRNA4 comprises a nucleotide sequence complementary to PS4 for guiding Cas to cut PS4.
   gRNA1 is cognate to PS4, P4 and the Cas for guiding the Cas to PS4 for cutting PS4.
112. The nucleic acid strand of any one of paragraphs 108 to 111, wherein the or each nucleotide sequence for producing a gRNA is a nucleotide sequence encoding a crRNA comprising a sequence complementary to the respective PS.
113. The nucleic acid strand of paragraph 112 in combination with a tracrRNA or an expressible nucleotide sequence for producing a tracrRNA, wherein the tracrRNA comprises a sequence that is complementary to a sequence of the crRNA, and wherein the guide RNA comprises sequences of said crRNA and tracrRNA.
114. The nucleic acid strand of any one of paragraphs 78 to 113, wherein the strand is in combination with said second strand.
115. The nucleic acid strand of any one of paragraphs 78 to 114, wherein the first strand or said combination is in a host cell.
116. The nucleic acid strand of paragraph 115 when dependent from paragraph 112, wherein the host cell expresses a tracrRNA, wherein the tracrRNA comprises a sequence that is complementary to a sequence of the crRNA, and wherein the guide RNA comprises sequences of said crRNA and tracrRNA.
117. The nucleic acid strand of paragraph 115 or 116, wherein the cell is a bacterial or archaeal cell, eg, an E co/1 cell.
118. The nucleic acid strand of paragraph 117, wherein the cell is of a human pathogen species.
119. The nucleic acid strand of paragraph 117 or 118, wherein the cell is a cell of a human microbiome species, eg, a human gut microbiome species.
120. The nucleic acid of any one of paragraphs 78 to 119 for human or animal medical therapy, prophylaxis or diagnosis.
121. The nucleic acid of any one of paragraphs 78 to 120 in vitro.
122. The nucleic acid of any one of paragraphs 78 to 121 in combination with recombineering reagents.
123. The nucleic acid of any one of paragraphs 78 to 120 in vivo (eg, but not in a human or human embryo).
124. The nucleic acid of any one of paragraphs 78 to 123, wherein the first nucleic acid is comprised by a first vector.
125. The nucleic acid of any one of paragraphs 78 to 124 when dependent on any one of paragraphs 108 to 113, wherein the first nucleic acid and sequence(s) encoding said gRNA(s) are comprised by a first vector or combination of vectors.
126. The nucleic acid of paragraph 113, wherein the nucleic acid encoding tracrRNA is comprised by said first vector or vector combination.

127. The nucleic acid of any one of paragraphs 125 to 126, wherein the first nucleic acid and said sequence encoding gRNA1 (and optionally the sequence encoding gRNA2) are comprised by said first vector.
128. A first vector according to paragraph 124 in combination with a second vector, wherein the second vector comprises and said sequence encoding gRNA1 (and optionally the sequence encoding gRNA2).
129. The vector combination of paragraph 128, wherein the second vector comprises an expressible nucleotide sequence encoding said first Cas (eg, a Cas9).
130. The vector combination of paragraph 128, in combination with a third vector which comprises an expressible nucleotide sequence encoding said first Cas (eg, a Cas9).
131. The vector combination of paragraph 128, wherein the first vector comprises an expressible nucleotide sequence encoding said first Cas (eg, a Cas9).
132. The nucleic acid or combination of any one of paragraphs 78 to 131 when dependent on any one of paragraphs 108 to 113, wherein gRNA1 and gRNA2 are transcribed from the same promoter, wherein the nucleotide sequences encoding gRNA1 and gRNA2 are comprised by said first vector or a common vector of said combination.
133. The nucleic acid or combination of any one of paragraphs 78 to 132, wherein the nucleic acid or combination is comprised by a cell comprising an endogenous CRISPR/Cas system and P1 is cognate to a Cas nuclease of said system for cutting PS1.
134. The nucleic acid or combination of any one of paragraphs 78 to 133 in combination with said first Cas, or an expressible nucleotide sequence encoding said Cas nuclease.
135. The nucleic acid or combination of any one of paragraphs 78 to 134, wherein HA1 and HA2 are capable of hybridising to unique sequences (NS1 and NS2) of a single strain or species of bacterium.
136. The nucleic acid or combination of paragraph 135, wherein said bacterial species or strain is found. In a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor); optionally wherein the nucleic acid or combination is in combination with any of these.
137. The nucleic acid or combination of paragraph 135 or 136, wherein the species or strain is a human or non-human animal microbiome species or strain, eg, a gut, vaginal, armpit or oral microbiome population.
138. An antibiotic (eg, anti-bacterial or anti-archaeal) composition comprising the first nucleic acid or combination of any one of paragraphs 78 to 137.
139. A medicament for treating or preventing a disease or condition (eg, a bacterial infection or obesity) In a human, the medicament comprising the first nucleic acid, antibiotic or combination of any one of paragraphs 78 to 138.
140. The nucleic acid of paragraph 124, or nucleic acid or combination of any one of paragraphs 125 to 139 when dependent from paragraph 124, wherein the first or each vector is a dsDNA vector.
141. The nucleic acid of paragraph 124, or nucleic acid or combination of any one of paragraphs 125 to 139 when dependent from paragraph 124, wherein the first or each vector is a dsDNA vector.
142. The nucleic acid or combination of paragraph 140 or 141, wherein the first vector or each vector is a BAC, PAC, YAC or plasmid.
143. The nucleic acid or combination of paragraph 140, 141 or 142, wherein the first vector is circular prior to cutting.
144. The nucleic acid of paragraph 124, or nucleic acid or combination of any one of paragraphs 125 to 139 when dependent from paragraph 124, wherein the first vector is a bacteriophage that is capable of infecting a host cell for introduction of the first vector and cutting PS1 therein.
145. The method, nucleic acid, combination, antibiotic or medicament of any preceding paragraph, wherein HA1 is spaced no more than 250 nt away from CS1.
146. The method, nucleic acid, combination, antibiotic or medicament of any preceding paragraph, wherein HA1 comprises at least 15 contiguous nucleotides.
147. The method, nucleic acid, combination, antibiotic or medicament of any preceding paragraph, wherein the sequence of HA1 is isogenic to NS1.
148. The method, nucleic acid, combination, antibiotic or medicament of any preceding paragraph, wherein HA2 is spaced no more than 250 nt away from CS2.
149. The method, nucleic acid, combination, antibiotic or medicament of any preceding paragraph, wherein HA2 comprises at least 15 contiguous nucleotides.
150. The method, nucleic acid, combination, antibiotic or medicament of any preceding paragraph, wherein the sequence of HA2 Is isogenic to NS2.
151. A method of making a first nucleic acid strand suitable for homologous recombination with a second nucleic acid strand, the method comprising combining in a nucleic acid strand
   (a) an insert sequence (IS) comprising (or consisting of) a first homology arm (HA1) complementary to a predetermined target nucleotide sequence (NS1) of the second strand for insertion of IS into the second strand by homologous recombination;
   (b) a first protospacer sequence (PS1) adjacent a PAM (P1), wherein P1 is cognate to a first Cas nuclease for cutting PS1 at a first cut site (CS1);
wherein CS1 is at an end of, or flanking, HA1, wherein when CS1 is cut by Cas HA1 is capable of homologous recombination with NS1 for said insertion of IS.
152. The method of paragraph 151, the method comprising further combining in the nucleic acid strand
   (c) a second homology arm (HA2) complementary to a second predetermined sequence (NS2) of the second strand;
   (d) a second protospacer sequence (PS2) adjacent a second PAM (P2), wherein P2 is cognate to a Cas nuclease for cutting PS2 at a second cut site (CS2);
wherein when CS2 is cut by Cas HA2 is capable of homologous recombination with NS2 for insertion of IS.
153. The method of paragraph 151 or 152, the method comprising cutting CS1 with the first Cas (eg, a Cas9, optionally *S. pyogenes* or *S. aureus* Cas9).
154. The method of paragraph 152 or 153, the method comprising cutting CS2 with the Cas nuclease that is cognate to P2.
155. The method of paragraph 154 the method comprising cutting CS1 and CS2 with the same Cas nuclease.

156. The method of any one of paragraphs 153 to 155, the method comprising carrying out homologous recombination between HA1 (and optionally also HA2) with the second nucleic acid strand, wherein IS is inserted into the second strand; and optionally isolating or sequencing the modified second nucleic acid strand and/or the first nucleic acid strand after said homologous recombination.

157. A method of modifying a nucleic acid strand, the method comprising
   (a) providing a first nucleic acid strand according to any one of paragraphs 78 to 150 or a first nucleic acid strand produced by the method of any one of paragraphs 151 to 156;
   (b) cutting CS1 with the first Cas (eg, a Cas9, optionally S. pyogenes or S. aureus Cas9); and
   (c) carrying out homologous recombination between HA1 (and optionally also HA2) with a second nucleic acid strand, wherein IS is inserted into the second strand; and
   (d) optionally isolating or sequencing the modified second nucleic acid strand and/or the first nucleic acid strand after said homologous recombination, 158. The method of paragraph 157, wherein the method comprises cutting (eg, using Cas cutting) the second nucleic acid strand between NS1 and NS2 prior to said homologous recombination.

159. The method of paragraph 158, wherein the cutting of the second nucleic acid strand is cut with the first Cas nuclease.

160. The method of any one of paragraphs 157 to 159, wherein a marker comprised by the first or second nucleic acid strand is destroyed by said homologous recombination, the method comprising detecting the absence of said marker to determine that homologous recombination has taken place.

161. The method of any one of paragraphs 157 to 159, wherein a marker comprised by the first or second nucleic acid strand is formed by said homologous recombination, the method comprising detecting the presence of said marker to determine that homologous recombination has taken place.

162. The method of any one of paragraphs 157 to 161, wherein IS comprises a donor sequence and HA1 is 5' of IS, wherein the method comprises carrying out homologous recombination between HA1 and NS1 wherein IS is inserted into the second nucleic acid sequence.

163. The method of paragraph 162, wherein a further protospacer and PAM are comprised by IS and the method comprises using Cas cutting of the further protospacer after insertion of IS into the second nucleic acid strand, wherein the further protospacer is cut at a cut site CS3.

164. The method of paragraph 163, wherein a Cas that is not cognate to P1 or P2 is used for cutting the further protospacer.

165. The method of paragraph 163 or 164, comprising carrying out homologous recombination to insert or delete a further sequence at or flanking CS3.

166. The method of any one of paragraphs 157 to 165, the method comprising inserting HA1 and HA2 into the second nucleic acid strand without inserting any sequence between HA1 and HA2, and optionally without insertion of any sequence flanking HA1 and HA2 in the first nucleic acid strand.

167. The method of any one of paragraphs 157 to 166, the method comprising deleting sequence between NS1 and NS2.

168. The method of paragraph 167, wherein the method is carried out in a cell (eg, a bacterial cell, eg, a human pathogen cell) and the second nucleic acid strand is comprised by a chromosome or episome of the cell, wherein the sequence deletion kills the cell.

169. The method of any one of paragraphs 157 to 166, the method comprising inserting IS without deleting sequence between NS1 and NS2.

170. The method of any one of paragraphs 157 to 169, the method comprising before cutting CS1 combining the first nucleic strand with a guide RNA (gRNA1, eg, a single guide RNA), wherein gRNA1 comprises a nucleotide sequence complementary to PS1 for guiding Cas to cut PS1.

171. The method of any one of paragraphs 157 to 170, the method comprising before cutting CS1 combining the first nucleic acid with a guide RNA (gRNA2, eg, a single guide RNA), wherein gRNA2 comprises a nucleotide sequence complementary to PS2 for guiding Cas to cut PS2.

172. The method of any one of paragraphs 157 to 171, wherein the first strand is comprised by a first vector and before cutting CS1 the method comprises introducing the vector into a host cell, wherein CS1 is cut in the host cell and homologous recombination with the second strand is carried out in the host cell.

173. The method of paragraph 172, wherein the cell is a bacterial or archaeal cell, eg, an E. coli cell.

174. The method of paragraph 172 or 173, wherein the cell is of a human pathogen species.

175. The method of paragraph 172, 173 or 174, wherein the cell is a cell of a human microbiome species, eg, a human gut microbiome species.

176. The method of any one of paragraphs 173 to 175, wherein the first Cas (eg, a Cas9) is endogenous to the cell.

177. The method of any one of paragraphs 157 to 176, comprising introducing the first Cas into the cell before cutting CS1 or introducing into the cell an expressible nucleotide sequence encoding the first Cas and further expressing said Cas in the cell before cutting CS1.

178. The method of any one of paragraphs 157 to 177 in vitro.

179. The method of any one of paragraphs 157 to 178, wherein the method comprises recombineering to modify the nucleic acid strands.

180. The method of any one of paragraphs 157 to 177 in vivo (eg, but not in a human or human embryo).

181. The method of any one of paragraphs 157 to 177 and 180, for human or animal medical therapy, prophylaxis or diagnosis, wherein a disease or condition. In the human or animal is treated, prevented or diagnosed.

182. The method of paragraph 172, wherein the cell is a eukaryotic cell.

183. The method of paragraph 182, comprising introducing the first Cas into the cell before cutting CS1 or introducing into the cell an expressible nucleotide sequence encoding the first Cas and further expressing said Cas in the cell before cutting CS1.

184. The method of any one of paragraphs 157 to 183, comprising further including the first nucleic acid into a foodstuff, food ingredient or precursor ingredient; beverage; water (eg, intended for human consumption); an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor).

185. The method of any one of paragraphs 157 to 184, comprising further including the first nucleic acid into a composition for introducing the nucleic acid into a bacterial or archaeal species or strain that is a human or non-human animal microbiome species or strain, eg, a gut, vaginal, armpit or oral microbiome population.

186. The method of any one of paragraphs 157 to 185, comprising further including the first nucleic acid into an antibiotic (eg, anti-bacterial or anti-archaeal) composition or into a medicament for treating or preventing a disease or condition (eg, a bacterial infection or obesity) in a human.

187. The method of any one of paragraphs 157 to 183, wherein the method is carried out in a cell and cutting of CS1 kills the cell or reduces cell growth or proliferation.

188. The method of paragraph 187, wherein PS1 is comprised by a vector anti-toxin nucleotide sequence and/or the anti-toxin sequence is deleted from the first strand by said homologous recombination.

189. The method of paragraph 188, wherein PS1 is comprised by or flanking a nucleic acid sequence (AAT) of an anti-antitoxin agent of the first strand, wherein the agent is capable of eliminating or reducing activity of a host cell anti-toxin.

190. The method of any one of paragraphs 157 to 183 and 187 to 189, wherein the method is carried out in a cell and cutting of CS1 promotes the cytotoxic activity of a toxin in the cell.

191. The method of any one of paragraphs 157 to 190, wherein the first nucleic acid is according to any one of paragraphs 78 to 150.

192. A method of modifying a nucleic acid in a cell (eg, a prokaryotic or eukaryotic cell), the method comprising
 (a) Providing a cell containing
   i. a closed circular nucleic acid vector (eg, a BAC), wherein the vector comprises a first nucleic acid strand;
   ii. a second nucleic acid strand, wherein the second strand is comprised by a chromosome of the cell; and
   iii. a nucleotide sequence encoding a Cas nuclease and optionally a nucleotide sequence encoding a nuclear localisation signal (NLS);
 (b) Using Cas (eg, Cas9) nuclease cutting to cut the first strand of the vector inside the cell to produce recombinogenic vector nucleic acid; and
 (c) Using homologous recombination inside the cell between the cut first strand and the second strand and exchanging a sequence of at least 10, 20, 30, 40, 50, 60, 70, 80, 90, 100, 150, 200, 250 or 300 kb of contiguous nucleotides between the first and second strands, thereby forming at least one modified strand; and
 (d) Optionally isolating or sequencing a modified strand or the cell.

193. The method of paragraph 192, wherein a homology arm in the first strand is used for said homologous recombination, and the Cas cutting cuts the strand no more than 1 kb away from the homology arm.

194. The method of paragraph 192 or 193, wherein at least 0.5 kb of homology is used for said homologous recombination.

195. The method of any one of paragraphs 192 to 194, wherein the exchange comprises homology-directed repair (HDR) of the first or second strand.

196. The method of any one of paragraphs 192 to 194, wherein the second strand is not cut.

197. The method of any one of paragraphs 192 to 196, wherein said sequence is a sequence of at least 100 kb of contiguous nucleotides.

198. The method of any one of paragraphs 192 to 197, wherein the vector is introduced into the cell before step (a) as a supercoiled closed circular vector.

199. The method of any one of paragraphs 192 to 198, wherein the cell is a human, mouse, plant or yeast cell.

200. The method of any one of paragraphs 192 to 199, wherein said sequence is a human sequence.

201. The method of any one of paragraphs 192 to 200, wherein said sequence is retrieved from the second strand and inserted into the first strand.

202. The method of any one of paragraphs 192 to 201, wherein said sequence is inserted from the first strand into the second strand.

203. A gene therapy method for correcting a mutation in a human cell in vitro, the method comprising carrying out the method of any one of paragraphs 192 to 202 in a human cell (eg, PS cell or T-cell) to correct said mutation, wherein the mutation is comprised by the second strand in step (a).

204. A method of producing a human CAR-T cell, the method comprising carrying out the method of any one of paragraphs 192 to 203 in a human T-cell (or precursor cell thereof), wherein said sequence is a sequence for expressing a protein, subunit or domain of a Chimaeric Antigen Receptor.

In an example the first strand in the method of any one of paragraphs 192 to 204 has the features of the first strand as recited in any configuration, embodiment, example or clause of the invention, thereby any of those features are combinable with any of paragraphs 192 to 204. In an example the second strand in the method of any one of paragraphs 192 to 204 has the features of the donor or further strand as recited in any configuration, embodiment, example or clause of the invention, thereby any of those features are combinable with any of paragraphs 192 to 204.

In any configuration herein, HA1 and HA1 are from the same species or strain as the cell in which the method is performed (ie, the same species or strain of NS1 and NS2). For example, the species is human, mouse or rat, eg, mouse 129 or C57/BL6 strain.

In configurations where the vector product comprises the first strand containing RS retrieved from a donor strand, the product vector optionally comprises nuclease (eg, Cas) cutting sites flanking 3' and 5' respectively HA1 and HA2 (or at or flanking the 3' and 5' ends respectively of HA1 and HA2) for enabling production of an sequence with recombinogenic ends and comprising RS for subsequent HR or SSR insertion of RS into a further strand, eg, of a target cell or nucleic acid. In an example, the additional cutting sites are cut with a Cas nuclease that is different to the Cas(es) used to cut CS1 and CS2 and/or gRNA(s) for cutting the additional sites are combined with the first strand (eg, introduced into the cell where RS was retrieved) after first cutting CS1/CS2.

Sequence Libraries, Collections & Uses

The invention is useful for producing collections or libraries of retrieved sequences (RSs). In an embodiment, the invention finds utility in producing a plurality of vectors obtainable (or obtained) by the retrieval method of the invention and comprising a collection of retrieved sequences (RSs), wherein the collection comprises first and second RS sequences that are different from each other, eg, encode a plurality of proteins that are variants of each other. In an embodiment, the total size of the first and second RSs is from 1 to 600 kb, eg, from 1 to 500, 400, 300, 200, 250, 150 or 100 kb and optionally each sequence is no more than 250 or 300 kb in size. For example, the vectors are BAC or YAC vectors comprising a collection of genomic fragments retrieved from a cell sample. The sample may comprise a plurality of cells of the same or different type, eg, cells that are obtained from the same organism, such as a rodent, mouse, rat, human, bacterial species or strain, yeast species or strain or wherein the sequences are of the same viral species or strain. In an example, the invention is useful for producing a vector collection comprising a plurality of retrieved genomic fragments of the genome of a human or animal. In this way, the invention readily provides means to produce personalized collections for individual humans, which may for example be useful for sequencing all or part of the human's genome and/or as a source of one or more genomic fragments for use for diagnostic, therapeutic and/or prophylactic use in the human or in humans, such as use as a sequence source for insertion into cells for producing transgenic cells for said diagnostic, therapeutic or prophylactic use. For example, one or more retrieved sequences (RSs) Is sequenced, isolated and/or copied from a vector of the invention and used in a method wherein the sequence (or a modified or corrected version thereof) is inserted into a recipient cell in vitro, and optionally the cell is administered to an animal (eg, a human or animal patient) for treating or preventing a disease or condition in the patient or the cell is developed into a tissue or blood sample for said administration. The recipient cell may be a human or animal pluripotent cell (eg, a human iPS cell), stem cell, embryonic stem cell (eg, non-human vertebrate cell, eg, a rodent, rat or mouse ES cell) or an immune cell (eg, a human immune cell or haemopoletic stem cell). In this way, for example, a modified human immune cell (eg, a CAR-T or NK cell) can be produced that is administered to a human patient for treating or preventing a disease or condition in the patient.

By using relatively small homology arms. In the retrieval vector (eg, as small as 15-50 bp) and/or by using arms whose sequences have several mismatches with the donor nucleic acid (eg, where the sequence of each arm comprises from 40 to 20% mismatches with its respective NS1 or 2) this may be useful for retrieving random (non-predetermined or unknown) RS from the donor, eg, to produce a collection of random genomic fragments from one or more cells of an organism (eg, a human, rodent, mouse or rat).

Advantageously, a vector of the invention comprises RS flanked by one or more homology arms of known sequence (HA1 and HA2 for example). This provides several advantages. For example, the homology arms can be used to insert RS into a recipient cell (eg, a cell mentioned herein), advantageously the insertion being at the predefined genomic location dictated by the homology arms. Usefully, the homology arms are provided in combination with the RS by the method of the invention without the need for further, labourious cloning or other steps to add homology arms before the RS is ready for homologous recombination insertion into a recipient cell.

Vectors of the invention, each comprising a RS flanked by one or more homology arms of known sequence is also useful for producing libraries or collections of genomic fragments (RSs), such as collections of sequences from a plant, animal (eg, human, rodent, mouse or rat), yeast, bacterial or viral genome. In an embodiment, this is useful for producing a sequence library, eg, a mammal (eg, human or mouse) library, which can be readily catalogued or ordered. Reference genome sequences (eg, human, bacterial, mouse or yeast reference genome sequence(s)) are available in the art, these can be used to select a plurality of different HA1/HA2 pairs, each pair being used to construct a respective type of retrieval vector (first strand of the invention). Such plurality of vectors are then combined with one or more cells obtained from a respective organism (eg, plant, animal (eg, human, rodent, mouse or rat), yeast or bacterial cells) and used in the method of the invention to retrieve a plurality of RSs (different RSs being retrieved owing to the use of different HA1/HA2 pairs in the vectors). In an embodiment, at least first and second retrieval vectors are introduced into the same cell, wherein the vectors comprise different HA1/HA2 pairs, wherein first and second different RS are retrieved from a chromosome or episome of the cell. Additionally or alternatively, the plurality of different retrieval vectors are combined with a plurality of cells (eg, obtained from the same organism or of the same species or strain, eg, of bacteria or yeast or from the same organ or tissue), wherein the vectors are introduced into the cells and a plurality of RSs are retrieved from the cells. In an embodiment, one or a plurality of the retrieved RSs are isolated, sequenced or copied from the vectors. The RSs can be used in one or more of the further applications (eg, for gene therapy) as disclosed herein.

Advantageously, as the HA1/HA2 pairs can be designed using knowledge of a reference sequence (eg, genomic or chromosomal sequence of an individual (eg, a human) or species), the relative genomic or chromosomal order or location of the HA1/HA2 pairs will be known and this makes it possible for the retrieval vectors (comprising their respective RSs) to be ordered or catalogued or labeled with reference to the known order or location. In the reference genome. This allows for automation or computer-aided compilation of a library catalogue or database. Thus, for example, it is possible to determine which two vectors comprise RSs that are overlapping, adjacent, contiguous, on the same chromosome and/or comprised by the same locus in the genome of the organism from which the initial sample of cells was obtained. This greatly simplifies the assembly of an ordered or catalogued vector library of genomic sequences of an organism or cell. In an embodiment, the vectors can be uniquely labeled (eg, by comprising one or more conventional nucleotide sequence barcodes) that identify the known location, chromosome or order in the reference genome sequence(s). This is useful, for example, for high throughput sequencing using a Next Generation Sequencing method, such as using MiSeq™. In an example, one or both of HA1 and HA2 of each vector comprises a barcode identifier (and restriction or nuclease sites (eg, Cas cutting sites) can optionally be included flanking or in the barcodes or the homology arms to allow for release or RSs once identification has taken place). By using different barcodes to identify different locations (with reference to a reference sequence or genome), each type of RS that is retrieved can be identified and correlated with its respective vector and location in the reference. For example, the invention comprises using the barcodes or identifiers to sort the retrieved sequences and to order the sequences (eg, in silco to compile a sequence compilation comprising a plurality of the retrieved sequences ordered according to an order ascribed with reference to a reference genome sequence, eg, a human, mouse, yeast or bacterial reference sequence as appropriate). This is much simpler than current techniques that involve shearing whole genomic DNA from cells in vitro (which further reduces the range and sizes of fragments that can usefully be gathered), purifying and isolating individual sequences, adding adaptor ends (eg, using PCR or Gibson assembly in vitro) to the sequences and then cloning the modified sequence fragments into a plurality of vectors (such as BACs) to create a library. In this case, many laborious steps are used—including harmful shearing of sequences which causes damage and lowers efficiency of the method and limits the size of obtained fragments. Furthermore, ordering, identifying or cataloguing of the vectors then requires sequencing of the many vector inserts which is time consuming, followed by such ordering etc on the basis of such information. The invention, in embodiments, is superior as large fragments can be captured in retrieval vectors inside the less harsh environment of a cell, the capture being directly into a vector (such as a circular vector) that is directly useful for downstream use without further manipulation, the location of the RS in the donor sequence is known (and can be easily identified and catalogued as discussed above), and the RS is usefully flanked by known sequences that can be used is identifier sequences (to aid identification of the RS) and/or for downstream insertion (eg, by homologous recombination) into recipient sequences or cell genomes. The invention usefully avoids the need to rely on PCR to retrieve sequences and to process nucleic acid for insertion into vectors; thus the possibility of PCR-derived nucleotide sequence errors (eg, insertion, deletion and/or substitution of one or more nucleotides that erroneously changes the donor RS sequence) is avoided with the present invention. The product vector and RS of the invention is directly useful, therefore, without need for any PCR steps and also without need for expansion or culturing steps (although retrieved RS vector expansion or culturing can be included in the method if desired). The invention can be multiplexed so that multiple RS retrievals can be made by simply combining a plurality of different retrieval vectors with a donor sequence sample (eg, a cell population). The invention is also easily operated as it can employ a single type of retrieval vector precursor (universal vector). The universal vector can be designed to include one or more cloning sites for insertion of homology arm(s) that are selected to target a desired and predetermined area of a target cell genome or target nucleic acid. The universal vector is provided with one or more cutting sites, each flanking or immediately adjacent to a respective site ("cloning site") for insertion of a homology arm. Embodiments of this are described herein with reference to Cas cutting, but can be readily modified for cutting with different means, such as guided nuclease (eg, RNA guided nuclease) or restriction endonuclease.

In an embodiment, the invention provides a collection of vectors (eg, circular vectors) comprising a plurality of different sequences of an animal genome, organ or tissue, wherein each sequence has been obtained or copied from an RS retrieved using the method of the invention. In an example, the animal is a human or a rodent, rat or mouse. In an alternative, the collection comprises such sequences of a plurality of animals of the same species (eg, of a one, two or more humans). In an example, the sequences comprised by said plurality are associated with identifiers (eg, nucleotide sequence tags or barcodes) to identify the respective sequences, eg, to identify one, more or all of the source (eg, the human) of the sequence, the genomic location and the chromosomal location.

As explained above, the choice of which RS sequences are to be retrieved is easily controlled by the choice of homology arms in the present invention. In this way, first and second RSs can be retrieved that are adjacent to each other, contiguous with each other, or which overlap in the donor sequence, eg, in the donor cell or organism genome. Optionally, a third RS is retrieved, wherein the third RS is adjacent to, contiguous with or overlaps the first or second RS in the donor cell or organism genome. By retrieving (and optionally identifying, ordering or cataloguing) a plurality of RSs in this way, it is possible to walk along a donor chromosome or episome with a relatively few steps using relatively large sequence fragments (especially wherein the RSs are retrieved into circular vectors, such as BACs or YACs). For example, this is especially facilitated when the plurality of retrieved RSs comprises RSs that are overlapping and/or RSs that are contiguous in the donor. In an embodiment, retrieved RSs comprises RSs that are overlapping or that are contiguous in the donor are useful in a method of producing an engineered sequence (eg, DNA sequence) or cell genome (eg, an PS or ES cell genome). To this end, the invention provides a method of producing an engineered sequence (eg, DNA sequence) or cell genome in vitro, wherein the method comprises (a) providing a recipient nucleic acid sequence (eg, a DNA sequence, eg, comprised by said cell); (b) inserting a first insert sequence into (or at an end of) the recipient sequence; (c) inserting a second insert sequence into (or at the end of) the first insert sequence such that the insert sequences partially overlap or are immediately contiguous and (d) isolating a sequence or genome or cell comprising the first and second insert sequences; and optionally (d) producing a tissue or a non-human vertebrate from the resultant cell; wherein the first insert sequence comprises the sequence of a first RS that has been retrieved into a vector using the method according to the invention; wherein the second insert sequence comprises the sequence of a second RS that has been retrieved into a vector using the method according to the invention, and wherein the RSs are immediately contiguous or partially overlapping in a donor sequence that was used for said retrieval in the method of the invention. In an example, each said insert sequence comprises respective spaced first (HA1) and second (HA2) homology arms joined by a sequence (RS), wherein HA2 of the first insert sequence is 3' of the RS of the first insert sequence, HA1 of the second insert sequence is 5' of the RS of the second insert sequence, and the HA1 of the second insert sequence is identical to the HA2 of the first insert sequence or partially overlaps therewith or is comprised by the RS of the first insert sequence or HA1 of the second insert sequence comprises a sequence that is at least 90, 95 or 98% identical to the HA2 of the first insert sequence. In an example, a third insert sequence is inserted, wherein the third insert sequence comprises respective spaced first (HA1) and second (HA2) homology arms joined by a sequence (RS), wherein HA1 of the third insert sequence is 5' of the RS thereof, and the HA1 of the third insert sequence is identical to HA2 of the second insert sequence or partially overlaps therewith or is comprised by the RS of the second insert sequence. In an example, each insert sequence is inserted by homologous recombination using its respective HA1/HA2 pair. Advantageously, none of the HA sequences of the insert sequences is the same as any of the other HA sequences.

The present invention, in its various aspects involving sequence retrieval, finds many applications in medicine, forensics, diagnostics (eg, prenatal diagnostic of disease, disease susceptibility, disease associated mutation, heredity, lineage and parenthood), archaeology, phylogeny, anthropology, food production, oil and petroleum production, environmental applications (eg, remediation), agriculture and other industrial settings. In an example, the invention provides a method of identifying a cell or source of a nucleic acid, wherein the cell comprises the donor nucleic acid sequence or wherein the source comprises said donor, wherein the method comprises the method herein for retrieving a RS into a vector, and further comprises sequencing the retrieved RS and using the sequence to identify the cell or source; or further comprises using a nucleic acid probe to probe the sequence and identify the cell or source. For example, the sequence or probe is compared with a reference sequence to carry out said identification. In a forensic example, the reference may be a reference sequence of a human (eg, a human criminal suspect) or microbe. In a diagnostic or quality control example the reference may be a reference sequence of a microbe (eg, a bacterium, archaea, yeast or virus). The quality control example, may be used in QC of an industrial process, eg, a food or beverage production or storage process; oil or petroleum recovery or processing process; or agricultural process. In an example, the retrieved sequence and the reference sequence differ by one or more SNPs (eg, human SNPs for human sequences) and the method comprises determining said difference. In an example, the retrieved sequence and the reference sequence share one or more SNPs (eg, human SNPs for human sequences) and the method comprises determining the presence of said SNP(s) in the retrieved and reference sequences. Examples of useful reference sequence databases are the 1000 Genomes database and Ensembl. In an example, the invention provides a method of pre-natal diagnosis of an animal (eg, a human) or determining parenthood of an animal (eg, a human), the method comprising providing one or more cells from the animal and carrying out the method of retrieving RS sequences according to the invention, wherein retrieval vectors comprising said first strands are introduced into said cell or cells, wherein each vector comprises HA1/HA2 corresponding to sequences found in one of the parents (or suspected parents) of the animal. In an example, all HA1/HA2 pairs correspond to sequences on one of the parents only. In a method of determining parenthood, said one parent is determined to be a parent of the animal (eg, human) when one or more retrieved sequences is comprised by said parent (first parent) but not the other (suspected) parent (second parent), eg, as indicated by a SNP match. In a RS and said first but not said second parent. In an example the RS is not a Y-chromosome sequence. In an example the RS is an X-chromosome sequence (in this case, the method of the invention can identify the presence of an RS or SNP inherited from one parent but not the other (eg, even in female children that have inherited an X-chromosome from each parent). In a diagnostic or any other method of the invention, optionally the retrieval or other vector comprises a sequence joining HA1 and HA2 wherein the sequence is not found. In the cell into which the vector is introduced or from which it is isolated. Thus, the vector is non-naturally occurring as it combines genomic sequences (such as HA1 and HA2) with sequences not from the same genome (eg, bacterial or yeast vector sequences). In an example, the retrieval method of the invention is used to determine gene sequence copy number in the genome of a host cell.

In an example, the donor strand or cell(s) are nucleic acid or cell(s) of an organ or blood of an animal, eg, a vertebrate, mammal, human, rodent, mouse or rat. For example, the donor strand or cell(s) are from a liver, kidney, brain, skin, lung, breast, prostate, GI tissue, spleen, bone marrow, pancreas, gall bladder, mouth, tongue, throat, CNS tissue, bowel, rectum, vagina, scrotum, testis, eye, ear, nose, hair, hair follicle, urethra, ovary or womb of an animal, eg, a vertebrate, mammal, human, rodent, mouse or rat. For example, the donor strand or cell(s) are from a haemopoietic cell, haemopoletic stem cell, cord blood, infant blood, adult blood, lymphocyte, T-cell. B-cell, NK-cell, dendritic cell, macrophage, platelet-producing cell or monocyte of an animal, eg, a vertebrate, mammal, human, rodent, mouse or rat.

Herein, when an RS sequence is used and inserted into a further nucleic acid strand, the insertion may be of the retrieved RS per se (ie, a direct product of a retrieval method of the invention) or may be an insertion of a copy of the retrieved RS (optionally following mutation or modification thereof, as desired).

It may be advantageous to use cutting sites on the vector (first strand) that are not found or are rarely found in the donor strand or cell genome. For example, Cas cutting can be designed to target the vector only and not the genome. Specificity can also be designed when using TALEN or zinc finger cutting. A restriction endonuclease can be used to cut the vector wherein the endonucleases recognizes a motif that in the vector that is not found in the cell (donor strand) genome, not found in the RS sequence to be retrieved or is only rarely found in the cell (donor strand genome). An example is NotI, which cuts after the first GC of an eight base pair sequence; restriction enzymes with seven and eight base pair recognition sequences may also be rare cutter endonucleases. An example of a rare cutter endonucleases is Meganuclease I-Sce I, which is a homing endonucleases that recognizes a18 base pair sequence. One or more components used to effect cutting can be introduced into the cell as a protein, a RNA (eg, mRNA), or can be encoded by a nucleotide sequence comprised by the first strand or vector that is introduced into the cell, wherein the sequence is expressed in the cell and the component is produced. The component nucleic acid sequence may be in combination with one or more nuclear localization signals (NLSs) to localize to the cell nucleus. For example, Cas enzyme can be introduced as a protein, introduced as Cas-encoding mRNA that is expressed in the cell, or is encoded by DNA (eg, by the first strand or introduced vector) for transcription and expression of the respective Cas in the cell. Alternatively, endogenous Cas expressed by the cell (when the cell is a bacterium or archaeal cell) can be harnessed to effect the cutting; in this instance one or more cRNA (or single guide RNA)-encoding sequences is introduced into the cell (eg, as mRNA or encoded by the vector or first strand) and the expressed RNA is operable to guide the endogenous Cas to effect the cutting of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications (as well as US equivalents thereof) are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

EXAMPLES

Example 1: Combining Closed Circular Vectors with In Situ Cas Cutting in Eurkaryotic Cells for Exchange of Large Nucleotide Sequences—Human Cell Gene Therapy Application This can be described by way of the following possible gene therapy procedure. An aspect is illustrated (FIG. 1) and can be carried out by constructing a population of closed circular vectors, such as DNA BACs, wherein the population comprises supercoiled vectors. To enable positive-negative selection, the vectors each can comprise a hygromycin resistance gene in the vector backbone and a HPRT gene as described below. The circular vectors can be engineered to comprise homology arms and S. pyogenes Cas9 cutting sites (ie, HA2, PS2, CS2, P2, PS1, CS1, P1, HA1 as described herein). PS1 and PS2 will be identical, as will be P1 and P2 (each being a TGG sequence), thereby enabling CS1 and CS2 both to be cut by Cas9. A sequence encoding a single (chimaeric) guide RNA (gRNA1) will be included in the vectors. CS1 will be nucleotides away from HA1 and CS2 will be 10 nucleotides away from HA2. HA1 and HA2 together can comprise 3 kb of nucleotide sequence. Cas cutting, therefore can produce cut vectors in which a sequence joining HA1 and HA2 will be cut out, whereby the cut vectors each lose a HPRT gene sequence when the joining sequences are excised. The resulting cut vectors have HA1 5' of HA2.

Closed circular vectors can be electroporated in vitro into hepatic cells that have been obtained from a human subject suffering from a disease. The cells comprise a gene sequence with a SNP that causes the disease. HA1 is 100% complementary to a sequence NS1 that is 3' of the SNP and HA2 is 100% identical to a sequence NS2 that is 5' of the SNP. Electroporation will include introduction of Cas9 vectors into the cells, the Cas9 sequence being operably linked to a U6, T7 or human promoter and a NLS so that the sequence is capable of entering the cell nuclei. Cas9 cutting of the vectors inside the cells using expressed gRNA1 will excise the HPRT and gap repair by HR of HA1/HA2 with NS1/NS2 will retrieve a 101 kb gene sequence (RS) comprising the SNP, thereby producing modified vectors. Correct retrieval can be detected using hygromycin and G418 challenge in positive-negative selection.

Correctly-modified vectors can be used with in vitro recombineering to correct the SNP in RS, thereby producing a population of closed circular insert vectors, each comprising a corrected RS sequence between two homology arms. iPS cells are derived from the human subject and these will be electroporated to introduce Cas9 vectors and insert vectors, using hygromycin and G418 detection. Cas9 cutting of the vectors inside the cells cuts sites that will have been engineered into the insert vectors flanking 10 nucleotides either side of the homology arms that flank the corrected RS (cutting is in the vector backbone and not in the RS). Cutting is effected by a second gRNA that will be expressed from a nucleotide sequence carried by the insert vectors. Cutting releases DNA fragments each comprising the corrected RS flanked by homology arms that are 100% complementary to NS1 and NS2, whereby HR between the fragments and the defective genes in the iPS cells corrects the SNP defect by HR insertion of corrected RS into the cell genomes.

Appropriate differentiated cells (eg, a liver tissue graft) are developed from the corrected iPS cells and these are used for gene therapy of the human subject to treat or prevent the disease.

Example 2: Antibiotic Methods Harnessing Endogenous Cas Nucleases

This can be described by way of the following possible procedure. This aspect can be carried out by constructing a population of engineered phagemids that are capable of infecting an undesirable S. pyogenes bacterial population. The phage genomes are engineered to comprise homology arms and *S. pyogenes* Cas9 cutting sites (ie, HA2, PS2, CS2, P2, PS1, CS1, P1, HA1 as described herein). PS1 and PS2 will be identical, as will be P1 and P2 (each being a TGG sequence), thereby enabling CS1 and CS2 both to be cut by Cas9. A sequence encoding a single (chimaeric) guide RNA (gRNA1) will be included in the genomes. CS1 will be 10 nucleotides away from HA1 and CS2 will be 10 nucleotides away from HA2. HA1 and HA2 together can comprise 3 kb of nucleotide sequence. Cas9 cutting, therefore can produce cut phage genomes in which a sequence joining HA1 and HA2 will be cut out, whereby the cut joining sequences are excised from phage vectors. The resulting cut vectors have HA1 5' of HA2.

The engineered phage are administered to a human subject suffering from a throat infection of *S. pyogenes* so that the phage infect the bacteria and introduce phage nucleic acid into the cells. HA1 is 100% complementary to a sequence NS1 that is 3' of a sequence of an essential gene of *S. pyogenes*; HA2 is 100% identical to a sequence NS2 that is 5' of the gene sequence. The Hip gene will be targeted as this is essential (Appl Environ Microbiol. 2011 July; 77(13): 4422-4428; doi: 10.1128/AEM.00554-11; "The Histone-Like Protein Hip Is Essential for Growth of *Streptococcus pyogenes*: Comparison of Genetic Approaches To Study Essential Genes"; *Julia* V. Bugrysheva et al). Electroporation will exclude introduction of Cas9 protein into the cells as the functional endogenous *S. pyogenes* Cas9 will be harnessed using a single guide RNA (gRNA1) that is expressed from a sequence carried by the phage genomes. Cas9 cutting of the phage vectors inside the cells using expressed gRNA1 will excise sequence joining HA1 and HA2 and gap repair by HR of HA1/HA2 with NS1/NS2 will retrieve the hip gene sequence (RS), thereby excising this sequence from the genomes of the target bacterial cells. Correct retrieval therefore will lead to cell death as hip is rendered inactive, thereby reducing the severity or removing the infection in the human.

In alternative applications, a similar approach can be used to target one or more bacterial species in a mixed population in the gut microbiome of a human subject. This re-balances the gut microbiome. In another application, a sample of microbiome is combined in vitro with phage that infect Bacteriodetes species, the phage being retrieval vectors as per the invention and the targeted bacterioidetes can thus be killed. This alters the Firmicutes: bacteroidetes ratio in the population. A sample of the re-balanced population is intranasally transplanted into the donor or a different human subject to treat or prevent obesity.

In an alternative application, sulphur-reducing bacteria (SRB) are targeted using a similar approach, wherein the bacteria are comprised by an oil field or comprised by oil recovery or processing equipment. In this way, SRB can be killed, thereby reducing microbially influenced corrosion of oil field, or oil recover or processing equipment.

Example 3: Vector Formats

FIGS. 2A & B show a single-arm vector for use in the present invention. The homology arm HA1 is at least 100 kb in length and is at least 90% identical to a target sequence NS1 in a target nucleic acid. As shown, Cas cutting in the presence of a guide RNA (gRNA1) produces a recombinogenic end that is close (less than 250 nt) away from HA1, which is useful for efficient HR with the target. HR can be used, for example, to insert into the target nucleic acid a SNP or PAM site contained in HA1. HR can be used to insert a vector sequence outside HA1, for example, where the sequence is within 100 nt of HA1 for maximising the chances of HR insertion into the target.

Figure 3A:
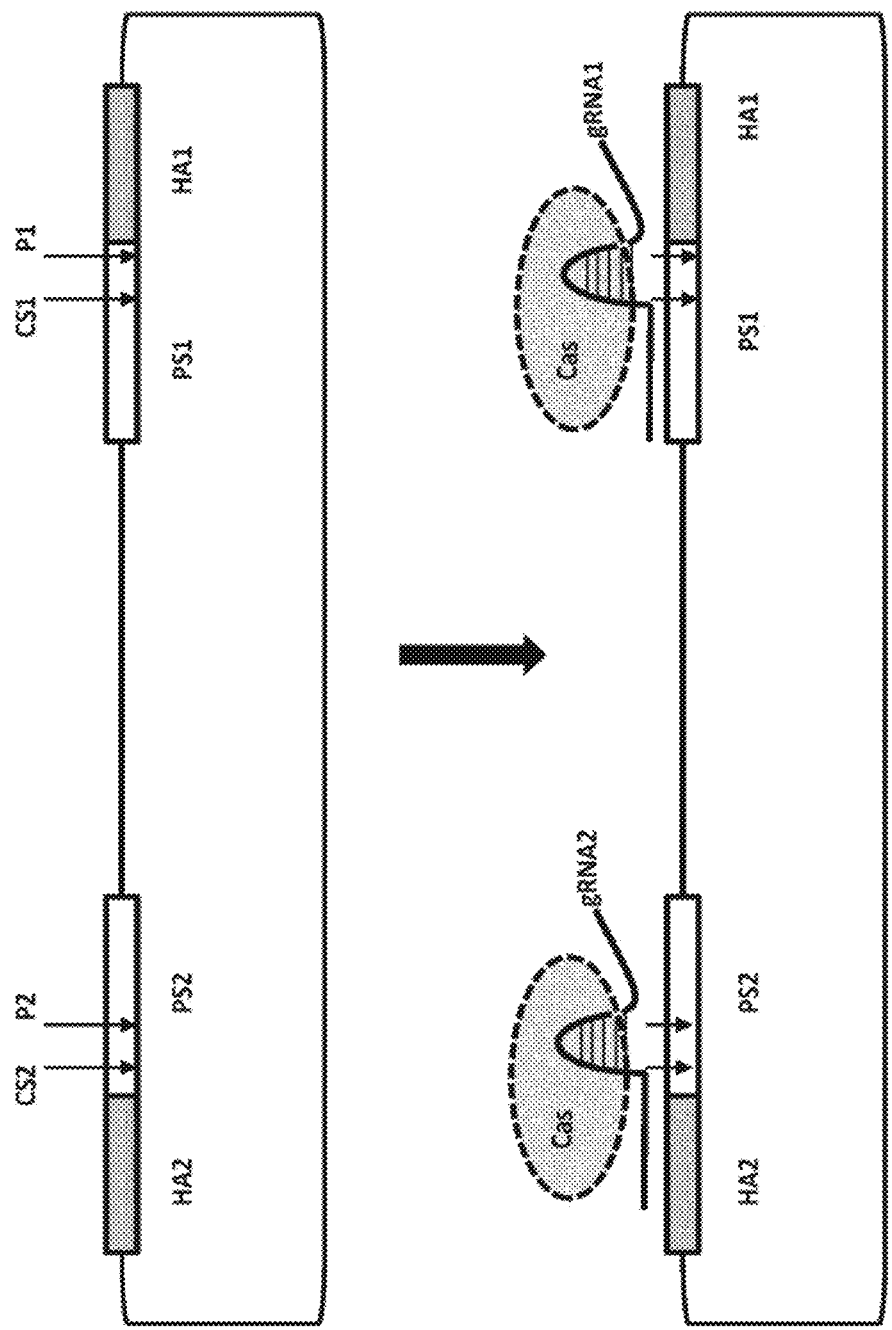
FIG. 3A shows a variation where a circular vector comprises two Cas cutting sites (eg, for use as a retrieval vector to or an insert vector according to the invention).

FIG. 3A shows a variation where a circular vector comprises two Cas cutting sites (eg, for use as a retrieval vector to or an insert vector according to the invention). Cutting can be with different gRNAs (as shown) or the same gRNA. Also cutting can be with two different Cas nucleases (used simultaneously or sequentially) to cut the cutting sites.

FIG. 3B shows a variation where PAM sites have been identified in the homology arm(s), engineered into the arm(s) or the arm(s) have been selected from sequence of the target nucleic acid or cell to contain appropriately placed PAM. Cas cutting in this variation provides the recombinogenic end in the homology arm(s) to promote efficient HR. As shown, a marker (eg, HPRT) can be included to indicate successful excision of the sequence joining the cut sites. In the second vector.

FIG. 4 shows release of a marker fragment to produce two recombinogenic ends in a retrieval vector. In this instance, the starting vector does not rely on having to find suitable arms with PAMs or to engineer PAMs into arms. Instead, PAMs are provided in protospacer sequences instead, which can be more readily designed than being confined by the need for suitable homology to target sequences. As seen in FIG. 4B, HR with a donor strand retrieves a donor fragment containing a desired RS. The retrieved fragment can be large or very large (eg, greater than 100 kb) as it is retrieved into a closed circular vector In situ (eg, inside a cell where HR takes place). Once in the closed circular vector, the RS can be readily used in subsequent genetic engineering (eg, recombineering) methods in vitro or purified. The closed circular vector, as is illustrated in FIG. 4C, can be used in gene therapy or to modify a target nucleic acid in vitro or in any prokaryotic or eukaryotic cell using HR, with large or very large sequences containing RS being manageable by virtue of being harboured by a closed circular vector. In an alternative, SSR sites (eg incompatible lox sites as shown) can be engineered into the vector before or after retrieval of RS (eg, engineered by recombineering). The SSR sites can be used to recombine with sites. In a target strand to insert RS into the latter. As shown in FIG. 4D, this allows for RMCE insertion of RS and also for specifically introducing changes into the target. If the lox sites in the product target strand are flanked by piggyBac sites, then transient expression of PB transposase will cleanly excise the SSR sites, leaving just the RS behind. This is useful when carried out in an ES cell or iPS cell, for example a human iPS cell or a mouse ES cell.

Figure 5B:
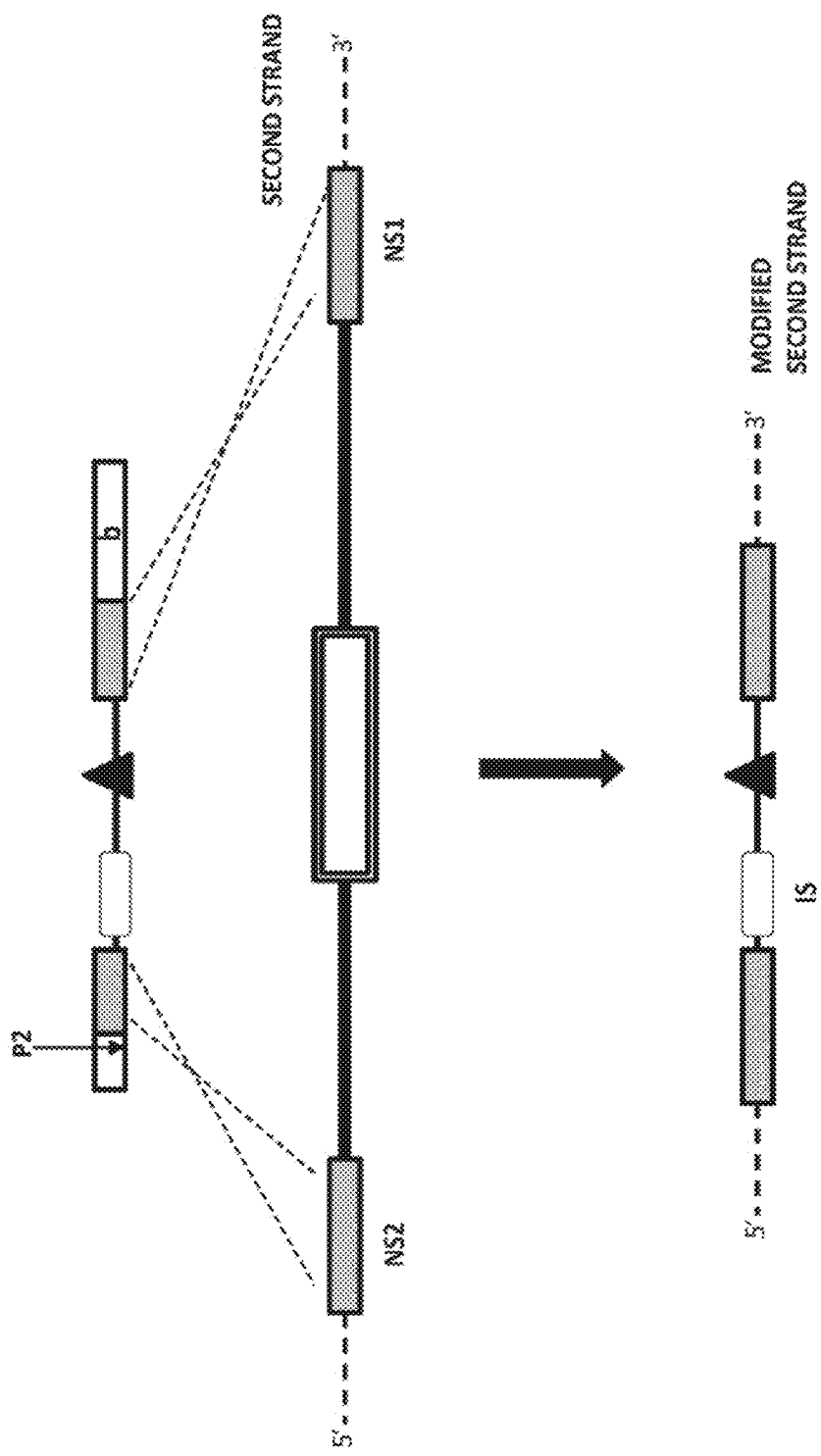
In FIG. 5C, the vector homology arms are complementary to sequences that are spaced in the target strand (spaced by a sequence including a sequence (rectangular box) that is deleted). No IS in inserted.
Figure 5C:
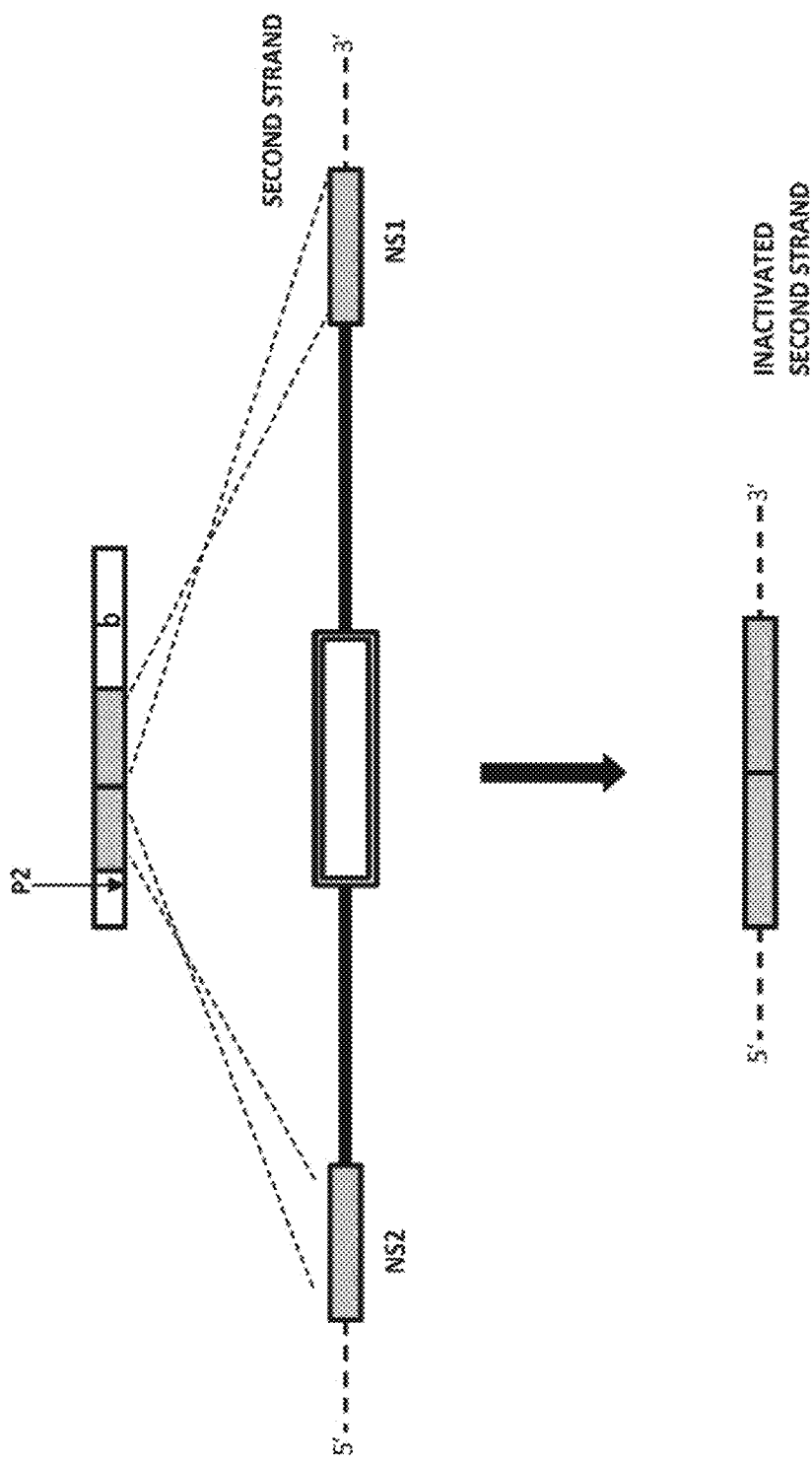

FIG. 5A shows the release of a recombinogenic nucleic acid fragment that can be used in a subsequent process of HR with a target (FIG. 5B) for insertion of an insert sequence (eg, a regulatory element or exon sequence). As shown in FIG. 5A, an optional marker can be included in the release fragment. As also shown, excision of this fragment from the vector can produce a new marker sequence formed of a 5' sequence of PS2 (a) with a 3' sequence of PS1 (S1). In this example, the sequence aS1 is present in the modified vector but not in unmodified vectors. The aS1 sequence can be detected by POR or can be expressible to produce a detectable marker protein (eg, antibiotic resistance). In FIG. 5B, sequence replacement. In the target (second strand) is shown—here a sequence (rectangular box) is deleted and IS inserted in its place. In FIG. 5C, the vector homology arms are complementary to sequences that are spaced in the target strand (spaced by a sequence including a sequence (rectangular box) that is deleted). No IS in inserted. This can be used, for example, to inactivate a gene in the target (eg, when the target is comprised by a pathogenic bacterium, for example, and the deleted sequence is a sequence of an essential, virulence or antibiotic resistance gene).

Figure 6A:
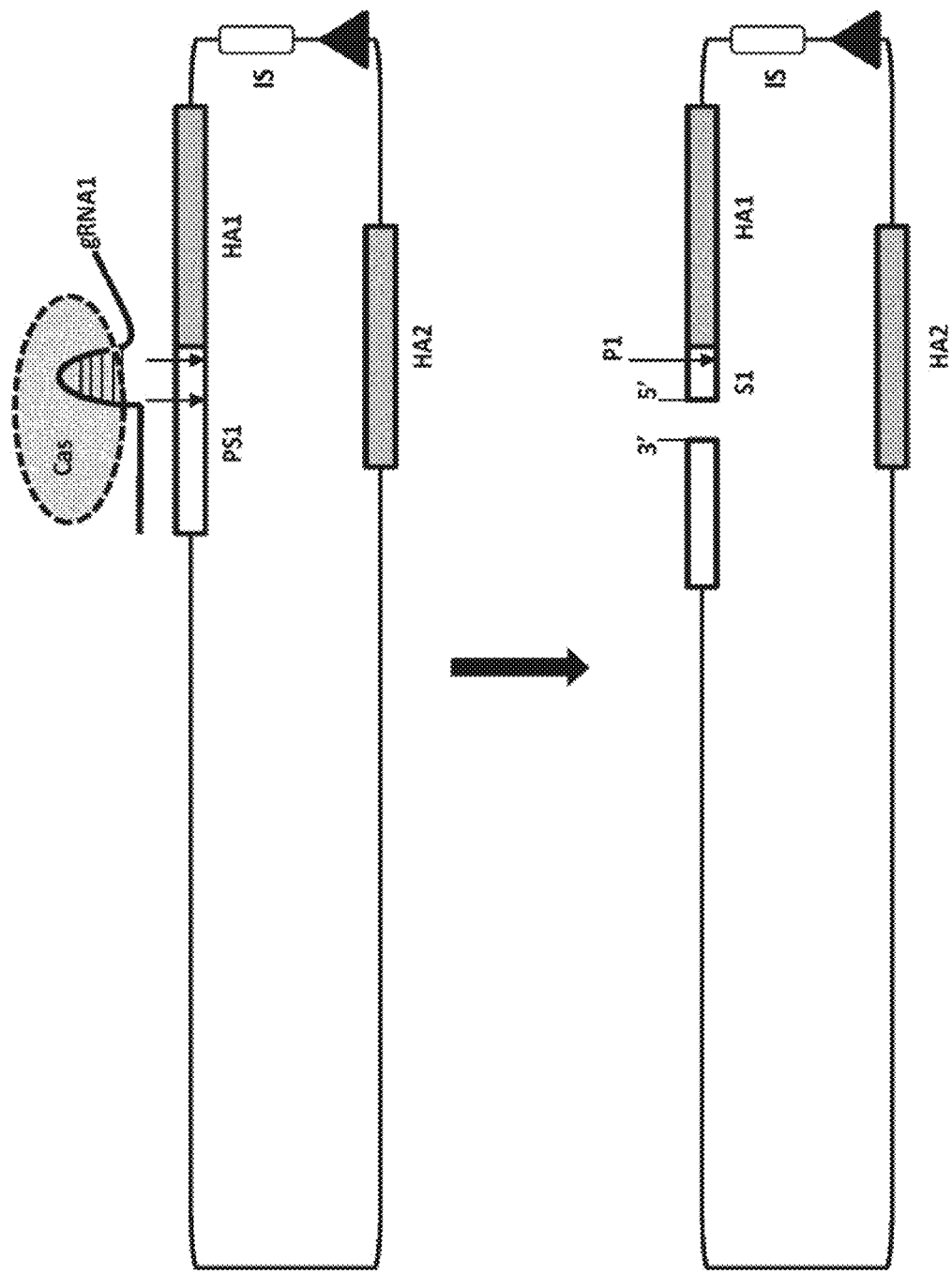
Figure 6B:
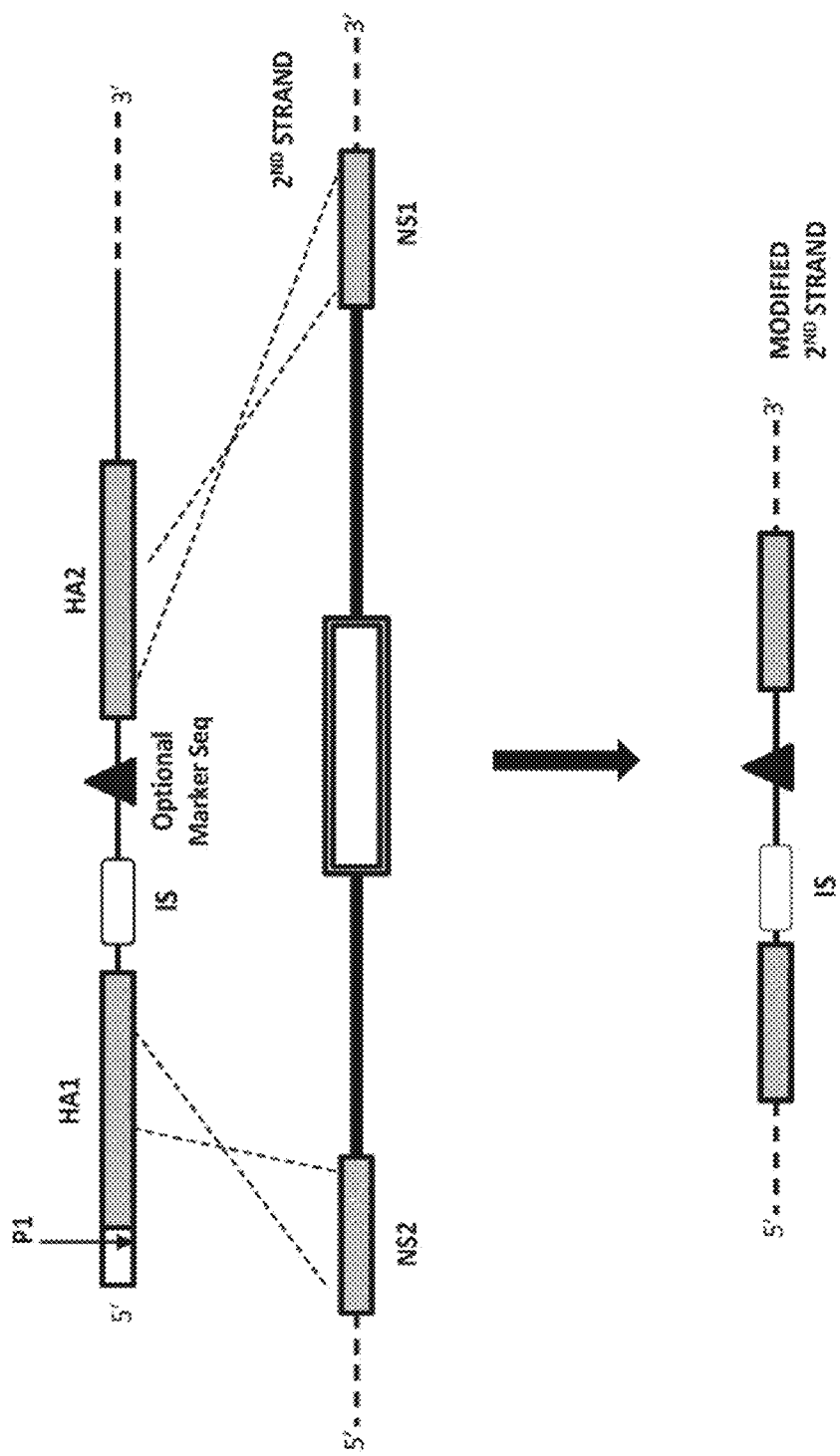
Figure 7A:
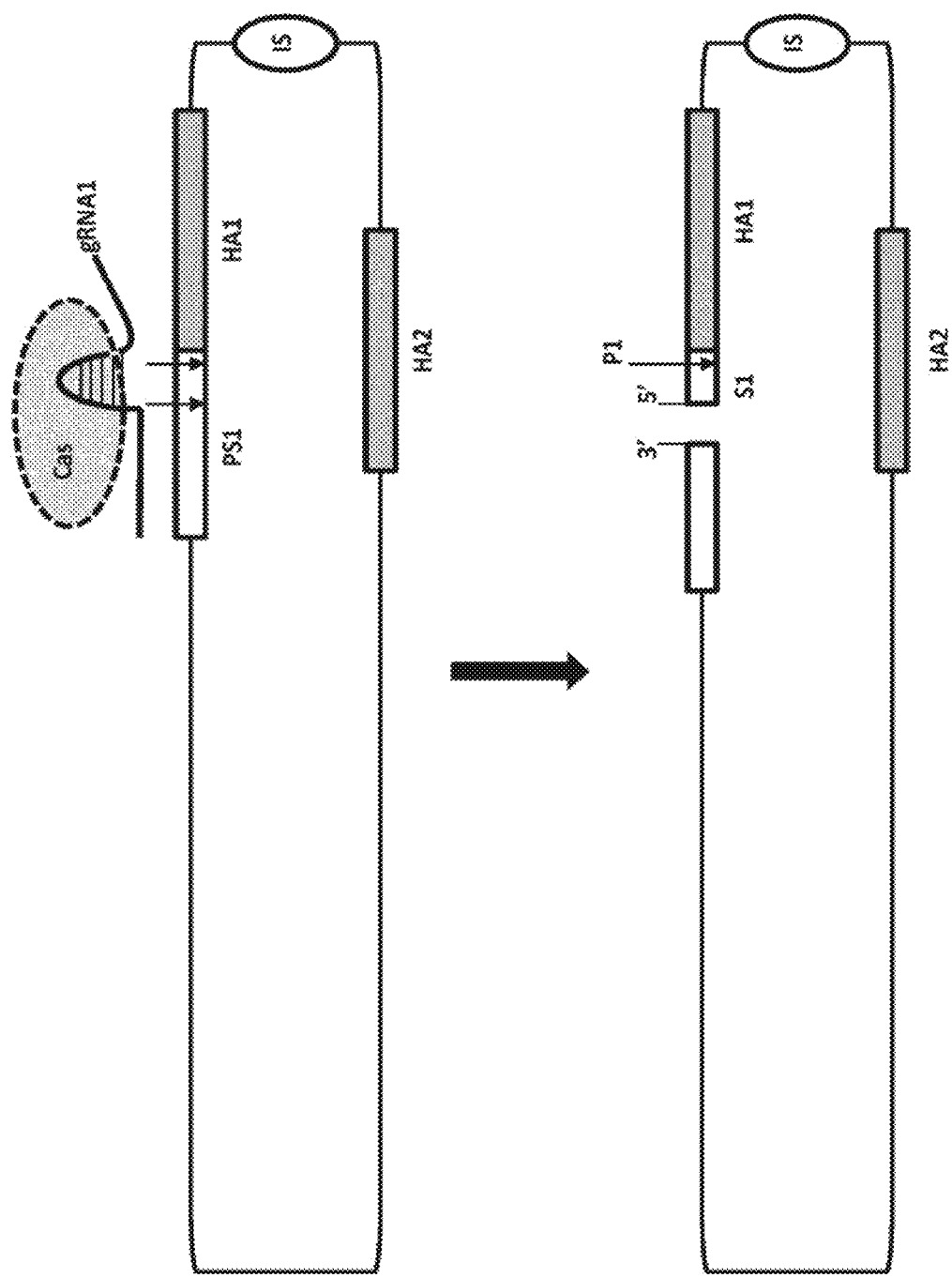
FIGS. 7A & 7B shows how insertion (le, not replacement, which involves target sequence deletion) is carried out.
Figure 7B:
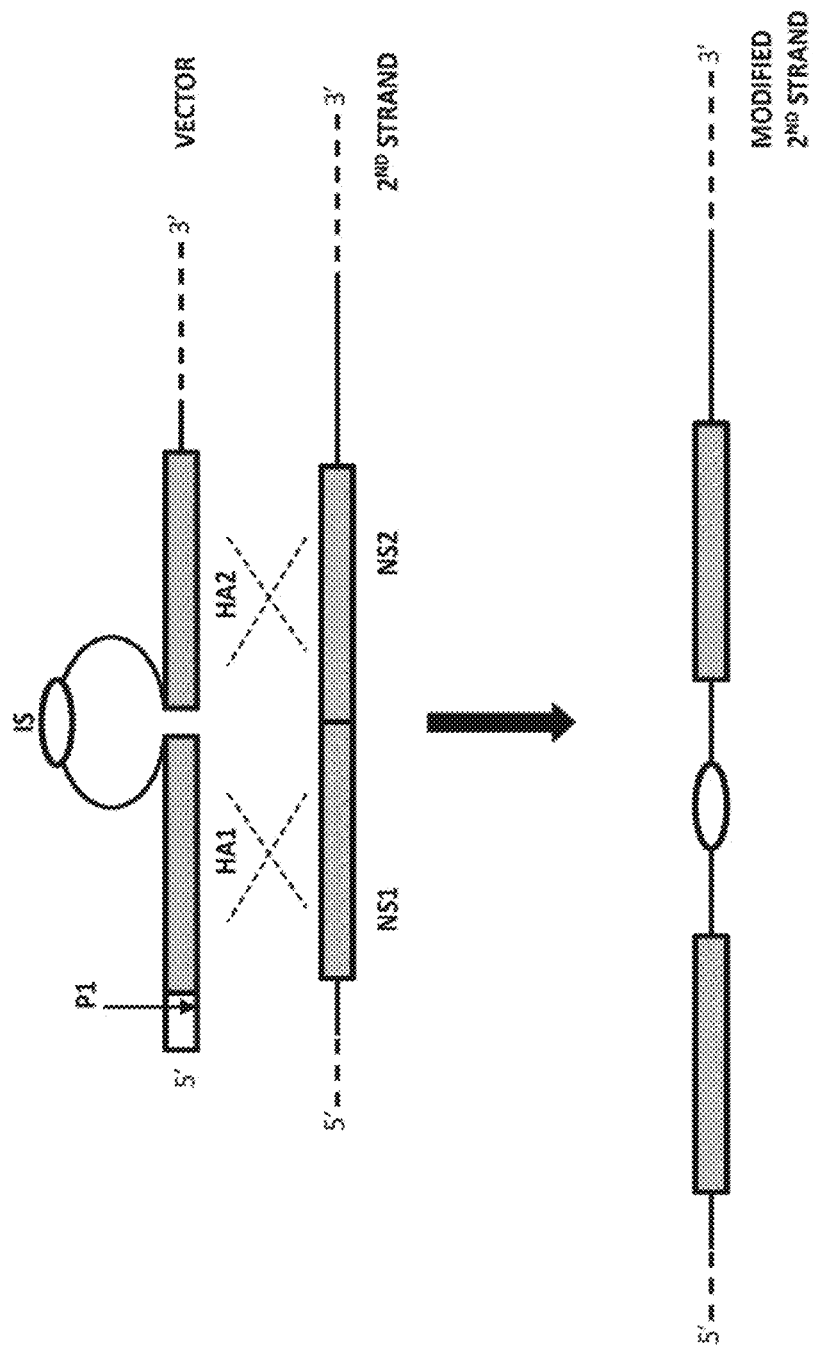

FIGS. 6A and 68 show an application of an insert vector where Cas cutting is at one site close to a first homology arm. Efficiency and specificity of targeting in HR is provided by including a second arm (HA2) with an insert sequence (IS) between the arms. In this example, replacement of a target sequence takes place (FIG. 6B). In FIG. 78, insertion (ie, not replacement, which involves target sequence deletion) is carried out.

Figure 8A:
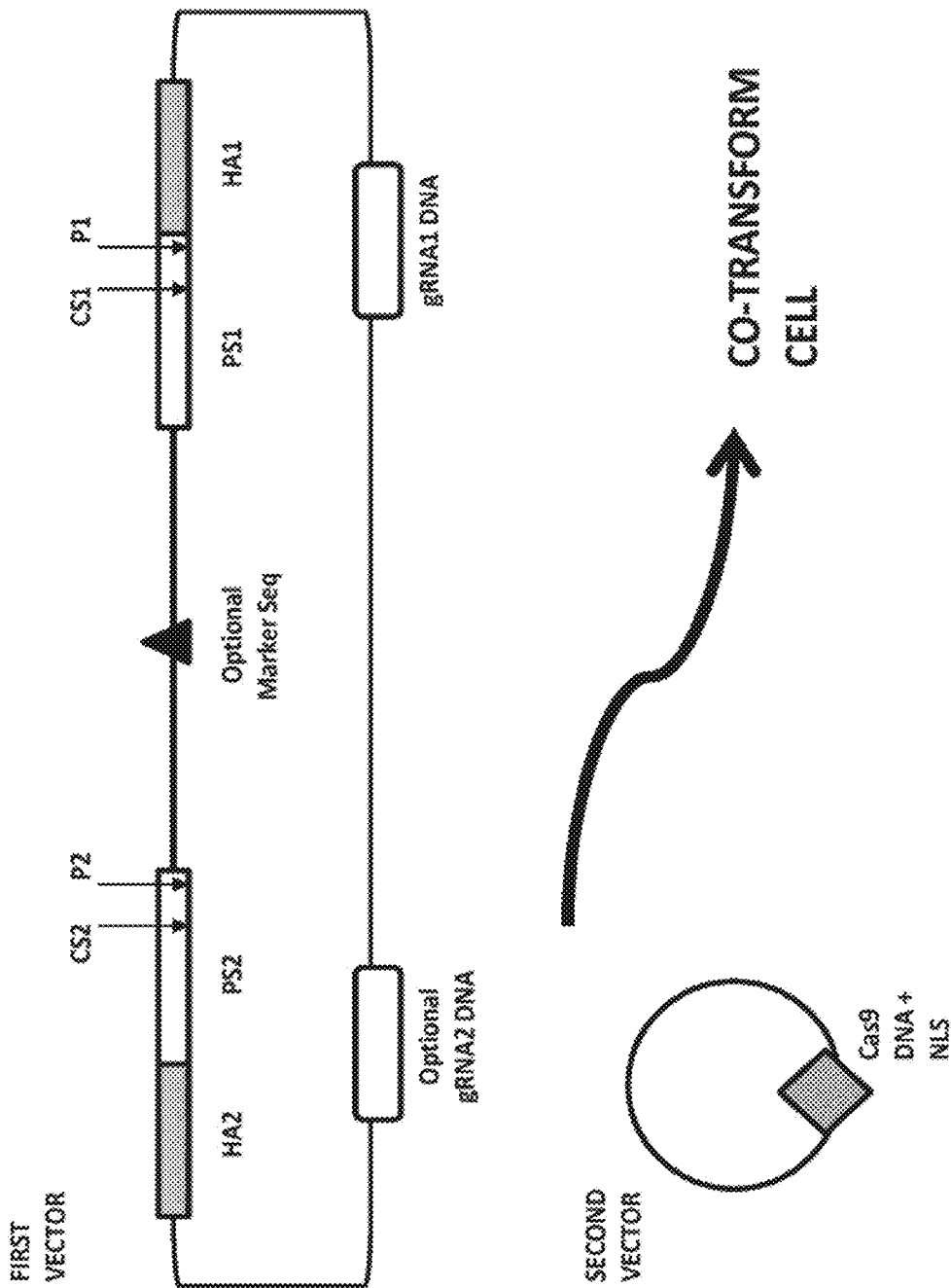
FIG. 8A illustrates co-transformation of a vector of the invention with a Cas vector.
Figure 8B:
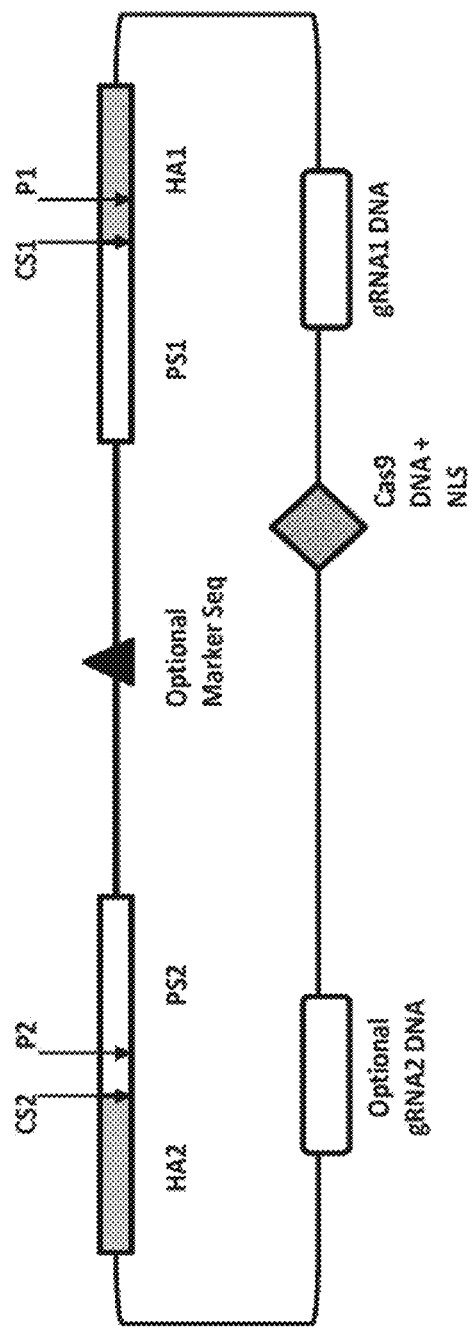
FIG. 8B shows a variation where the Cas9 sequence is included in the vector of the invention.

FIG. 8A illustrates co-transformation of a vector of the invention with a Cas vector. When P1 and P2 are identical and also PS1 & PS2 are identical, gRNA1 acts at CS1 & CS2 (gRNA2 DNA is can be omitted). When the target cell comprises an endogenous Cas that is cognate to the vector protospacers and PAM, the Cas vector can be omitted. FIG. 8B shows a variation where the Cas9 sequence is included in the vector of the invention.

Figure 9B:
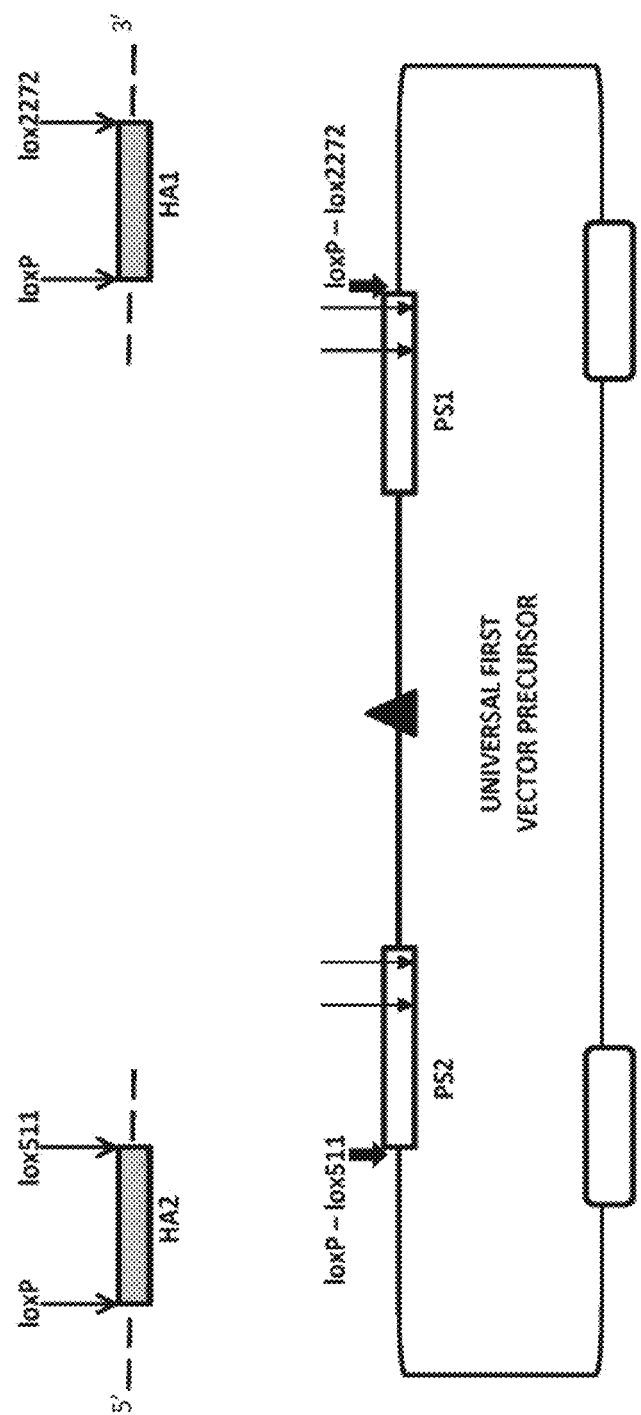
FIG. 9A shows a precursor vector of the invention. Cloning sites are engineered into the vector for subsequent use to drop in one or more homology arms (HA1 and/or HA2). This is illustrated in FIGS. 98 & 9C using RMCE with incompatible SSR (lox sites).
FIGS. 9D & 9E show a variation using restriction endonucleases.
Figure 9C:
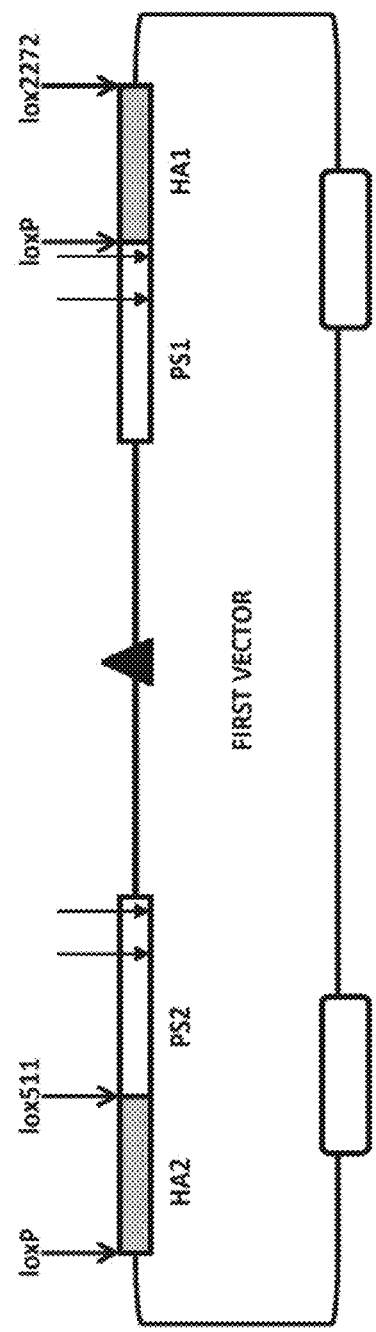
Figure 9D:
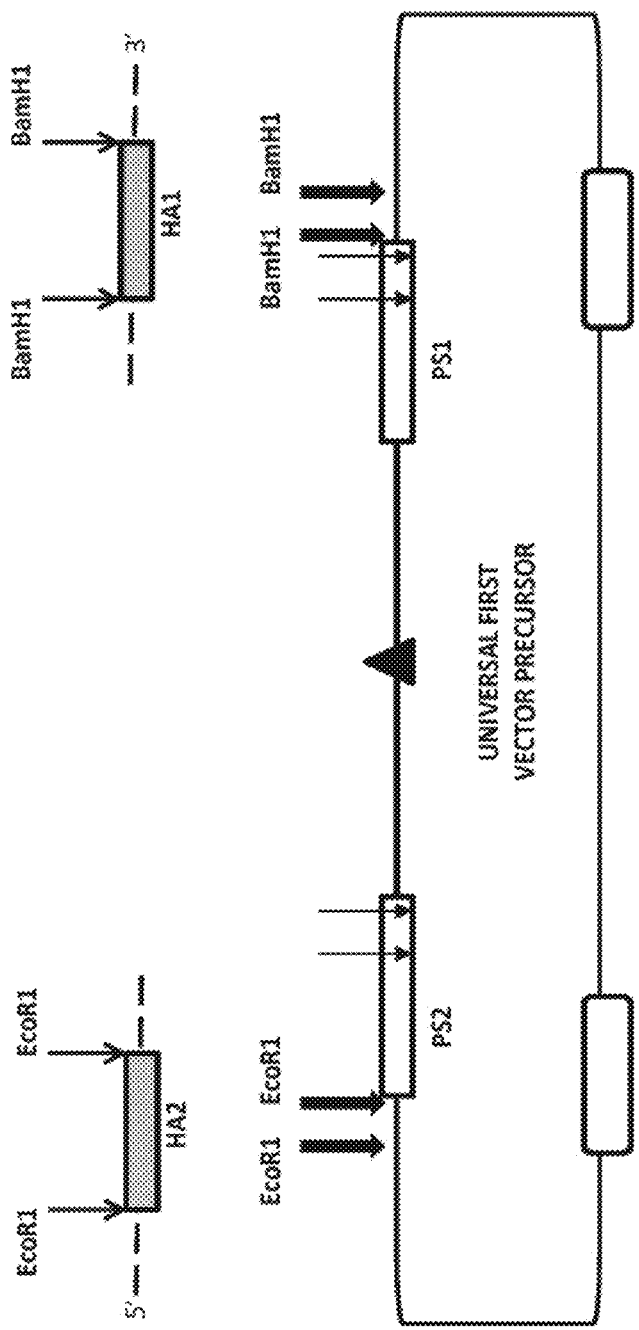
Figure 9E:
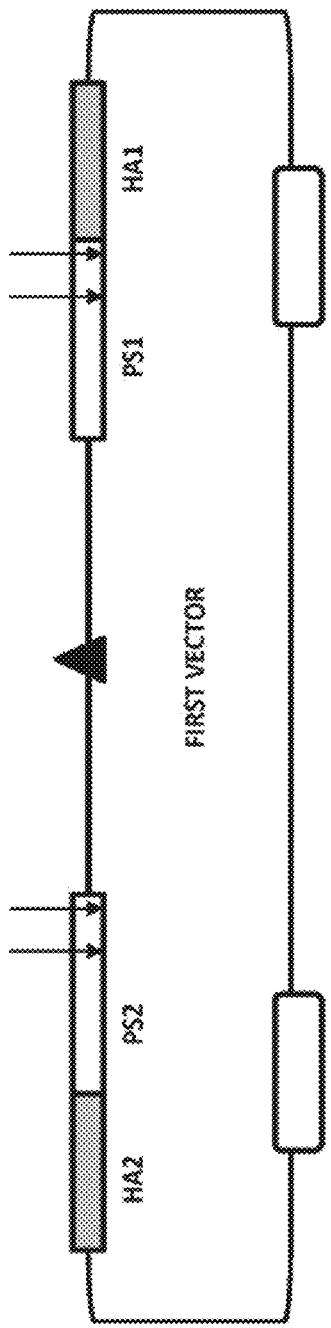

FIG. 9A shows a precursor vector of the invention. Cloning sites are engineered into the vector for subsequent use to drop in one or more homology arms (HA1 and/or HA2). This is illustrated in FIGS. 9B & 9C using RMCE with incompatible SSR (lox sites). This can be performed in vitro before carrying out modification of target nucleic strands or cells with the product vector. FIGS. 9D & 9E show a variation using restriction endonucleases.

The invention claimed is:

1. An in vitro method comprising
(A) combining
  (a) a first DNA molecule, wherein the first DNA molecule is a double-stranded DNA molecule or a single-stranded DNA molecule,
  (b) a further DNA molecule, wherein the further DNA molecule is single-stranded DNA (ssDNA); and
  (c) an RNA-guided nuclease and a guide RNA;
  wherein the nuclease is a Cas3 or Cpf1; and
  the first DNA molecule comprises a first protospacer sequence (PS1) and a protospacer adjacent motif (PAM) (P1), wherein P1 is cognate to the nuclease for cutting PS1 at a first cut site (CS1) and wherein PS1 is adjacent to P1;
  wherein the first DNA molecule is exposed to the guide RNA, wherein the guide RNA hybridizes to PS1;
(B) cutting the further DNA molecule with the nuclease to form a new marker; and
(C) detecting the marker.

2. The method of claim 1, wherein the marker is a sequence that is detectable by polymerase chain reaction (PCR).

3. The method of claim 2, wherein detecting the marker in (C) comprises detecting the marker by polymerase chain reaction (PCR).

4. The method of claim 1, wherein PS1 consists of 15 to 45 contiguous nucleotides.

5. The method of claim 1, wherein the first DNA molecule is a ssDNA.

6. The method of claim 1, wherein the nuclease is Cas3.

7. The method of claim 1, wherein the nuclease is Cpf1.

8. The method of claim 1, comprising isolating the further DNA molecule after the cutting in (B).

9. The method of claim 1, comprising sequencing the further DNA molecule after the cutting in (B).

10. The method of claim 1, wherein the method is carried out in a bacterial cell.

11. The method of claim 1, wherein the nuclease cuts PS1.

12. The method of claim 1, wherein a sequence is deleted from the further DNA molecule to form the new marker.

\* \* \* \* \*